United States Patent
Kim et al.

(10) Patent No.: US 12,102,001 B2
(45) Date of Patent: Sep. 24, 2024

(54) ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

(71) Applicant: ROHM AND HAAS ELECTRONIC MATERIALS KOREA LTD., Chungcheongnam-do (KR)

(72) Inventors: Young-Kwang Kim, Gyeonggi-do (KR); Hong-Se Oh, Gyeonggi-do (KR); Ji-Song Jun, Gyeonggi-do (KR); Chi-Sik Kim, Gyeonggi-do (KR); Kyoung-Jin Park, Gyeonggi-do (KR); Doo-Hyeon Moon, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 706 days.

(21) Appl. No.: 17/188,999

(22) Filed: Mar. 1, 2021

(65) Prior Publication Data

US 2021/0280796 A1    Sep. 9, 2021

(30) Foreign Application Priority Data

Mar. 2, 2020  (KR) .................. 10-2020-0025972
Jan. 14, 2021  (KR) .................. 10-2021-0005116

(51) Int. Cl.
| | | |
|---|---|---|
| H10K 85/60 | (2023.01) |
| C07D 491/18 | (2006.01) |
| C09K 11/06 | (2006.01) |
| H10K 50/11 | (2023.01) |
| H10K 101/00 | (2023.01) |
| H10K 101/10 | (2023.01) |

(52) U.S. Cl.
CPC ......... *H10K 85/657* (2023.02); *C07D 491/18* (2013.01); *C09K 11/06* (2013.01); *H10K 85/6572* (2023.02); *C09K 2211/1018* (2013.01); *H10K 50/11* (2023.02); *H10K 2101/10* (2023.02); *H10K 2101/90* (2023.02)

(58) Field of Classification Search
None
See application file for complete search history.

(56) References Cited

U.S. PATENT DOCUMENTS

2018/0138419 A1    5/2018   Dyatkin et al.

*Primary Examiner* — Jeffrey D Washville
(74) *Attorney, Agent, or Firm* — G. Creston Campbell

(57) ABSTRACT

The present disclosure relates to an organic electroluminescent compound, an organic electroluminescent material comprising the same, and an organic electroluminescent device. By comprising the organic electroluminescent compound according to the present disclosure, an organic electroluminescent device having low driving voltage and/or high luminous efficiency and/or long lifespan can be provided.

11 Claims, No Drawings

ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

TECHNICAL FIELD

The present disclosure relates to an organic electroluminescent compound, an organic electroluminescent material comprising the same, and organic electroluminescent device.

BACKGROUND ART

An electroluminescent device (EL device) is a self-light-emitting display device which has advantages in that it provides a wider viewing angle, a greater contrast ratio, and a faster response time. The organic EL device was first developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device (OLED) is light-emitting materials. Until now, fluorescent materials have been widely used as light-emitting materials. However, in view of electroluminescent mechanisms, since phosphorescent light-emitting materials theoretically enhance luminous efficiency by four (4) times compared to fluorescent light-emitting materials, phosphorescent light-emitting materials have been widely researched. Until now, Iridium (III) complexes have been widely known as phosphorescent light-emitting materials, including bis(2-(2'-benzothienyl)-pyridinato-N,C-3')iridium(acetylacetonate) [(acac)Ir(btp)$_2$], tris(2-phenylpyridine)iridium [Ir(ppy)$_3$] and bis(4,6-difluorophenylpyridinato-N,C2)picolinato iridium (Firpic) as red-, green-, and blue-emitting materials, respectively.

In the prior art, 4,4'-N,N'-dicarbazol-biphenyl (CBP) is the most widely known phosphorescent host material. Recently, Pioneer (Japan) et al., developed a high performance OLED using bathocuproine (BCP) and aluminum (III)bis(2-methyl-8-quinolinate)(4-phenylphenolate) (BAlq), etc., as host materials, which were known as hole blocking materials.

However, although the conventional materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the OLED is given by [(π/voltage)× current efficiency], and the power efficiency is inversely proportional to the voltage. Although the OLED comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the OLED is short, and it is still necessary to improve luminous efficiency.

In order to improve luminous efficiency, operating voltage and/or lifetime, various materials or concepts for an organic layer of an OLED have been proposed, but they have not been satisfactory in practical use.

DISCLOSURE OF INVENTION

Technical Problem

The object of the present disclosure is firstly, to provide an organic electroluminescent compound and an organic electroluminescent material comprising the same which is effective to produce an organic electroluminescent device having low driving voltage and/or high luminous efficiency and/or long lifespan, and secondly, to provide an organic electroluminescent device comprising the organic electroluminescent material.

Solution to Problem

As a result of intensive studies to solve the technical problem above, the present inventors found that the aforementioned objective can be achieved by an organic electroluminescent compound represented by the following formula 1, so that the present invention was completed.

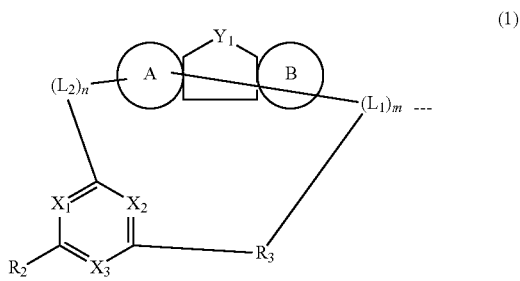

(1)

In formula 1,
A ring and B ring each independently represent a substituted or unsubstituted (C6-C30)aryl or a substituted or unsubstituted (3- to 30-membered)heteroaryl;
$X_1$ to $X_3$ each independently represent N or $CR_{11}$;
$R_2$ and Ru each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of an (C3-C30) aliphatic ring and an (C6-C30) aromatic ring, or -L$_3$-N—(Ar$_2$)(Ar$_3$); or may be linked to an adjacent substituent to form a ring(s);
L$_3$ represents a single bond, a substituted or unsubstituted (C6-C30)arylene, or a substituted or unsubstituted (3- to 30-membered)heteroarylene;
Ar$_2$ and Ar$_3$ each independently represent hydrogen, a substituted or unsubstituted (C1-C30)alkyl, a substituted or unsubstituted (C2-C30)alkenyl, a substituted or unsubstituted fused ring of an (C3-C30) aliphatic ring and an (C6-C30) aromatic ring, a substituted or unsubstituted (C6-C30)aryl, or a substituted or unsubstituted (3- to 30-membered)heteroaryl;
L$_1$, L$_2$, and R$_3$ each independently represent a single bond, a substituted or unsubstituted (C6-C30)arylene, or a substituted or unsubstituted (3- to 30-membered)heteroarylene; with the proviso that when $R_2$ is linked to adjacent $R_{11}$ to form a fused ring(s), $L_2$ represents a single bond;

$Y_1$ represents a single bond, —O—, —S—, —N—$Ar_1$, —$R_{12}C=CR_{12'}$—, —$R_{13}R_{14}C$—$CR_{13'}R_{14'}$—, of —$CR_{15}R_{16}$; provided that when $L_1$ is linked to $Y_1$, $Y_1$ represents —N—;

$Ar_1$ represents a substituted or unsubstituted (C6-C30)aryl or a substituted or unsubstituted (3- to 30-membered) heteroaryl;

$R_{12}$ to $R_{16}$, $R_{12'}$, $R_{13'}$, and $R_{14'}$ each independently represent hydrogen, a substituted or unsubstituted (C1-C30)alkyl, a substituted or unsubstituted (C6-C30)aryl, or a substituted or unsubstituted (3- to 30-membered) heteroaryl; or may be linked to an adjacent substituent to form a ring(s);

m and n each independently represent an integer of 1 or 2; and when m and n are 2 or more, each of $L_1$ and $L_2$ may be the same or different.

Advantageous Effects of Invention

By comprising an organic electroluminescent compound according to the present disclosure and an organic electroluminescent material comprising the same, an organic electroluminescent device having low driving voltage and/or high luminous efficiency and/or long lifespan can be prepared.

MODE FOR THE INVENTION

Hereinafter, the present disclosure will be described in detail. However, the following description is intended to explain the invention, and is not meant in any way to restrict the scope of the invention.

The present disclosure relates to an organic electroluminescent compound represented by the formula 1, an organic electroluminescent material comprising the organic electroluminescent compound, and an organic electroluminescent device comprising the organic electroluminescent material.

The term "organic electroluminescent compound" in the present disclosure means a compound that may be used in an organic electroluminescent device, and may be comprised in any material layer constituting an organic electroluminescent device, as necessary.

Herein, "organic electroluminescent material" means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

Herein, "a plurality of host materials" means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The two or more compounds comprised in the plurality of host materials of the present disclosure may be included in one light-emitting layer or may be respectively included in different light-emitting layers. When the at least two host materials are comprised in one layer, the at least two host materials may be mixture-evaporated to form a layer, or simultaneously may be co-evaporated individually to form a layer.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, and tert-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. Herein, "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and comprise a spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl. 1-chrysenyl, 2-chrysenyl, 3-chrysenyl, 4-chrysenyl. 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, etc. Herein, "(3- to 30-membered) heteroaryl(ene)" is an aryl having 3 to 30 ring backbone atoms which the number of ring backbone atoms is preferably 5 to 25, including at least one, preferably 1 to 4 heteroatoms selected from the group consisting of B, N, O, S, Si, P, and Ge. The above heteroaryl may be a monocyclic ring, or a fused ring condensed with at least one benzene ring; and may be partially saturated. Also, the above heteroaryl herein may be one formed by linking at least one heteroaryl or aryl group to a heteroaryl group via a single bond(s). Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acrylidinyl, silafluorenyl, germafluorenyl, etc. More specifically, the heteroaryl may be 1-pyrrolyl, 2-pyrrolyl, 3-pyrrolyl. 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl. 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl. 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyi-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acrylidinyl, 2-acrylidinyl, 3-acrylidinyl, 4-acrylidinyl, 9-acrylidinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Herein, "Halogen" includes F, Cl, Br, and I.

In addition, "ortho (o)," "meta (m)," and "para (p)" are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, the term "a ring formed in linking to an adjacent substituent" means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (3- to 26-membered) mono- or polycyclic, alicyclic, aromatic ring, or a combination thereof. Further, the formed ring may be included at least one heteroatom selected from the group consisting of B, N, O, S, Si and P, preferably at least one heteroatom selected from the group consisting of N, O and S. According to one embodiment of the present disclosure, the number of atoms in the ring skeleton is 5 to 20; according to another embodiment of the present disclosure, the number of atoms in the ring skeleton is 5 to 15. In one embodiment, the linked or fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring, etc.

In addition, "substituted" in the expression "substituted or unsubstituted" described in of the present disclosure means that a hydrogen atom in a certain functional group is replaced with another atom or functional group, i.e., a substituent. The substituent of the substituted (C1-C30) alkyl, the substituted (C2-C30)alkenyl, the substituted (C6-C30)aryl(ene), the substituted (3- to 30-membered)heteroaryl(ene), the substituted tri(C1-C30)alkylsilyl, the substituted di(C1-C30)alkyl(C6-C30)arylsilyl, the substituted (C1-C30)alkyldi(C6-C30)arylsilyl, the substituted tri (C6-C30)arylsilyl, and the substituted fused ring of the (C3-C30) aliphatic ring and the (C6-C30) aromatic ring, each independently are at least one selected from the group consisting of deuterium, halogen, cyano, carboxyl, nitro, hydroxy, (C1-C30)alkyl, halo(C1-C30)alkyl, (C2-C30)alkenyl, (C2-C30)alkynyl, (C1-C30)alkoxy, (C1-C30)alkyithio, (C3-C30)cycloalkyl, (C3-C30)cycloalkenyl, (3- to 7-membered)heterocycloalkyl. (C6-C30)aryloxy, (C6-C30) arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of an (C3-C30) aliphatic ring and an (C6-C30) aromatic ring, amino, mono- or di-(C1-C30)alkylamino, mono- or di-(C2-C30)alkenylamino, (C1-C30)alkyl(C2-C30)alkenylamino, mono- or di-(C6-C30)arylamino. (C1-C30)alkyl (C6-C30)arylamino, mono- or di-(3- to 30-membered)heteroarylamino, (C1-C30)alkyl(3- to 30-membered) heteroarylamino, (C2-C30)alkenyl(C6-C30)arylamino, (C2-C30)alkenyl(3- to 30-membered)heteroarylamino, (C6-C30)aryl(3- to 30-membered)heteroarylamino, (C1-C30) alkylcarbonyl, (C1-C30)alkoxycarbonyl, (C6-C30) arylcarbonyl, di(C6-C30)arylboronyl, di(C1-C30) alkylboronyl, (C1-C30)alkyl(C6-C30)arylboronyl, (C6-C30)ar(C1-C30)alkyl, and (C1-C30)alkyl(C6-C30)aryl. For example, the substituent may be methyl, cyano, triphenylsilyl, phenyl, biphenyl, naphthyl, dibenzofuranyl, carbazolyl, dibenzothiophenyl, spirobifluorenyl, benzofurocarbazolyl, benzothienocarbazolyl, triphenylenyl, or fluorenyl unsubstituted or substituted with at leas one of phenyl and methyl, etc.

Hereinafter, the organic electroluminescent compound according to one embodiment will be described.

The organic electroluminescent compound according to one embodiment is represented by the following formula 1.

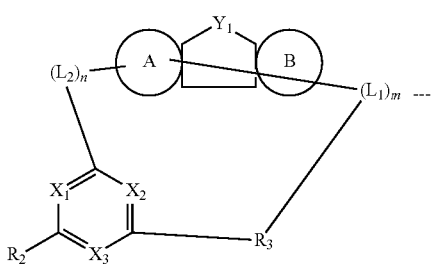
(1)

In formula 1,

A ring and B ring each independently represent a substituted or unsubstituted (C6-C30)aryl or a substituted or unsubstituted (3- to 30-membered)heteroaryl;

$X_1$ to $X_3$ each independently represent N or $CR_{11}$;

$R_2$ and Ru each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of an (C3-C30) aliphatic ring and an (C6-C30) aromatic ring, or $-L_3-N-(Ar_2)(Ar_3)$; or may be linked to an adjacent substituent to form a ring(s);

$L_3$ represents a single bond, a substituted or unsubstituted (C6-C30)arylene, or a substituted or unsubstituted (3- to 30-membered)heteroarylene;

$Ar_2$ and $Ar_3$ each independently represent hydrogen, a substituted or unsubstituted (C1-C30)alkyl, a substituted or unsubstituted (C2-C30)alkenyl, a substituted or unsubstituted fused ring of an (C3-C30) aliphatic ring and an (C6-C30) aromatic ring, a substituted or unsubstituted (C6-C30)aryl, or a substituted or unsubstituted (3- to 30-membered)heteroaryl;

$L_1$, $L_2$, and $R_3$ each independently represent a single bond, a substituted or unsubstituted (C6-C30)arylene, or a substituted or unsubstituted (3- to 30-membered)heteroarylene; with the proviso that when $R_2$ is linked to adjacent $R_{11}$ to form a fused ring(s), $L_2$ represents a single bond;

$Y_1$ represents a single bond, —O—, —S—, —N—$Ar_1$, —$R_{12}C=CR_{12'}$—, —$R_{13}R_{14}C$—$CR_{13'}R_{14'}$—, or —$CR_{15}R_{16}$; provided that when $L_1$ is linked to $Y_1$, $Y_1$ represents —N—;

$Ar_1$ represents a substituted or unsubstituted (C6-C30)aryl or a substituted or unsubstituted (3- to 30-membered) heteroaryl;

$R_{12}$ to $R_{16}$, $R_{12'}$, $R_{13'}$, and $R_{14'}$ each independently represent hydrogen, a substituted or unsubstituted (C1-C30)alkyl, a substituted or unsubstituted (C6-C30)aryl, or a substituted or unsubstituted (3- to 30-membered) heteroaryl; or may be linked to an adjacent substituent to form a ring(s);

m and n each independently represent an integer of 1 or 2; and when m and n are 2 or more, each of $L_1$ and $L_2$ may be the same or different.

In one embodiment, A ring and B ring each independently may be a substituted or unsubstituted (C6-C30)aryl or a substituted or unsubstituted (3- to 30-membered)heteroaryl, preferably, a substituted or unsubstituted (C6-C25)aryl or a substituted or unsubstituted (5- to 25-membered)heteroaryl, more preferably, a substituted or unsubstituted (C6-C18)aryl or a substituted or unsubstituted (5- to 18-membered)heteroaryl. For example, A ring and B ring each independently may be benzene ring, naphthalene ring, carbazole ring, dibenzofuran ring, dibenzothiophene ring, or spirobifluorene ring.

According to one embodiment,

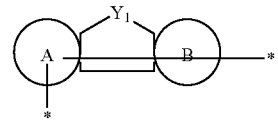

in the formula (1) may be represented by any one of the following formulas 1-1 to 1-13.

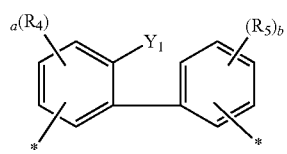
(1-1)

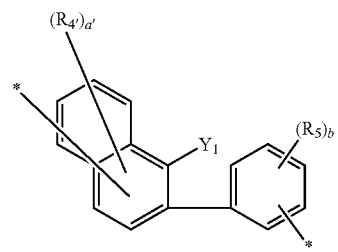
(1-2)

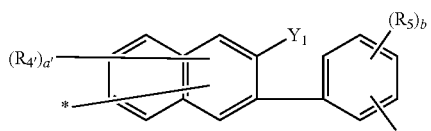
(1-3)

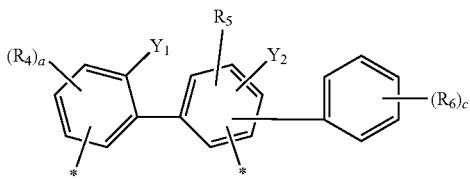
(1-4)

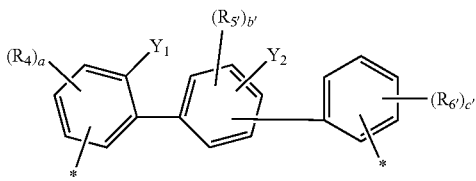
(1-5)

-continued

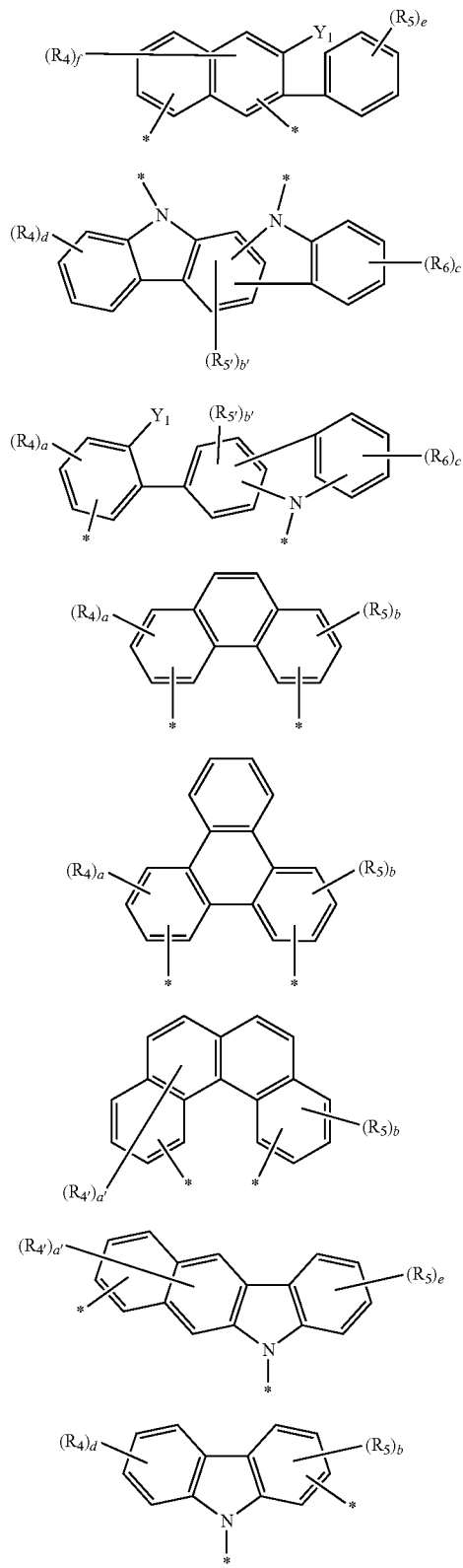

(1-6)
(1-7)
(1-8)
(1-9)
(1-10)
(1-11)
(1-12)
(1-13)

In formulas 1-1 to 1-13, $Y_2$ represents —O—, —S—, —N—$Ar_1$, or —$CR_{15}R_{16}$;

$Y_1$, $Ar_1$, $R_{15}$ and $R_{16}$ are as defined in formula 1;

$R_4$ to $R_6$ and $R_{4'}$ to $R_{6'}$ each independently are as defined as $R_2$ in formula 1;

a, b, and c' each independently represent an integer of 1 to 3, c to f each independently represent an integer of 1 to 4, a' represents an integer of 1 to 5, and b' represents an integer of 1 or 2; and when a to f and a' to c' are 2 or more, each of $R_{4'}$ to $R_{6'}$ and each of $R_4$ to $R_6$ may be the same or different.

According to another embodiment,

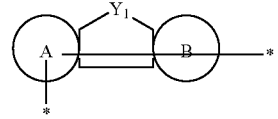

in the formula (1) may be represented by any one of the following formulas 1-14 to 1-30.

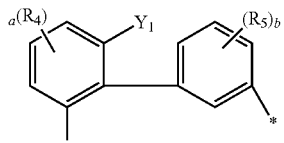
(1-14)

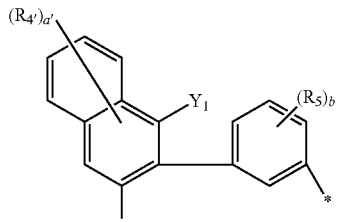
(1-15)

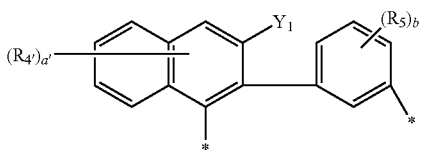
(1-16)

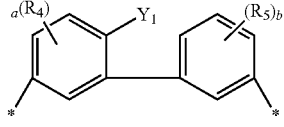
(1-17)

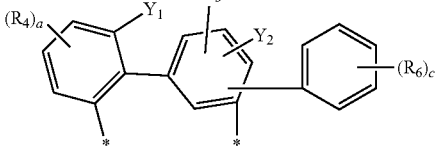
(1-18)

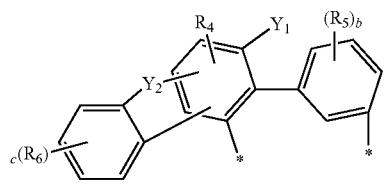
(1-19)

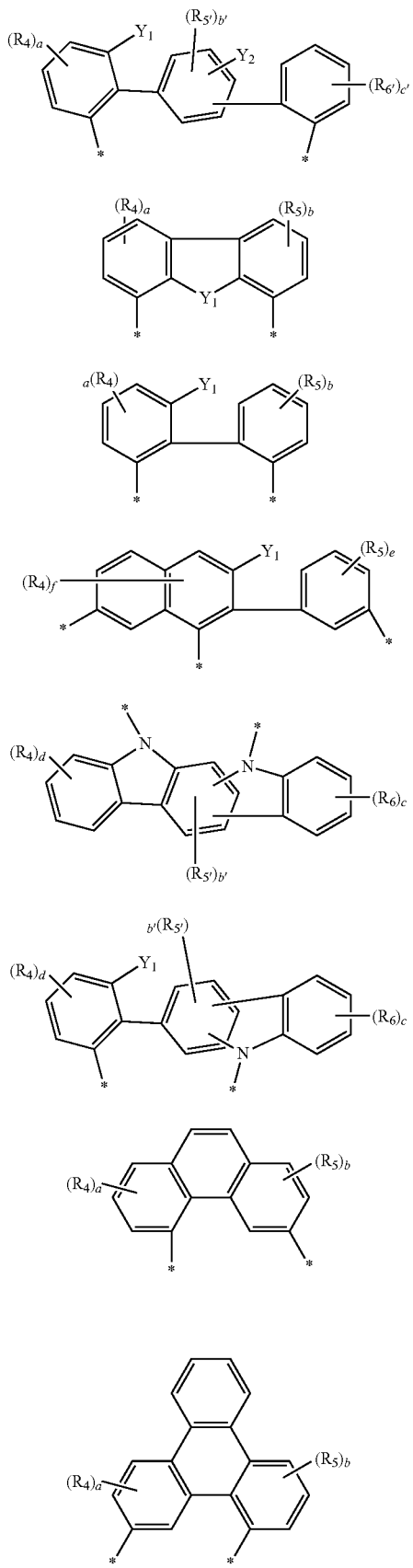

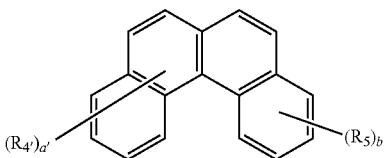

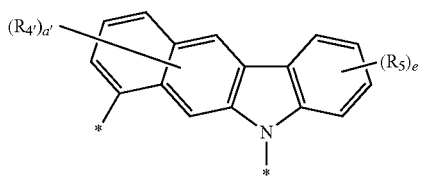

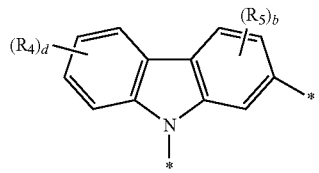

In formulas 1-14 to 1-30,
Y₂ represents —O—, —S—, —N—Ar₁, or —CR₁₅R₁₆;
R₄ to R₆, R₄' to R₆', Y₁, Ar₁, R₁₅, R₁₆, a to f, and a' to c' are as defined in formulas 1-1 to 1-13.

In one embodiment, $X_1$ to $X_3$ each independently represent N or $CR_{11}$, preferably, at least one of $X_1$ to $X_3$ may be N, more preferably, at least two of $X_1$ to $X_3$ may be N, even more preferably, $X_1$ to $X_3$ may be all N or may be all $CR_{11}$.

In one embodiment, $R_2$ and Ru each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of an (C3-C30) aliphatic ring and an (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or adjacent $R_2$ and Ru may be linked to each other to form a substituted or unsubstituted (5- to 30-membered) mono- or polycyclic, alicyclic, aromatic ring, or a combination thereof, more preferably, hydrogen, a substituted or unsubstituted (C6-C18)aryl, or a substituted or unsubstituted (5- to 18-membered)heteroaryl; or adjacent $R_2$ and $R_{11}$ may be linked to each other to form a (5- to 25-membered) polycyclic, alicyclic, aromatic ring, or a combination thereof. When $R_2$ is linked to adjacent $R_{11}$ to form a fused ring(s), $L_2$ represents a single bond. For example, $R_2$ and $R_{11}$ each independently may be hydrogen, phenyl unsubstituted or substituted with at least one of (C6-C30)aryl and (5- to 30-membered) heteroaryl, a substituted or unsubstituted m-biphenyl, a substituted or unsubstituted p-biphenyl, a substituted or unsubstituted p-terphenyl, a substituted or unsubstituted m-terphenyl, a substituted or unsubstituted fluorenyl, a substituted or unsubstituted spirobifluorenyl, a substituted or unsubstituted triphenylenyl, a substituted or unsubstituted chrysenyl, a substituted or unsubstituted pyrimidyl, a substituted or unsubstituted triazinyl, a substituted or unsubstituted dibenzofuranyl, a substituted or unsubstituted dibenzothiophenyl, or a substituted or unsubstituted carbazolyl; or may be linked each other to form a substituted or unsubstituted (5- to 30-membered) mono- or polycyclic, aromatic ring. In addition, the formed ring may contain at least one heteroatom selected from the group consisting of B, N, O, S, Si, and P, preferably, N, O, and S, more preferably, at least one nitrogen (N). For example, $R_2$ may be linked to adjacent Ru to form a substituted or unsubstituted isoquinolinyl, a substituted or unsubstituted quinoxalinyl, a substituted or unsubstituted quinazolinyl, a substituted or unsubstituted naphthyridinyl, a substituted or unsubstituted phenanthroquinoxalinyl, a substituted or unsubstituted benzothienoquinazolinyl, a substituted or unsubstituted benzofuroquinazolinyl, or a substituted or unsubstituted dimethylindenoquinazolinyl.

According to one embodiment, the organic electroluminescent compound of formula 1 may be represented by the following formula 2-1 or 2-2.

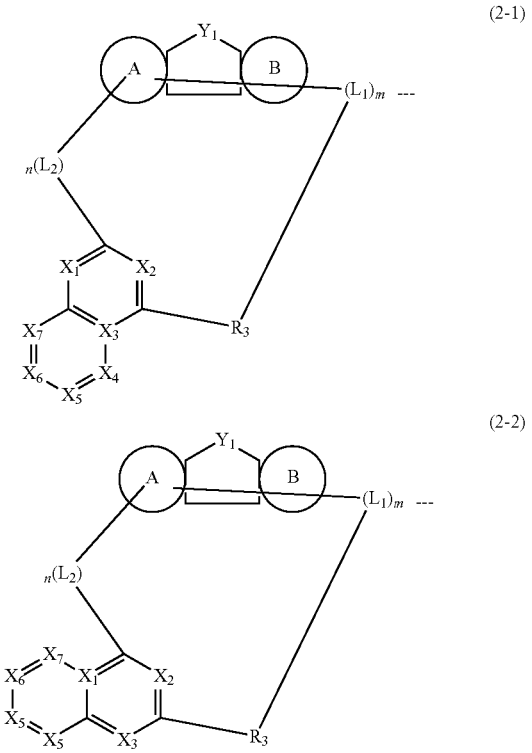

In formulas 2-1 and 2-2,
A ring, B ring, $Y_1$, $R_3$, $X_1$ to $X_3$, $L_1$, and $L_2$, m, and n are as defined in formula 1; and
$X_4$ to $X_7$ each independently are as defined as $X_1$ to $X_3$ in formula 1.

In one embodiment, $L_1$, $L_2$, and $R_3$ each independently represent a single bond, a substituted or unsubstituted (C6-C30)arylene, or a substituted or unsubstituted (3- to 30-membered)heteroarylene, preferably, may be a single bond, a substituted or unsubstituted (C6-C30)arylene, or a substituted or unsubstituted (5- to 30-membered)heteroarylene, more preferably a single bond, a substituted or unsubstituted (C6-C25)arylene, or a substituted or unsubstituted (5- to 25-membered)heteroarylene. For example, $L_1$, $L_2$, and $R_3$ each independently may be a single bond, phenylene unsubstituted or substituted with at least one of phenyl, biphenyl, triphenylenyl, fluorenyl, spirobifluorenyl, dibenzofuranyl, and dibenzothiophenyl, a substituted or unsubstituted triphenylenylene, a substituted or unsubstituted biphenylene, a substituted or unsubstituted terphenylene, a substituted or unsubstituted spirobifluorenylene, or a substituted or unsubstituted dibenzofuranylene.

In one embodiment, $Y_1$ represents a single bond, —O—, —S—, —N—$Ar_1$, —$R_{12}$C=$CR_{12'}$—, —$R_{13}R_{14}$C—$CR_{13'}R_{14'}$—, or —$CR_{15}R_{16}$; provided that when $L_1$ is linked to $Y_1$, $Y_1$ represents —N—, where $Ar_1$ represents a substituted or unsubstituted (C6-C30)aryl or a substituted or unsubstituted (3- to 30-membered)heteroaryl, preferably may be a substituted or unsubstituted (C6-C25)aryl or a substituted or unsubstituted (5- to 25-membered)heteroaryl, more preferably a substituted or unsubstituted (C6-C18)aryl or a substituted or unsubstituted (5- to 18-membered)heteroaryl; $R_{12}$ to $R_{16}$, $R_{12'}$, $R_{13'}$, and $R_{14'}$ each independently may be hydrogen, a substituted or unsubstituted (C1-C30) alkyl, a substituted or unsubstituted (C6-C30)aryl, or a substituted or unsubstituted (3- to 30-membered)heteroaryl; or may be linked to the adjacent substituent to form a ring(s), preferably, hydrogen, a substituted or unsubstituted (C1-C20)alkyl, or a substituted or unsubstituted (C6-C25)aryl; may be linked to the adjacent substituent to form a substituted or unsubstituted (5- to 30-membered) mono- or polycyclic, alicyclic, aromatic ring, or a combination thereof, more preferably, hydrogen, a substituted or unsubstituted (C1-C10)alkyl, or a substituted or unsubstituted (C6-C18) aryl; or may be linked to the adjacent substituent a substituted or unsubstituted (5- to 25-membered) mono- or polycyclic, aromatic ring.

For example, $Ar_1$ may be a substituted or unsubstituted phenyl, a substituted or unsubstituted pyridyl, a substituted or unsubstituted dibenzofuranyl, or a substituted or unsubstituted carbazolyl.

For example, $R_{12}$ to $R_{16}$, $R_{12'}$, $R_{13'}$, and $R_{14'}$ each independently represent hydrogen, a substituted or unsubstituted methyl, or a substituted or unsubstituted phenyl; or may be linked to the adjacent substituent, e.g., the adjacent $R_{13}$, $R_{14}$, $R_{13'}$, and $R_{14'}$ or the adjacent $R_{15}$ and $R_{16}$, to form a substituted or unsubstituted (5- to 25-membered) polycyclic aromatic ring. Further, the formed ring may be included at least one heteroatom selected from the group consisting of N, O, and S.

According to one embodiment, the organic electroluminescent compound represented by formula 1 above may be more specifically illustrated by the following compounds, but is not limited thereto.

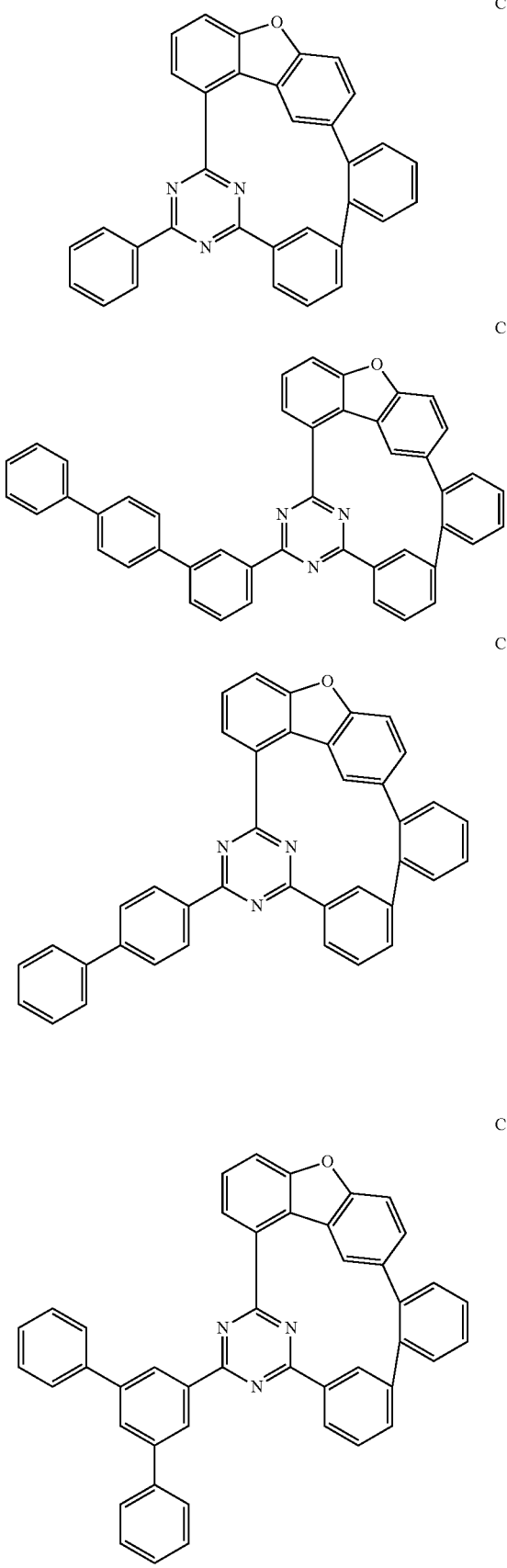
C-1
C-2
C-3
C-4
-continued
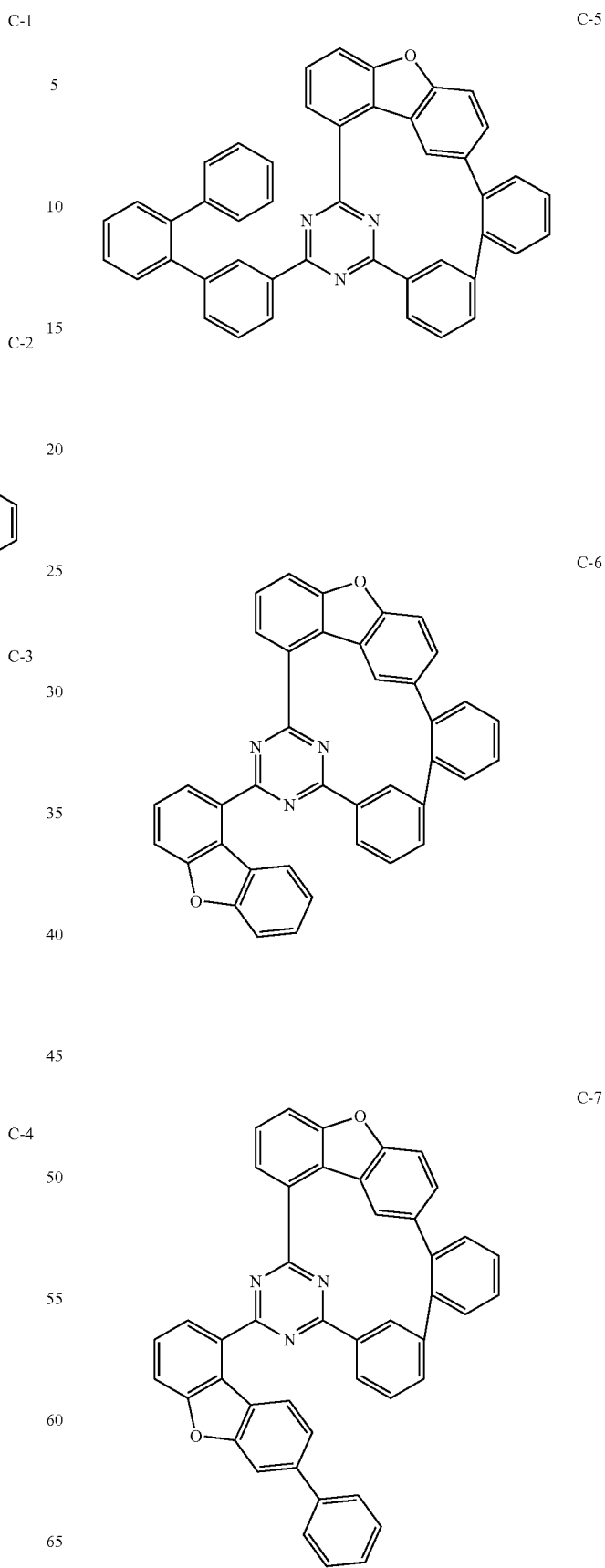
C-5
C-6
C-7

-continued
C-8
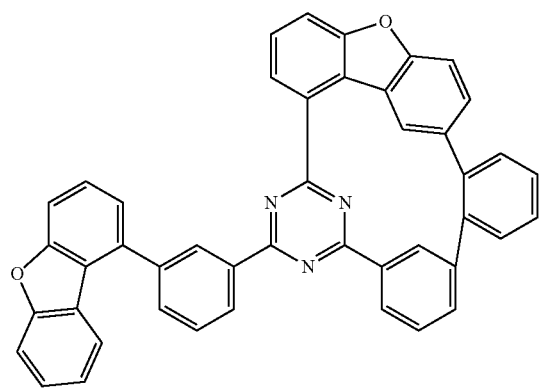
C-9
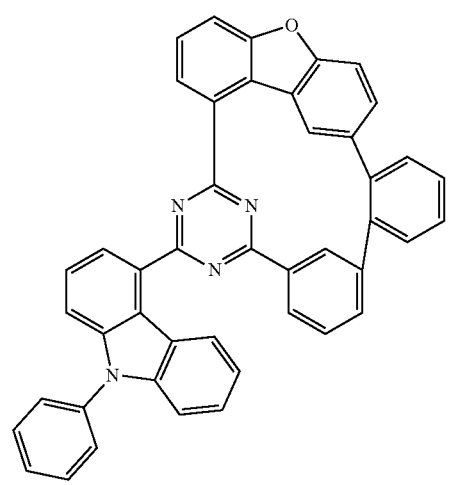
C-10
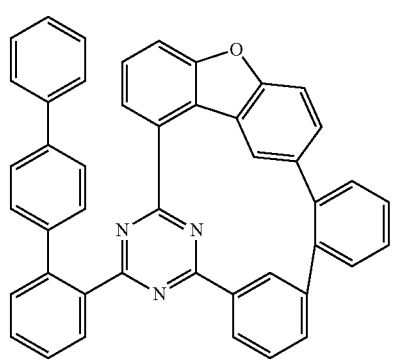
C-11
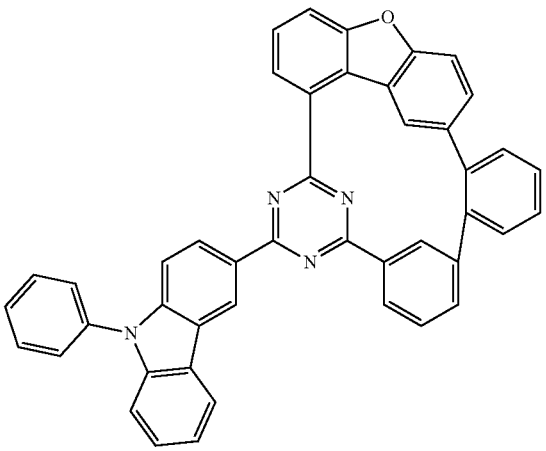
C-12
C-13
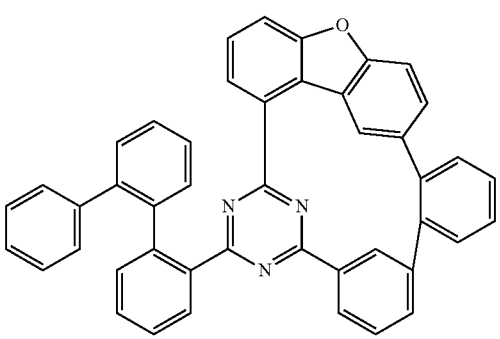

C-14
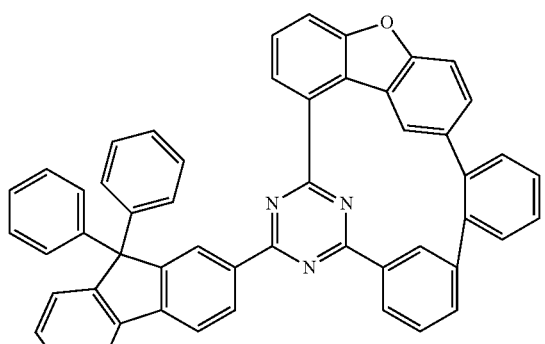
C-15
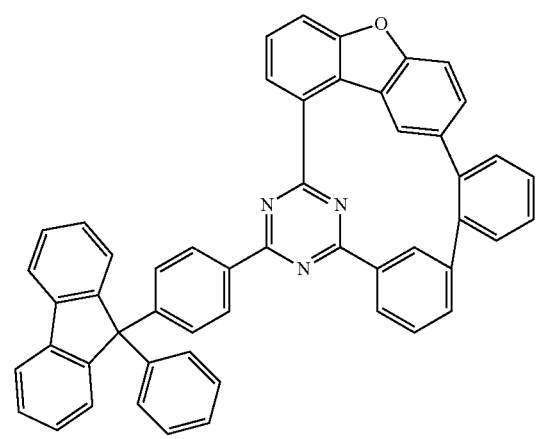
C-16
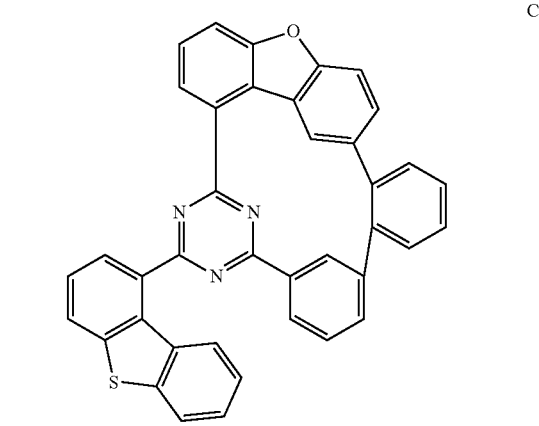
C-17
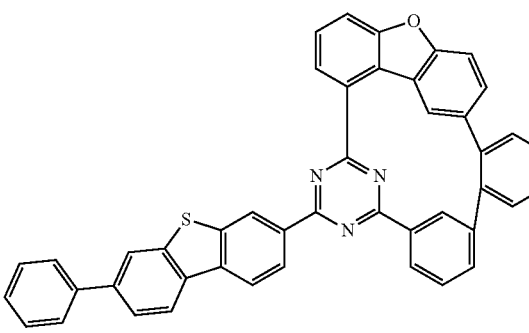
C-18
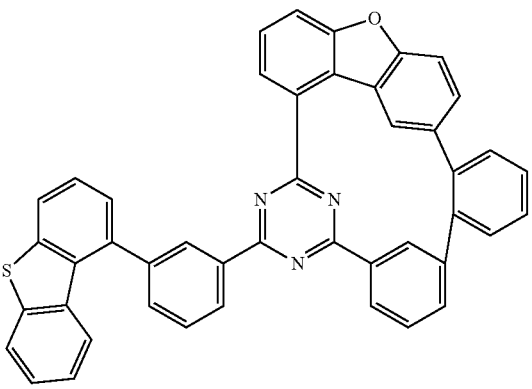
C-19
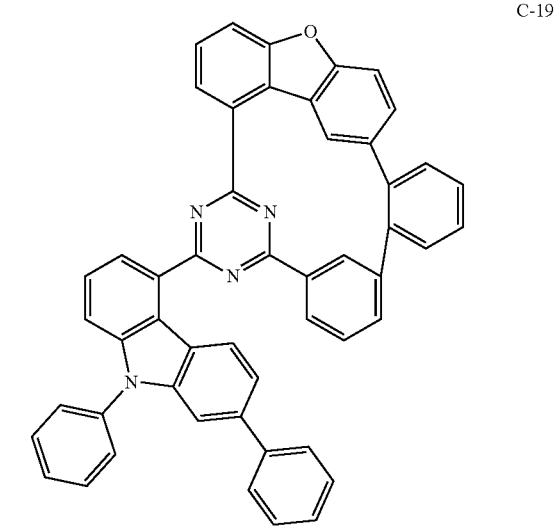
C-20
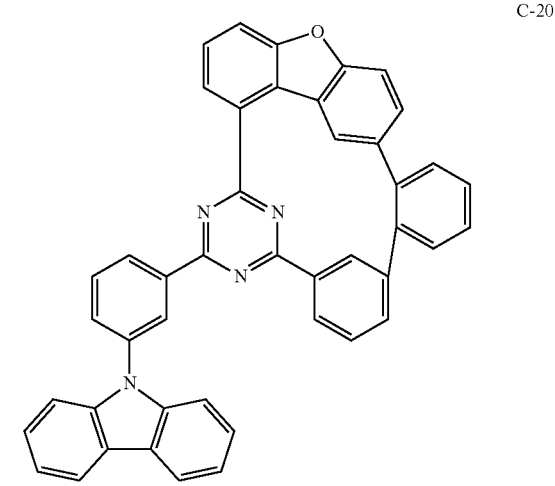

C-21
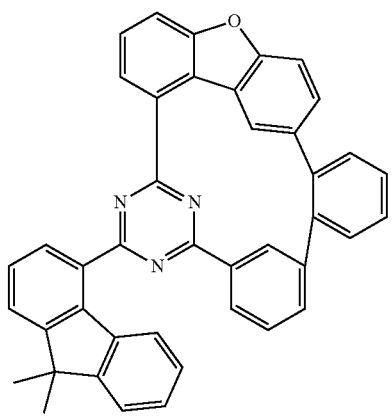
C-24
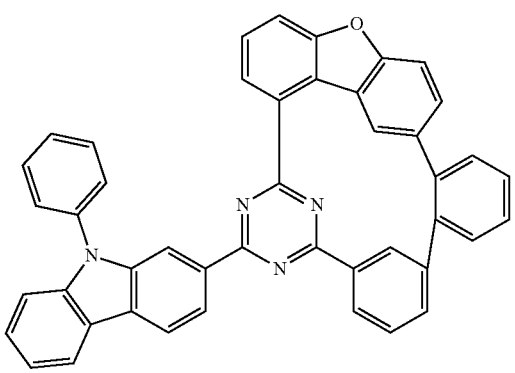
C-22
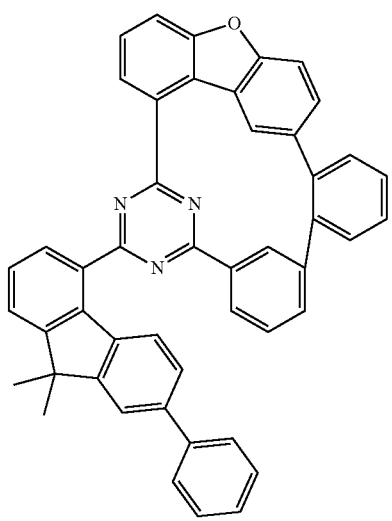
C-25
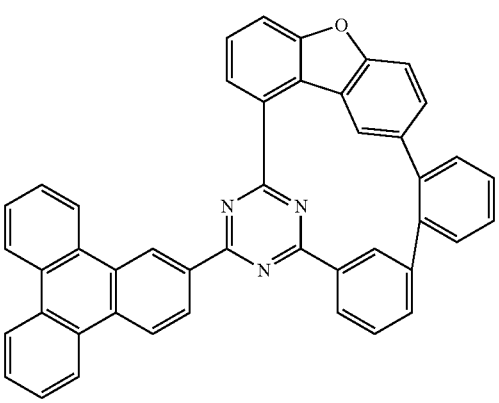
C-23
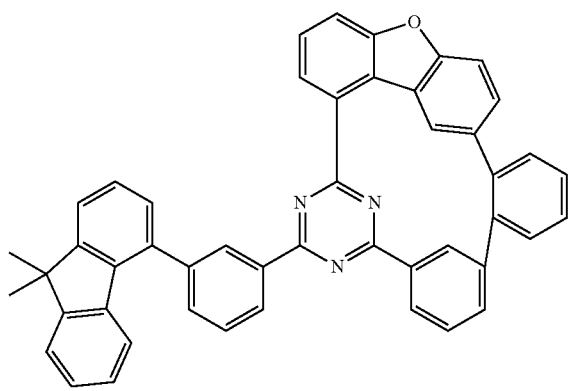
C-26
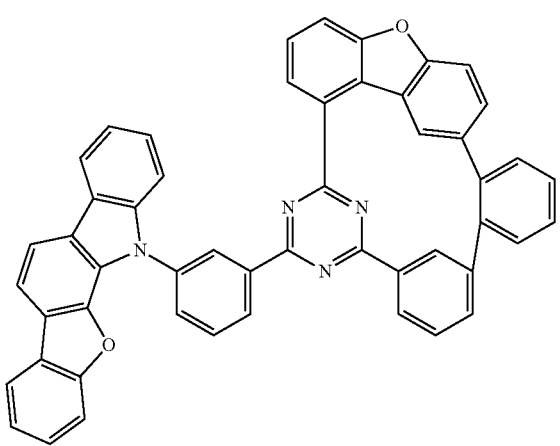

C-27
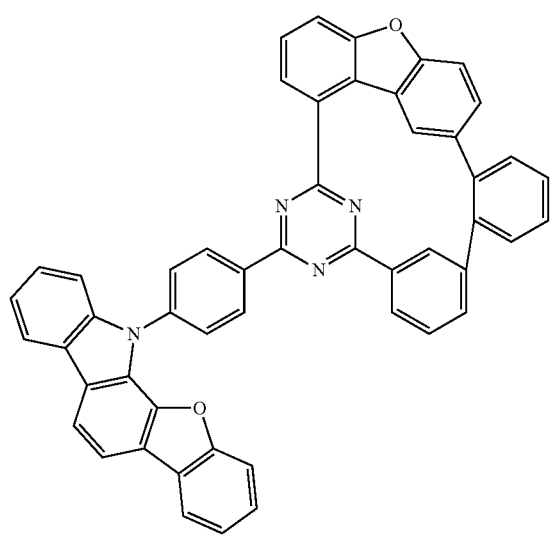
C-28
C-29
C-30
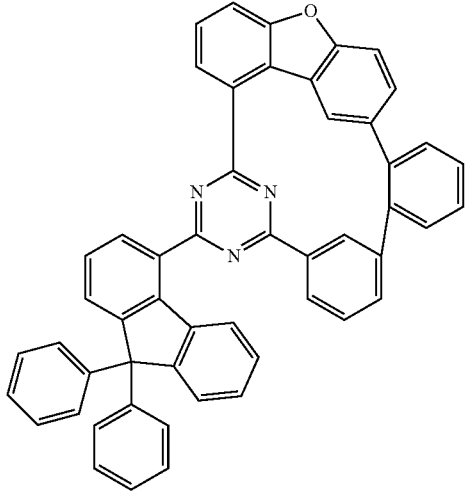
C-31
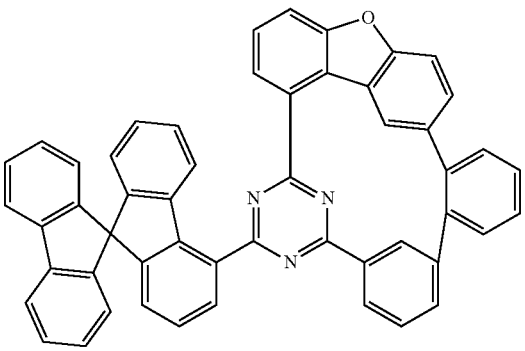
C-32
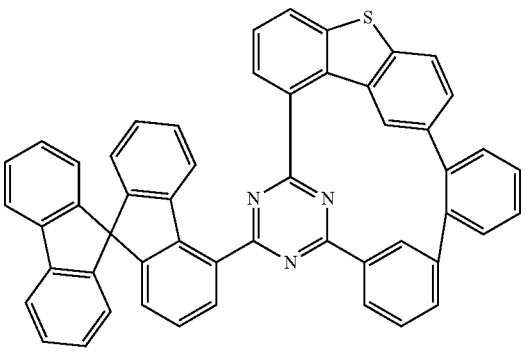
C-33
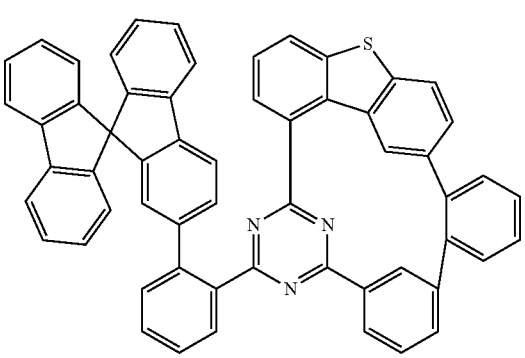

C-34
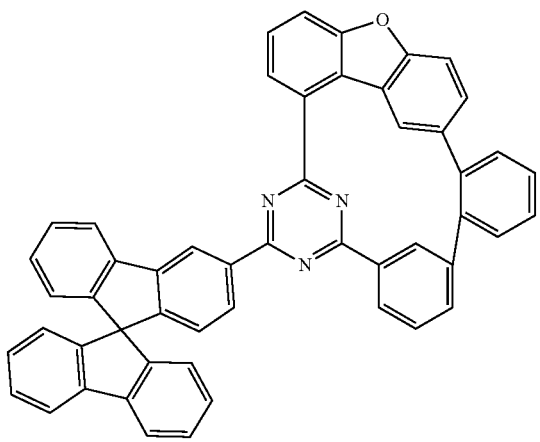
C-35
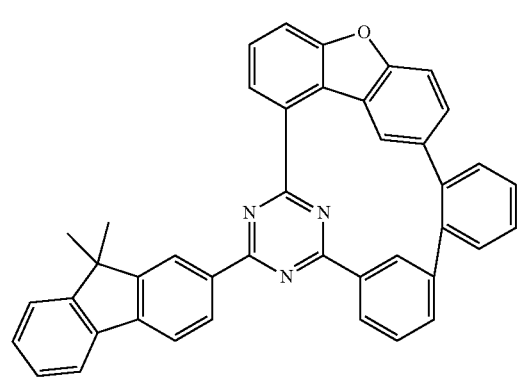
C-36
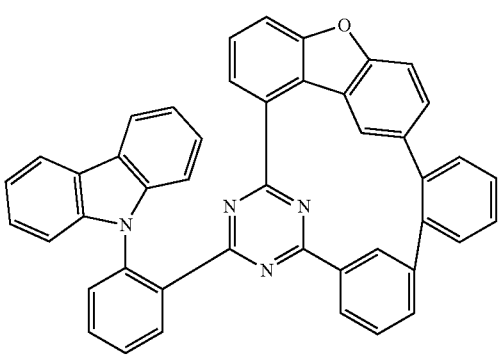
C-37
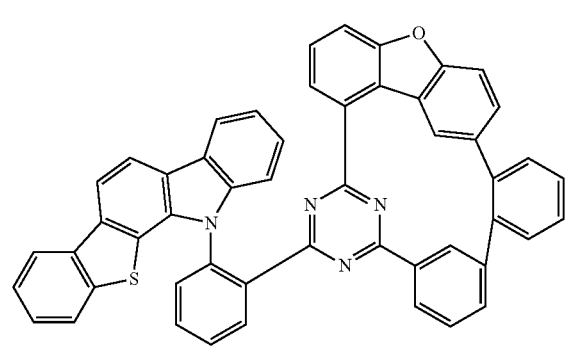
C-38
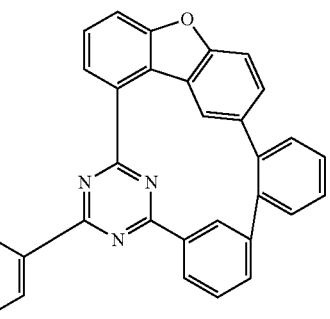
C-39
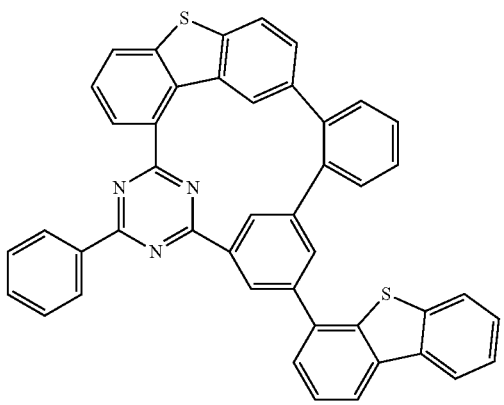
C-40
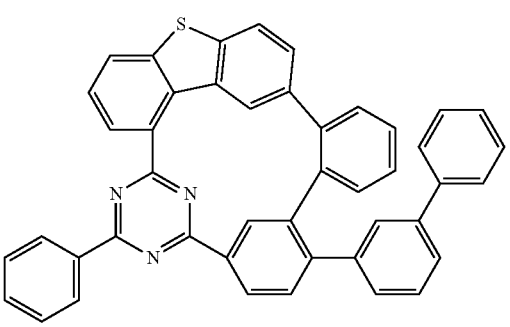
C-41
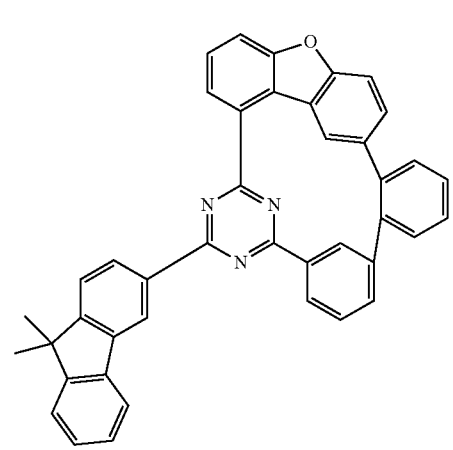

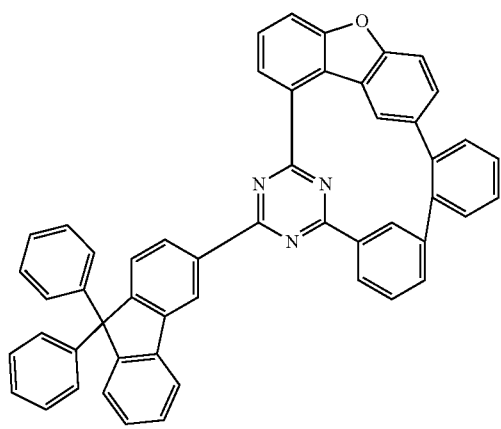
C-42
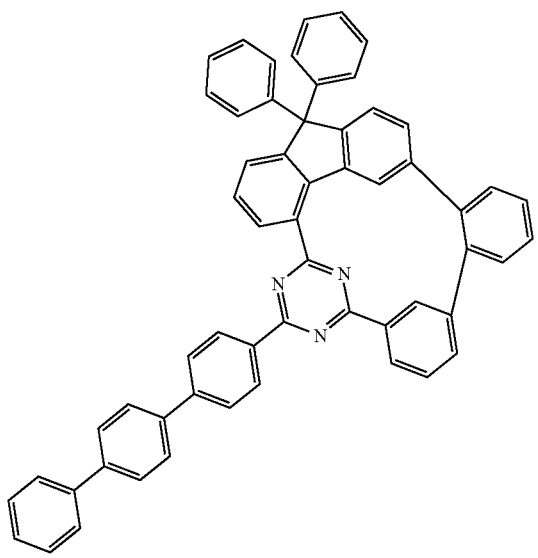
C-45
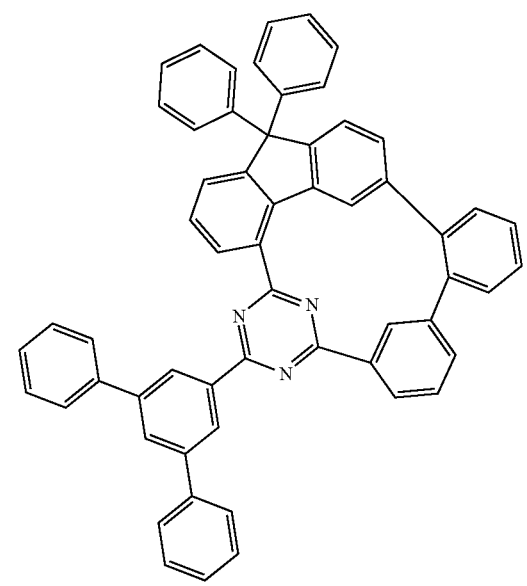
C-46
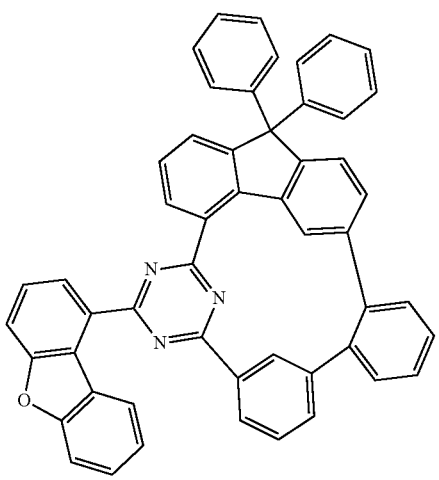
C-47
C-43
C-44

-continued
C-48
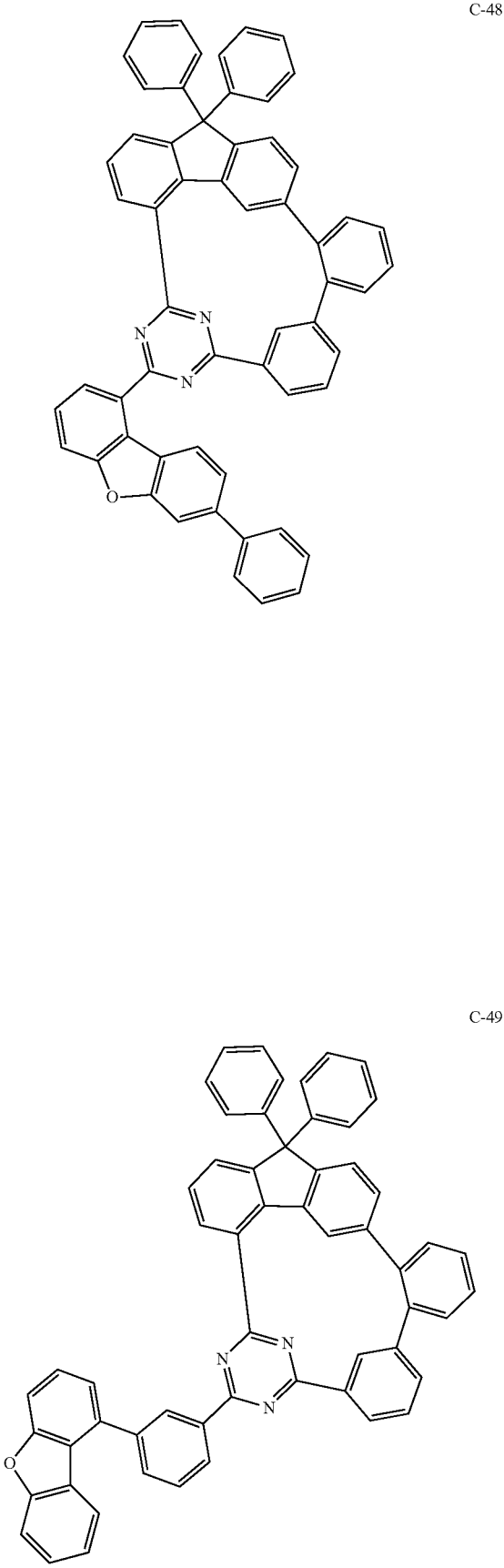
C-49
C-50
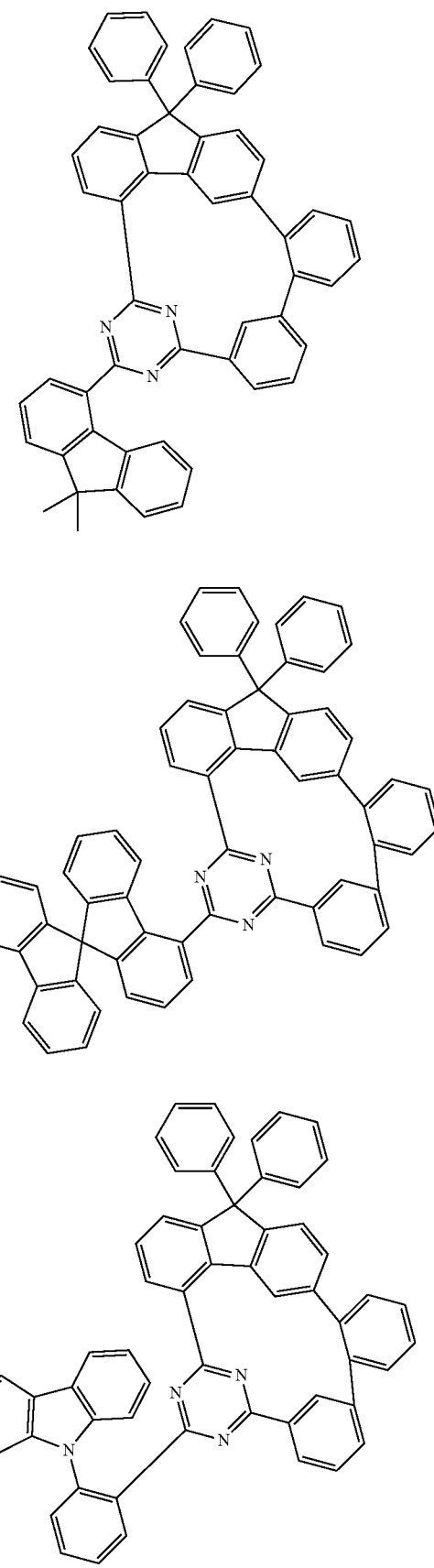
C-51
C-52

C-53
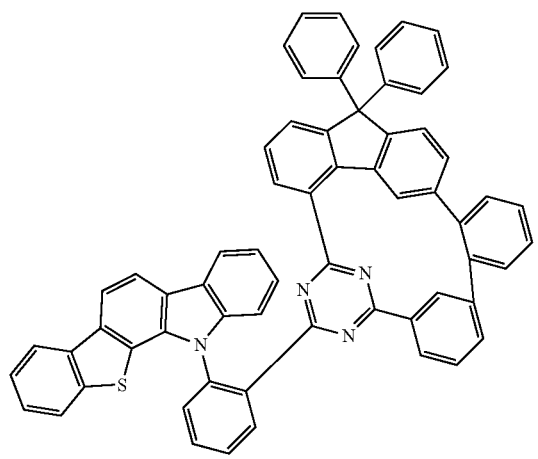
C-54
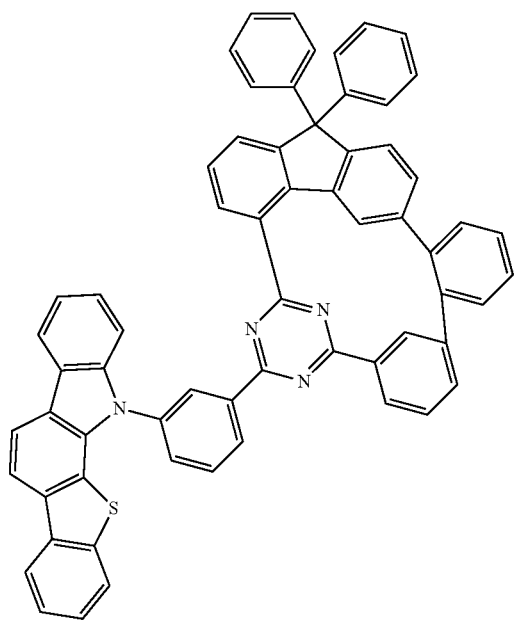
C-55
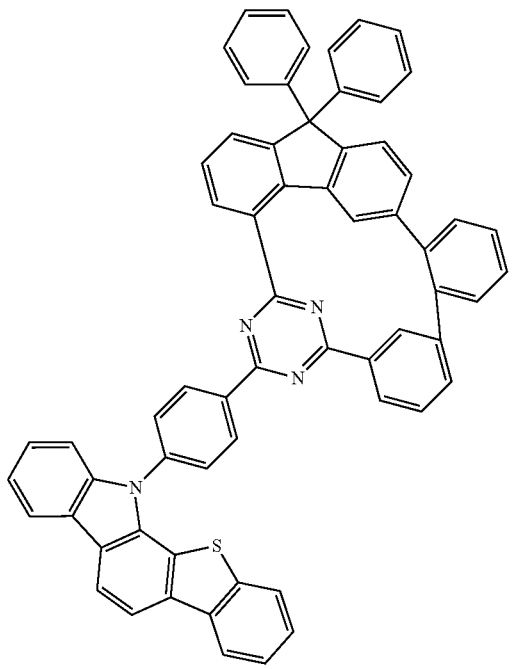
C-56
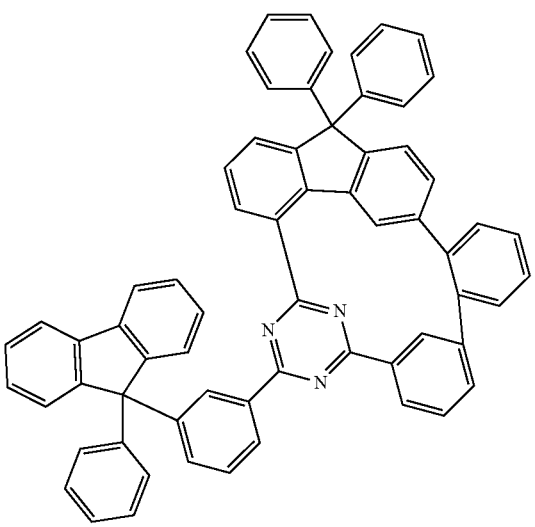

C-57
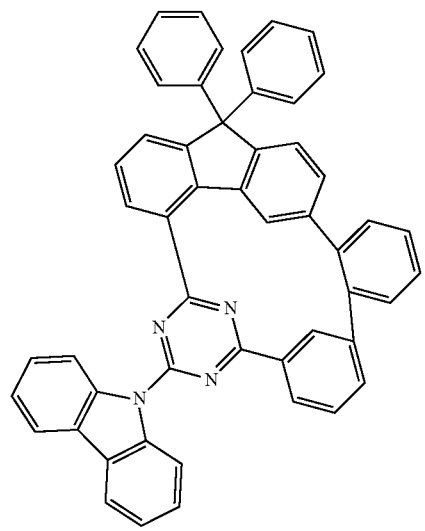
C-58
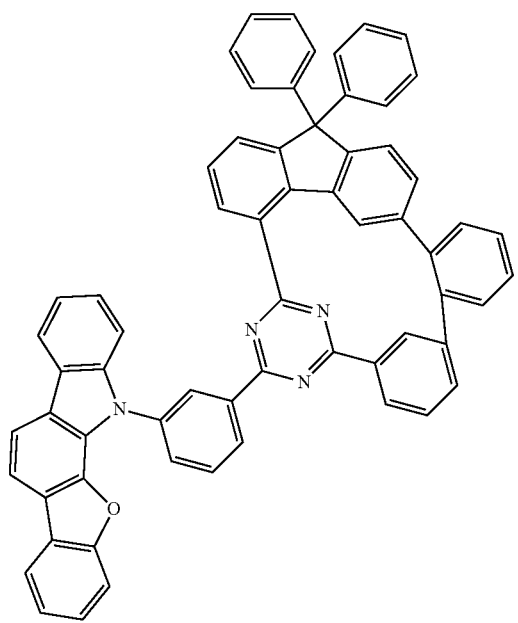
C-59
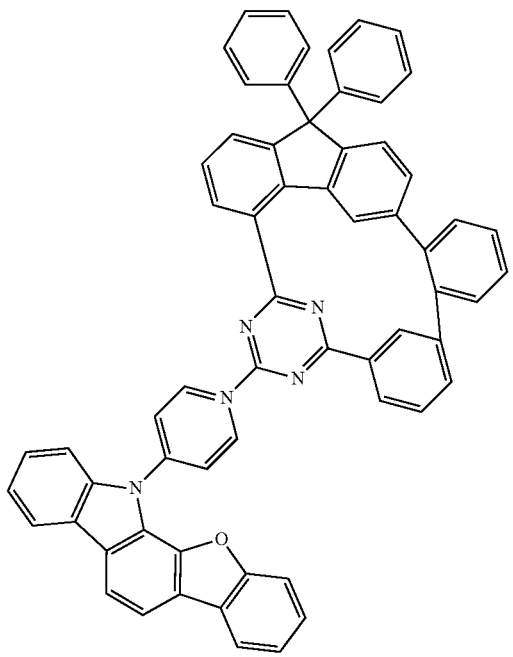
C-60
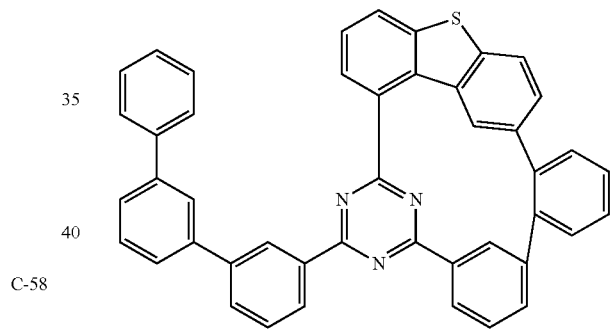
C-61
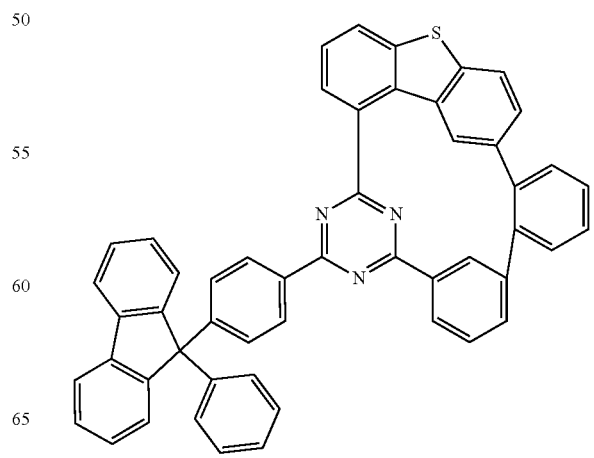

-continued
C-62
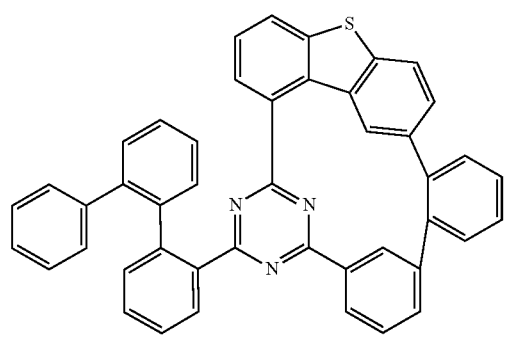
C-63
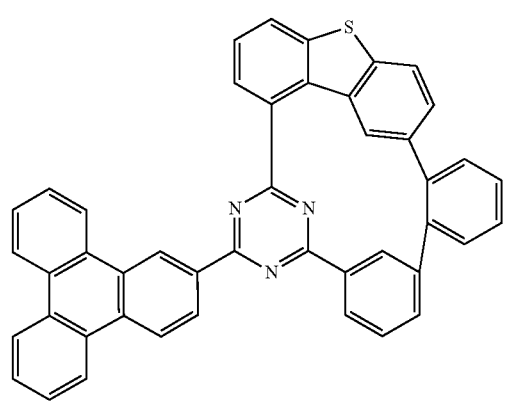
C-64
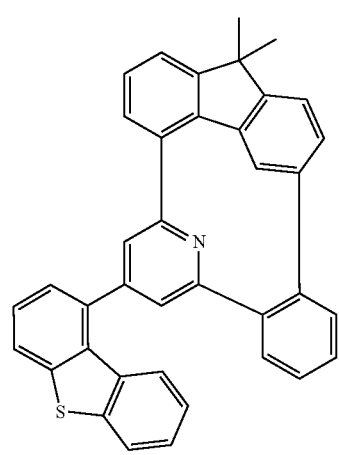
-continued
C-65
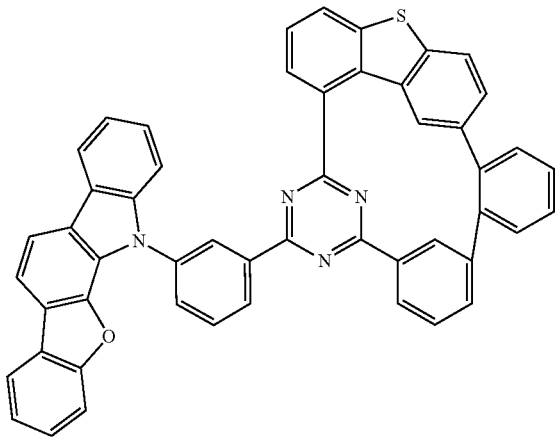
C-66
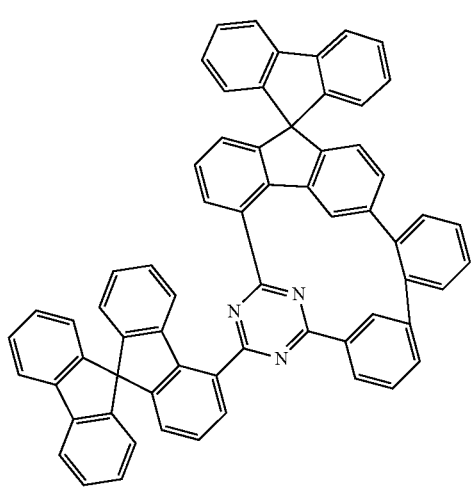
C-67
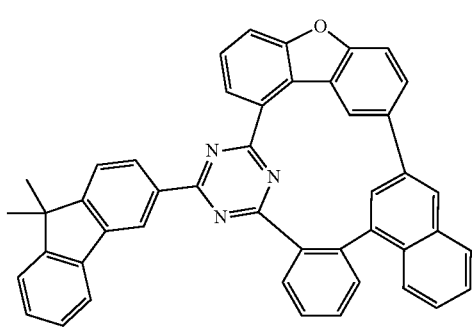

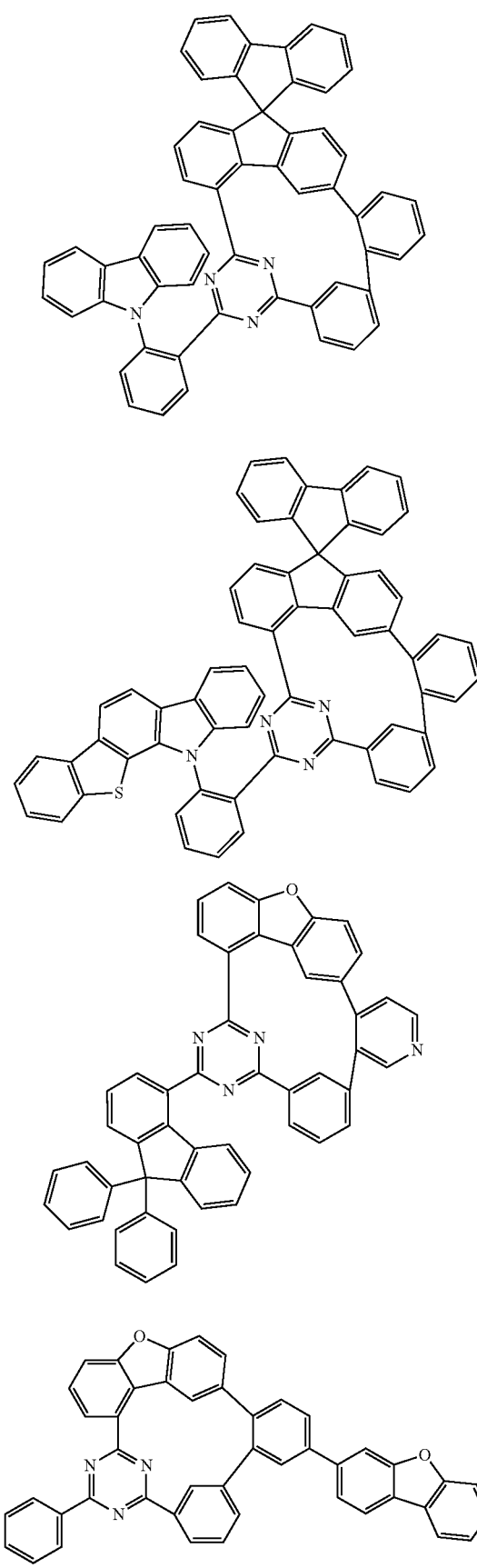
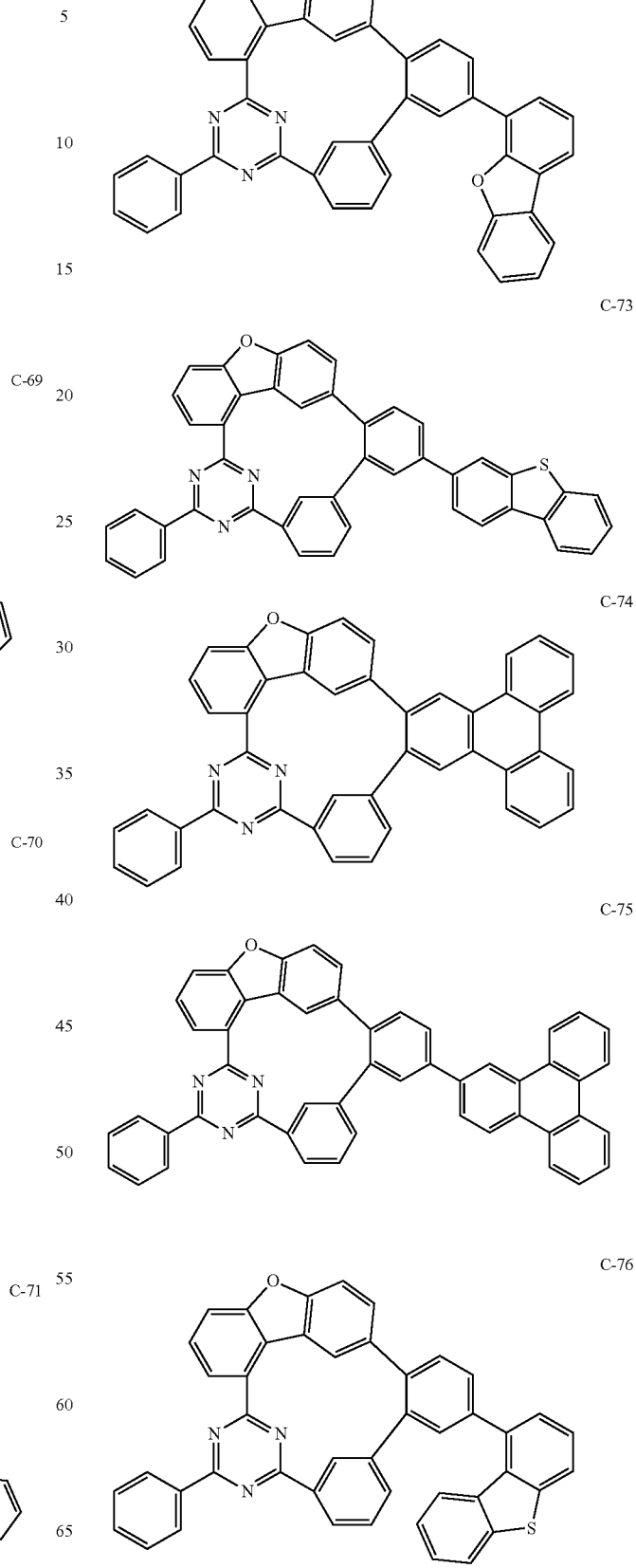

-continued
C-77
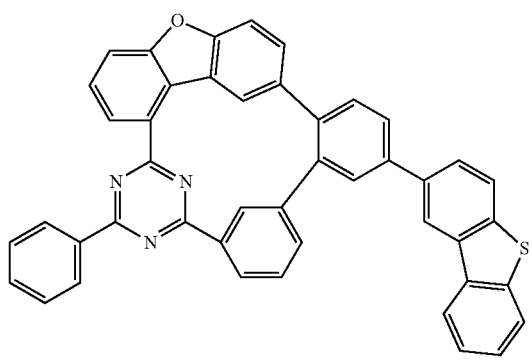
C-78
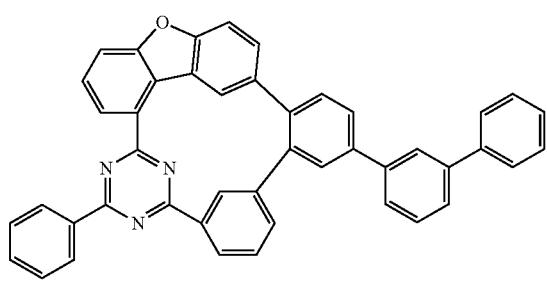
C-79
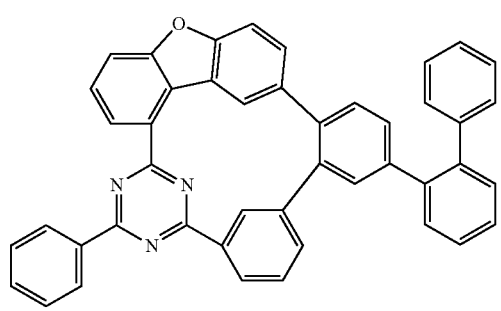
C-80
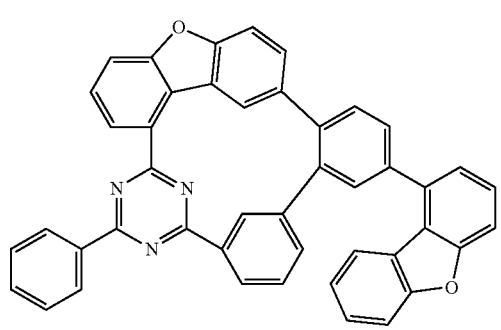
C-81
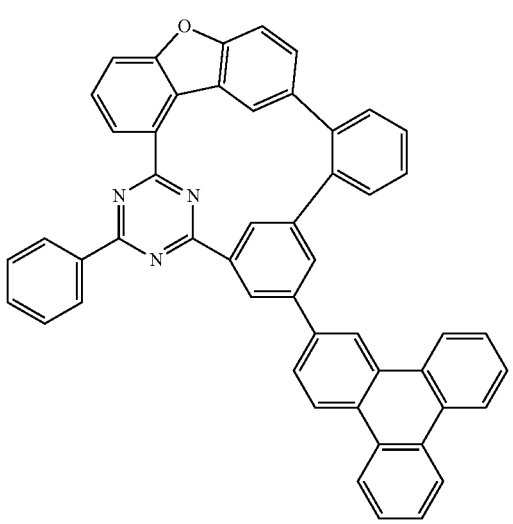
C-82
C-83
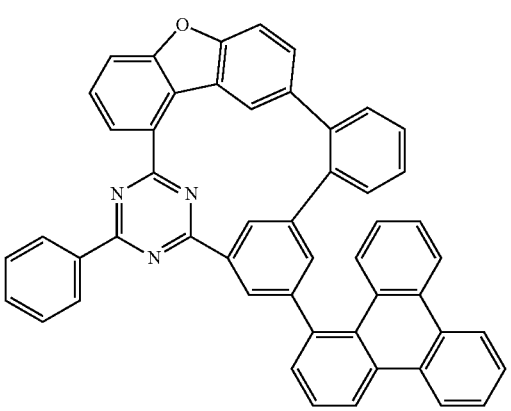

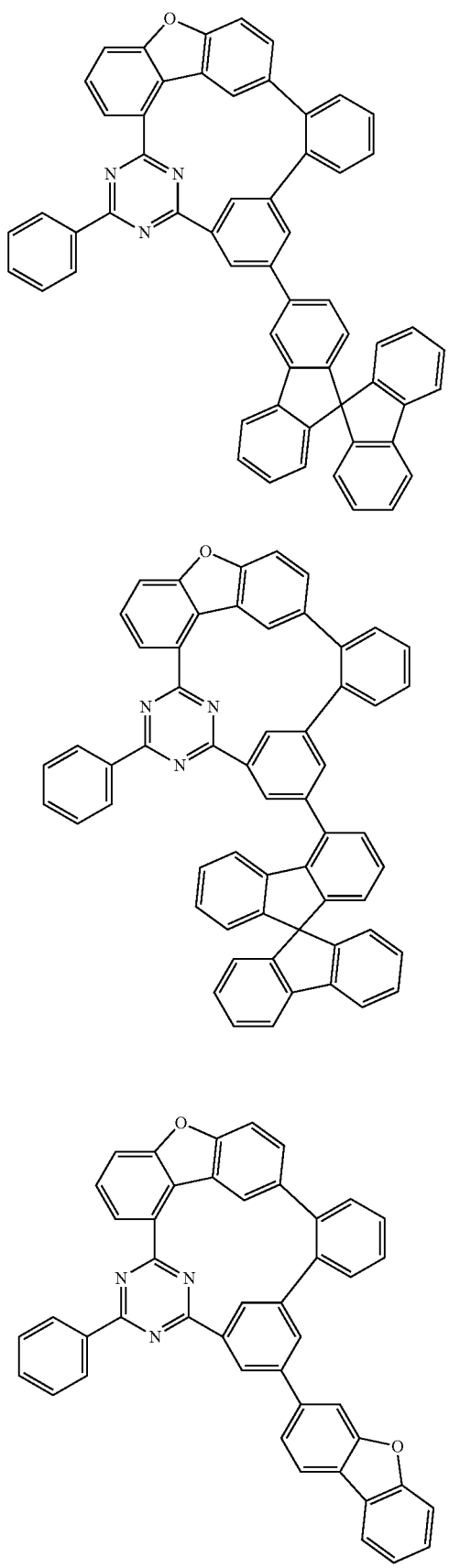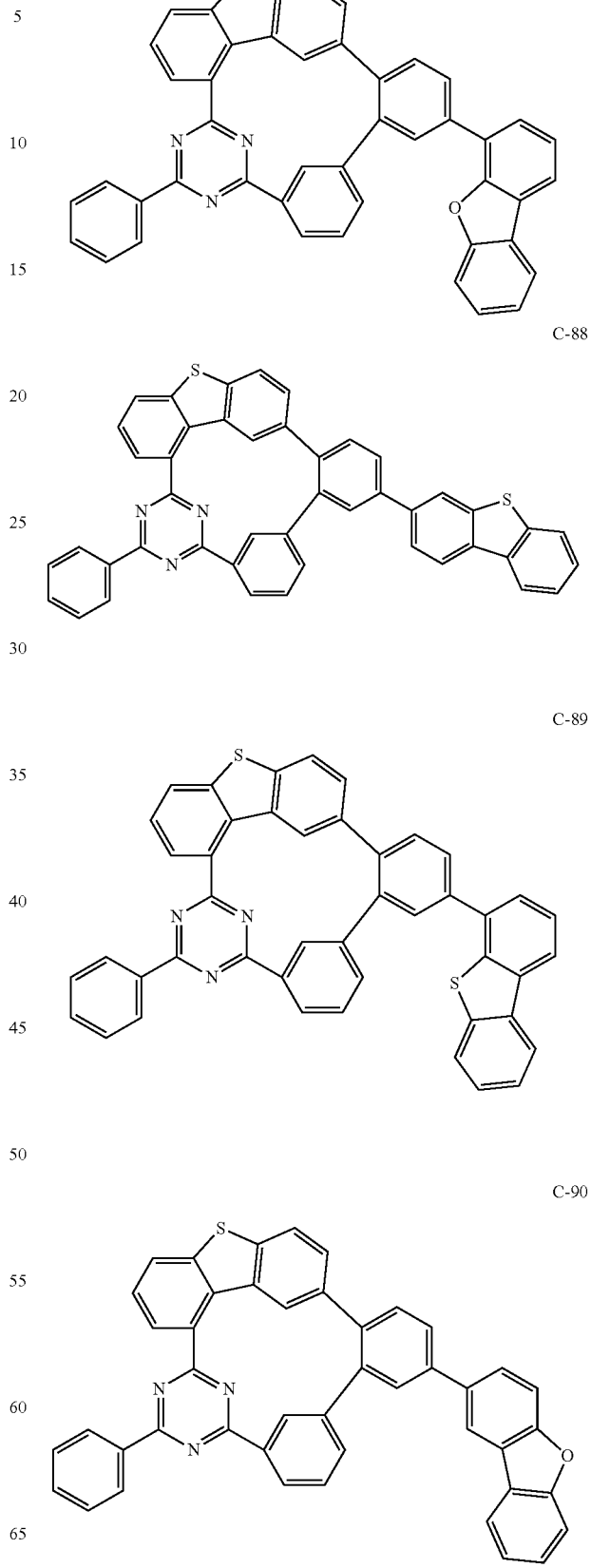

C-91
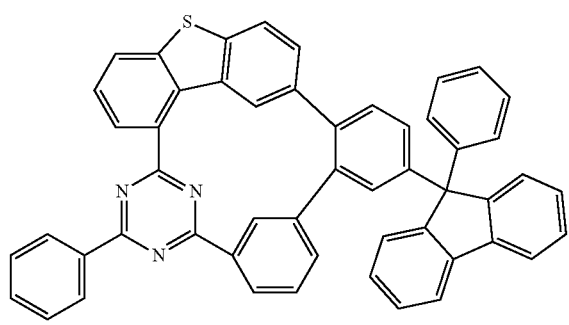
C-92
C-95
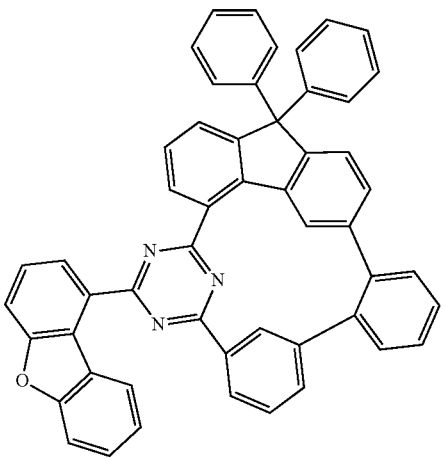
C-96
C-93
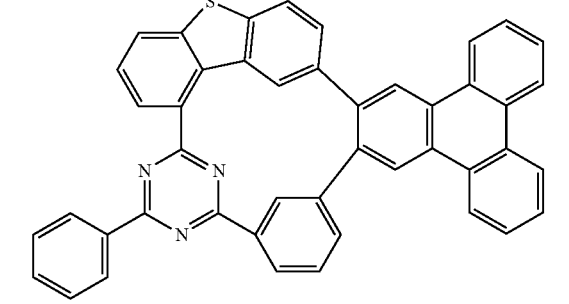
C-97
C-94
C-98
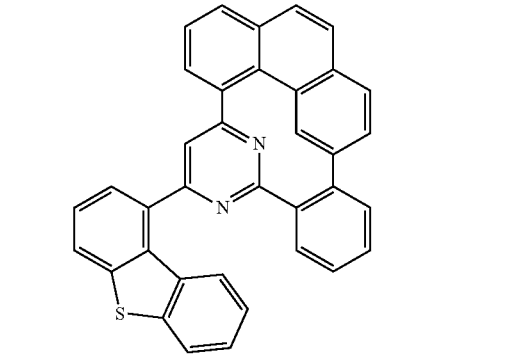

C-99
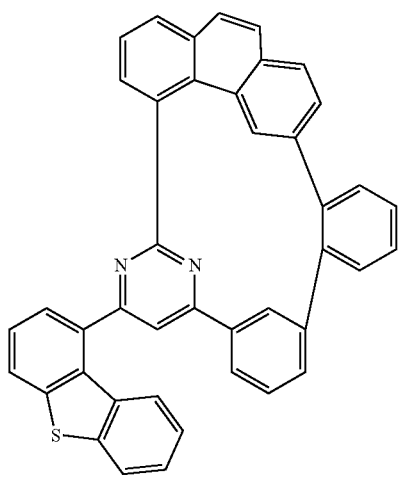
C-100
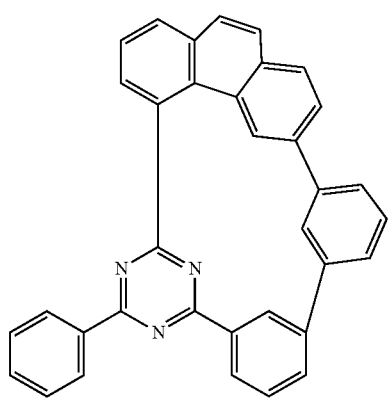
C-101
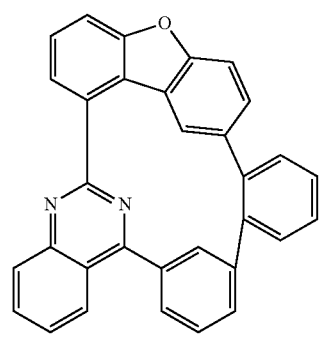
C-102
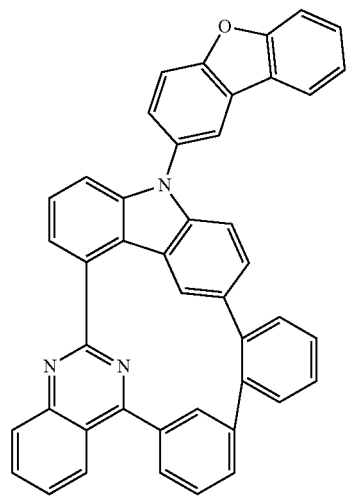
C-103
C-104
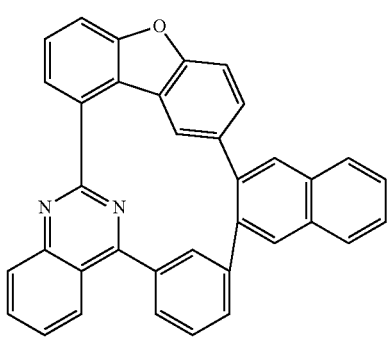

C-105
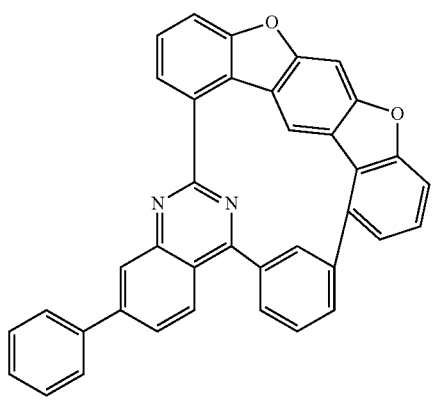
C-106
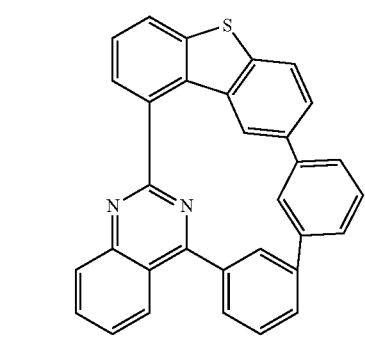
C-107
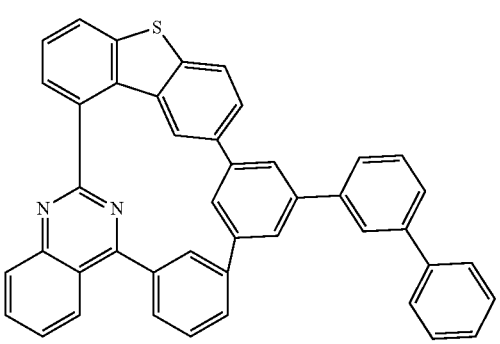
C-108
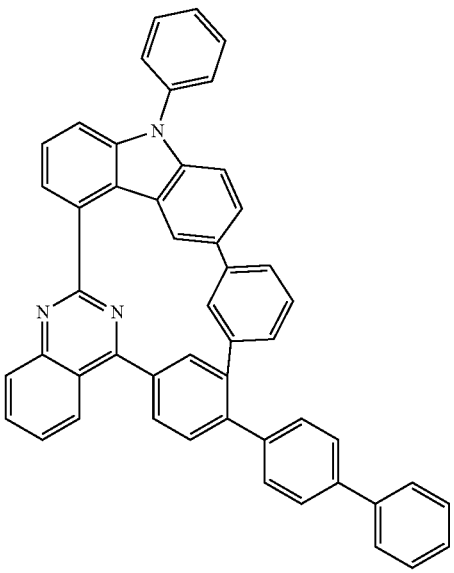
C-109
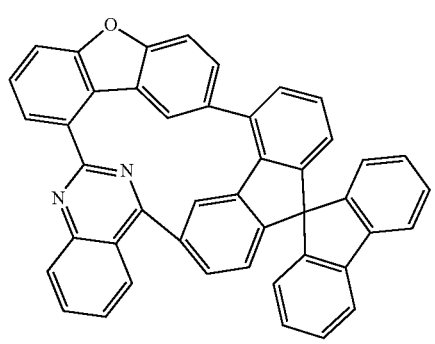
C-110
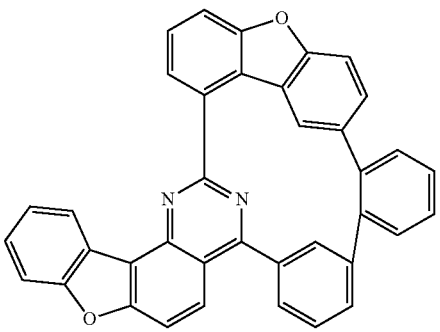
C-111
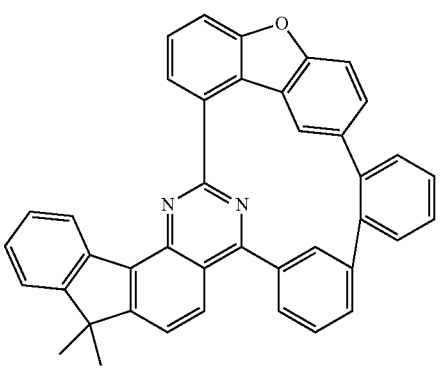
C-112

C-113
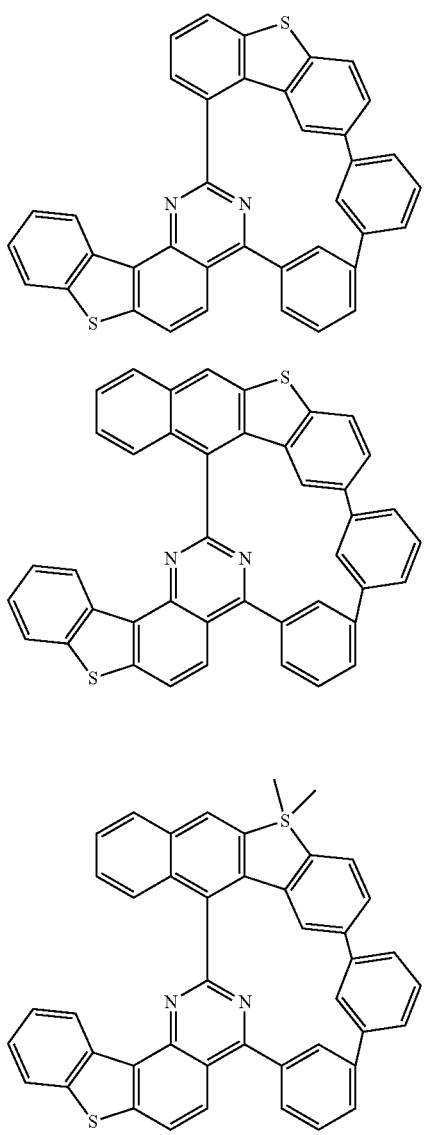
C-114
C-115
C-116
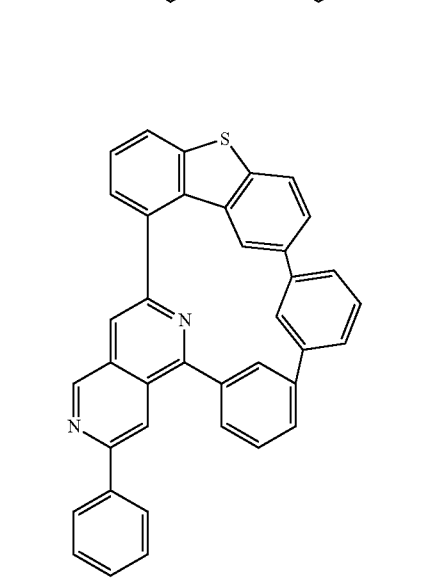
C-117
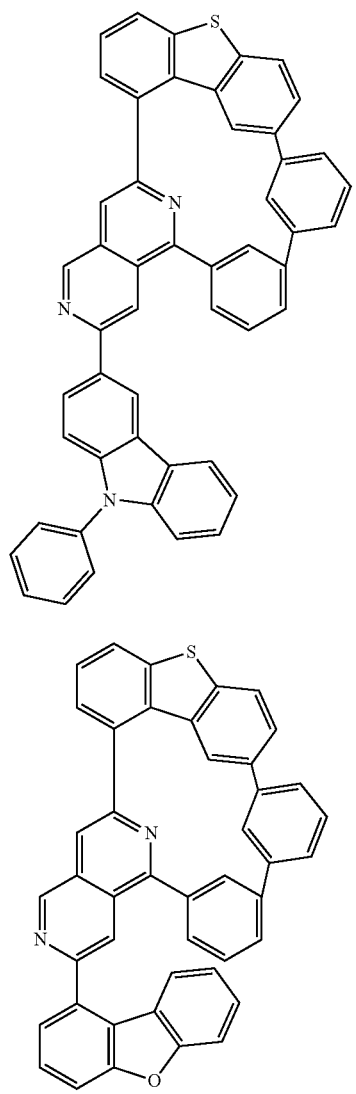
C-118
C-119
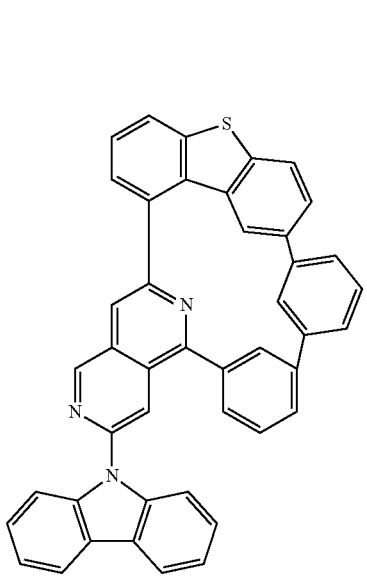

-continued
C-120
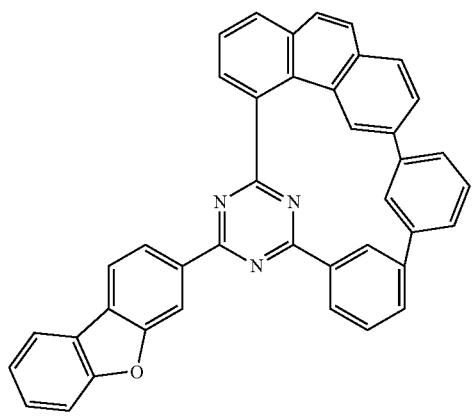
C-121
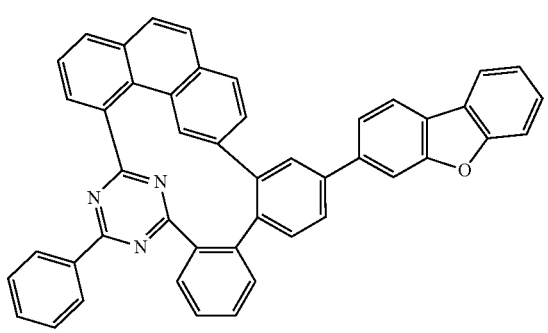
C-122
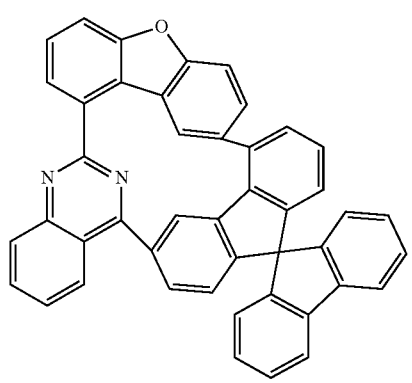
C-123
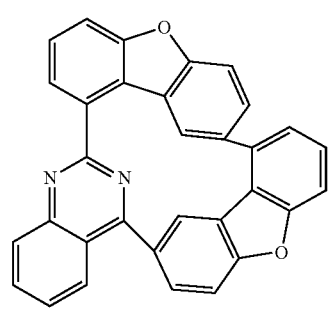
C-124
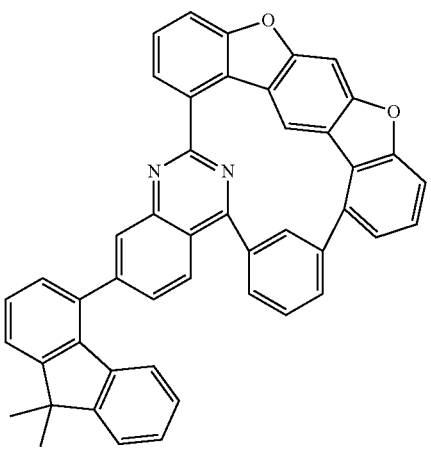
C-125
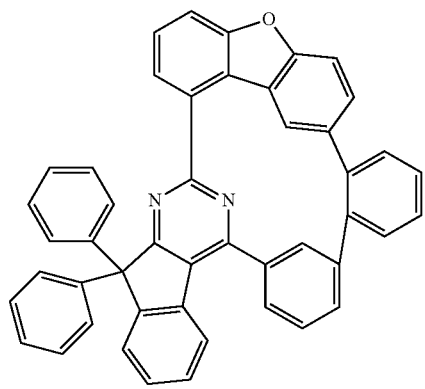
C-126
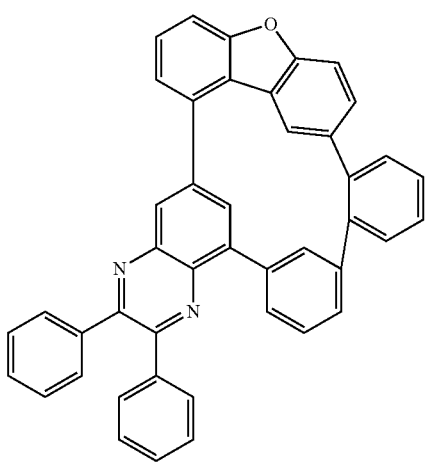

C-127
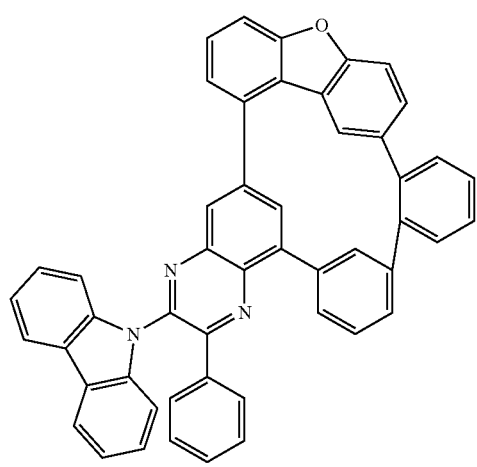
C-128
C-129
C-130
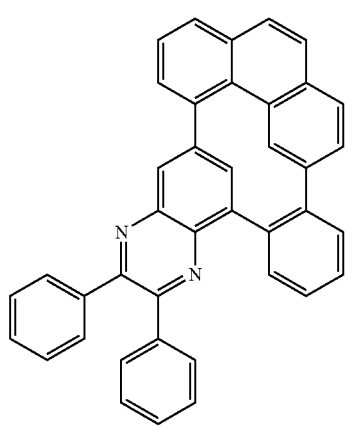
C-131
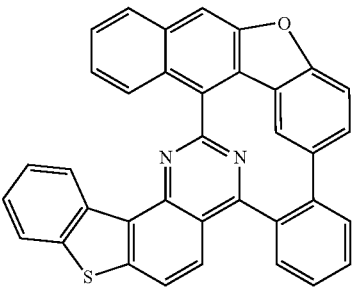
C-132
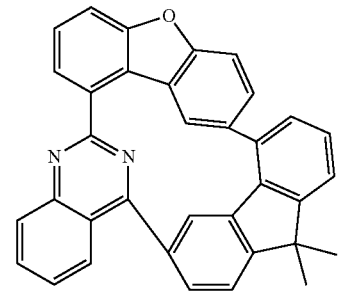
C-133
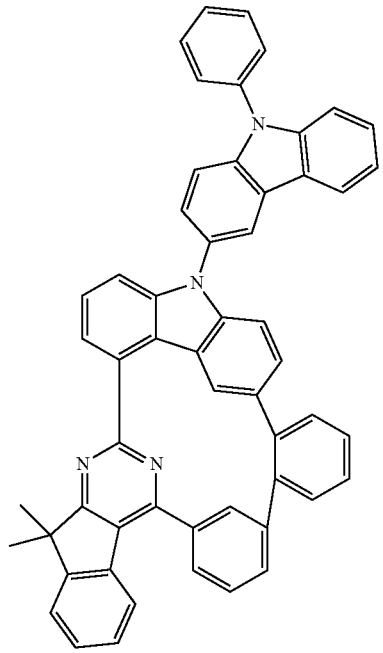

C-134
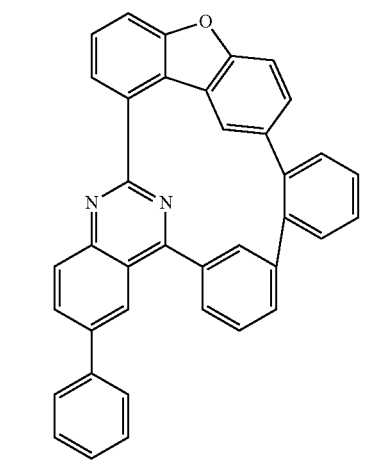
C-135
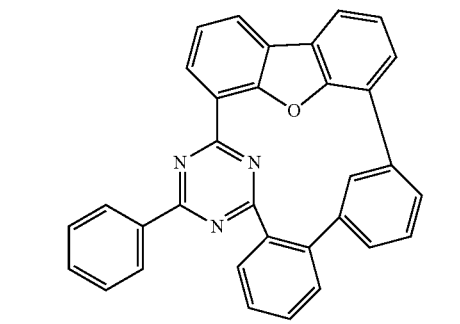
C-136
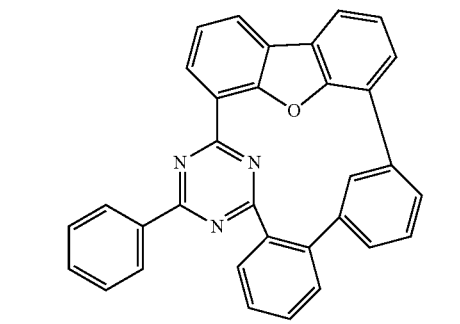
C-137
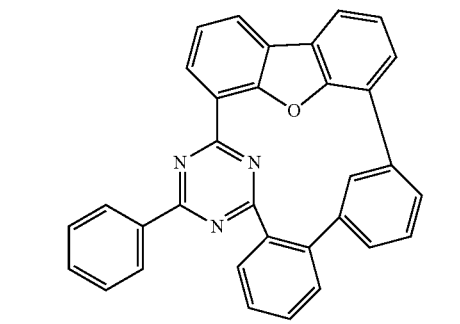
C-138
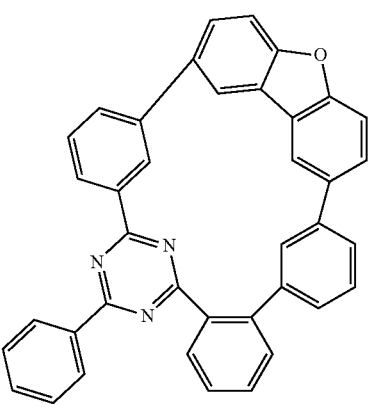
C-139
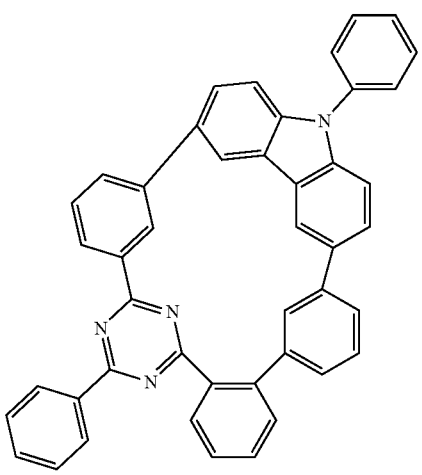
C-140
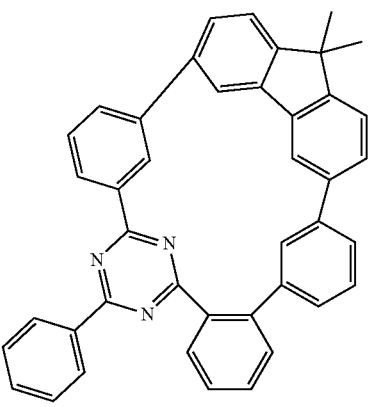
C-141
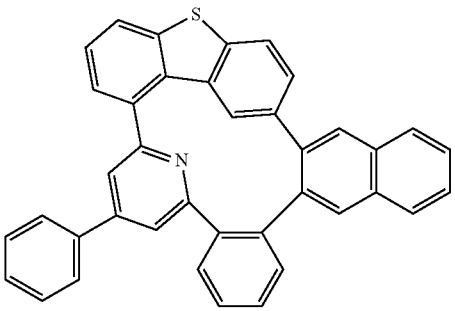

C-142
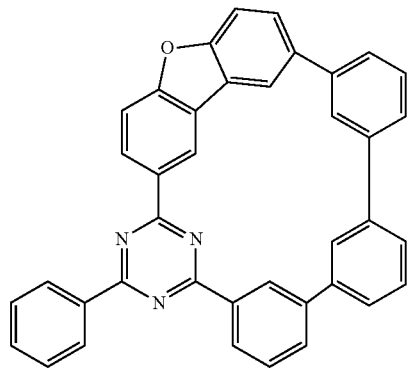
C-143
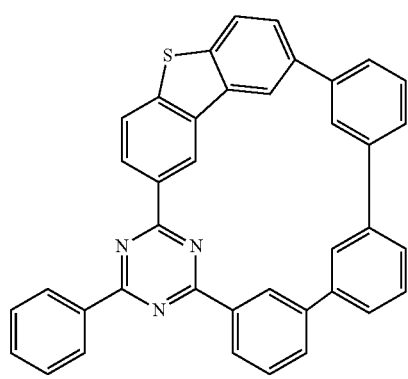
C-144
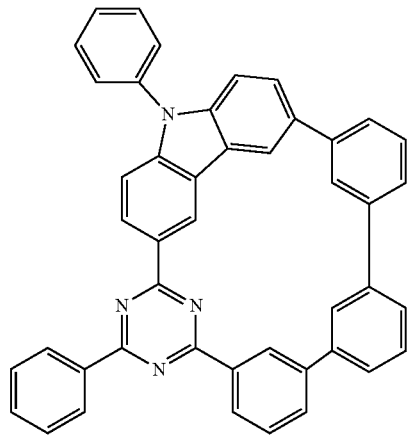
C-145
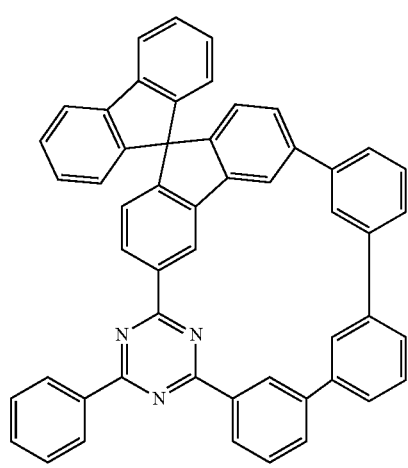
C-146
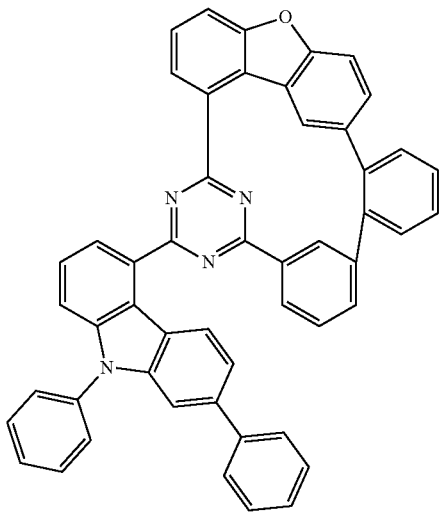
C-147
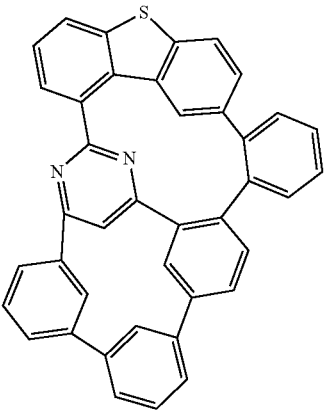
C-148
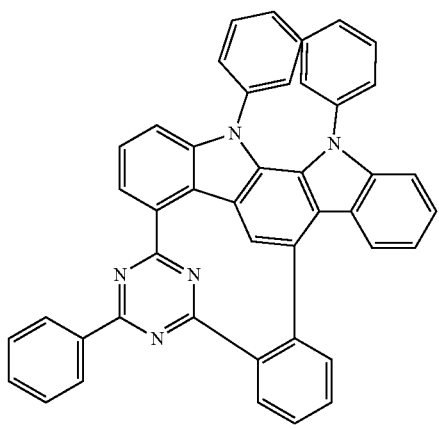

-continued
C-149
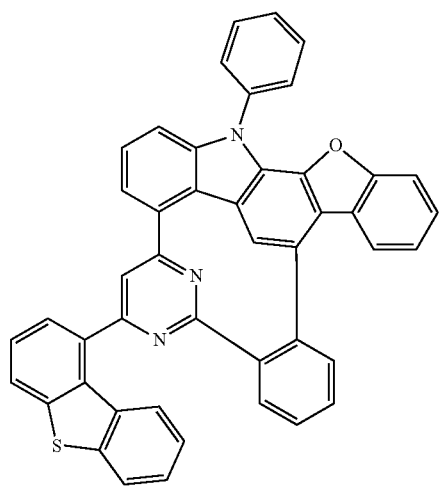
C-150
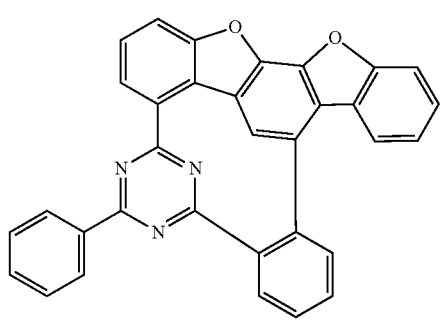
C-151
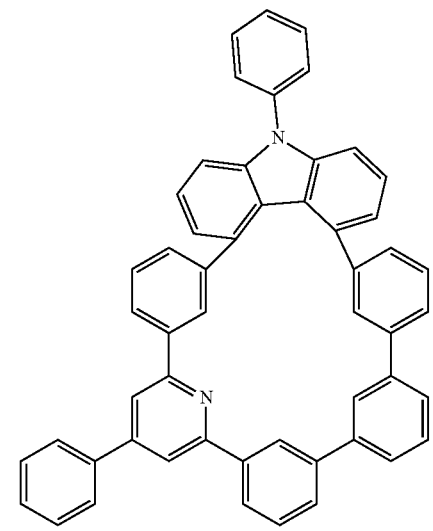
-continued
C-152
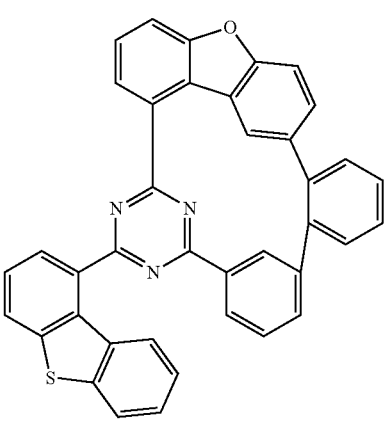
C-153
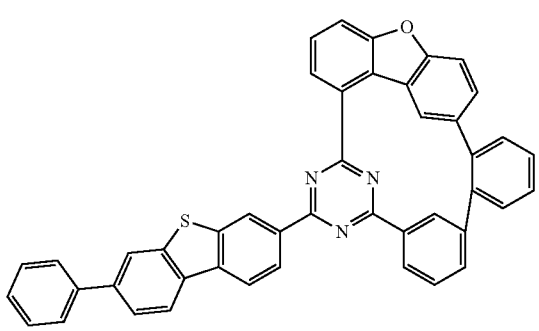
C-154
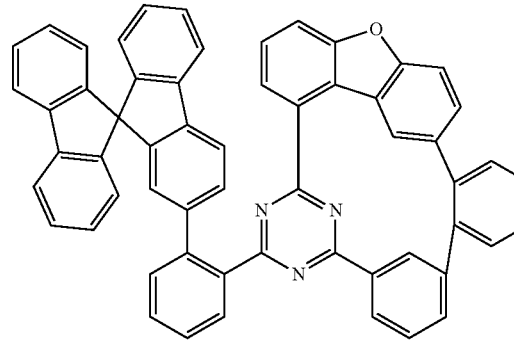
C-155
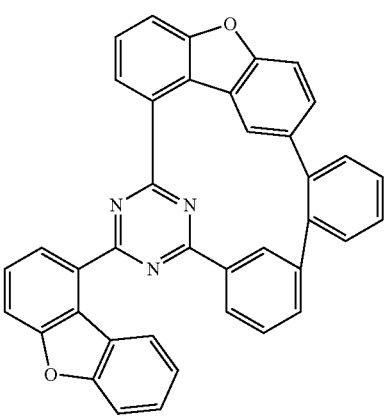

-continued
C-156
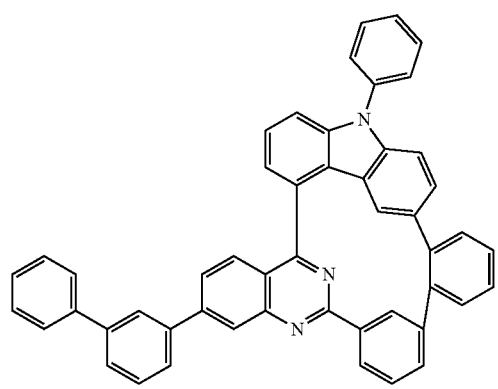
C-157
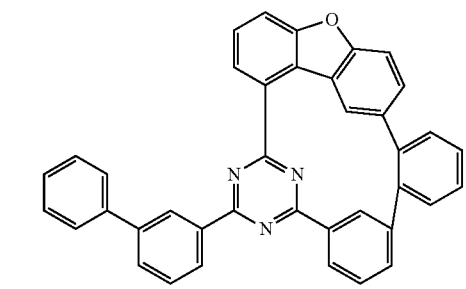
C-158
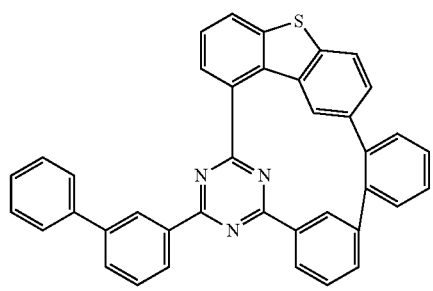
C-159
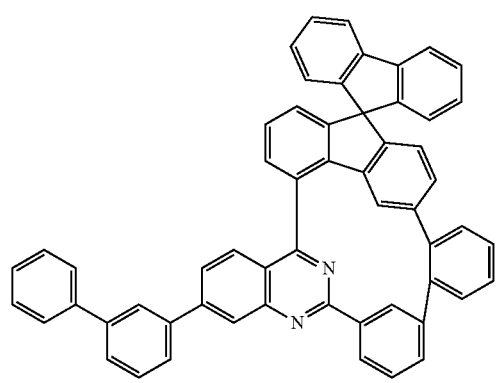
-continued
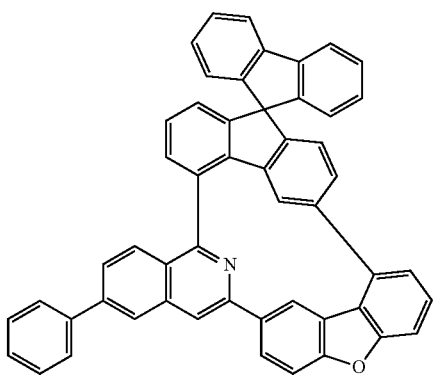
C-161
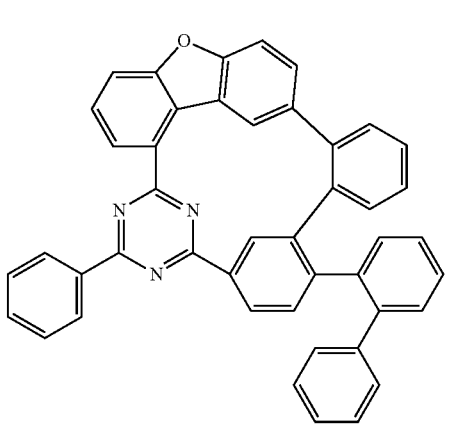
C-162

C-163
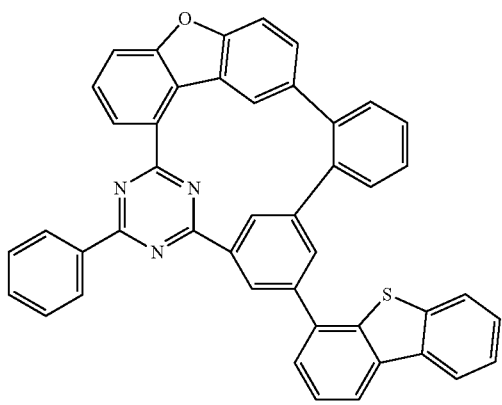
C-164
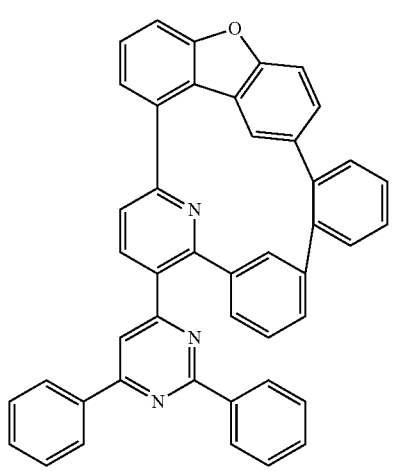
C-165
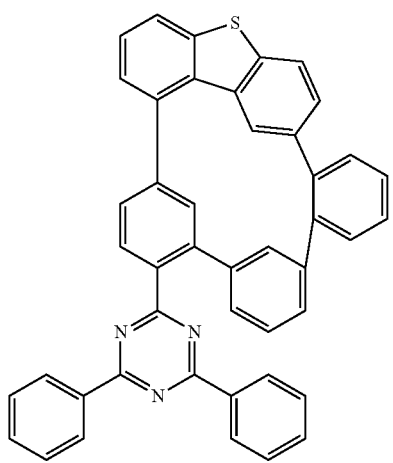
C-166
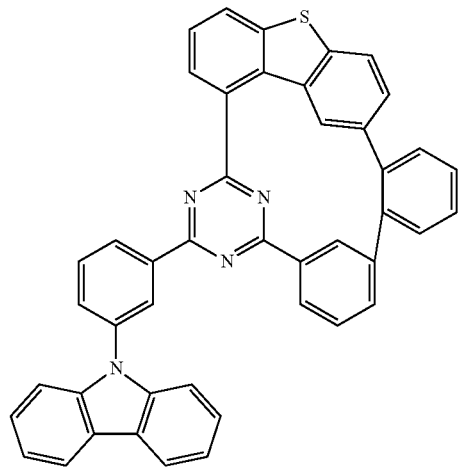
C-167
C-168
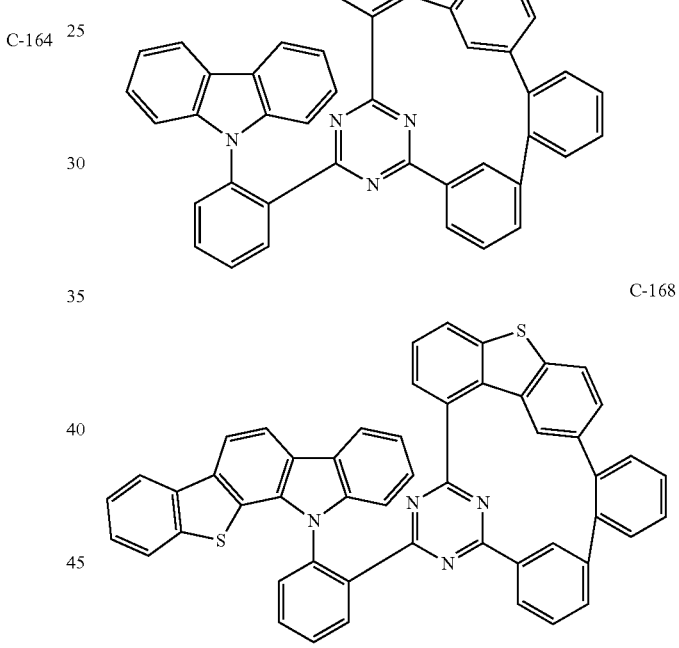
C-169
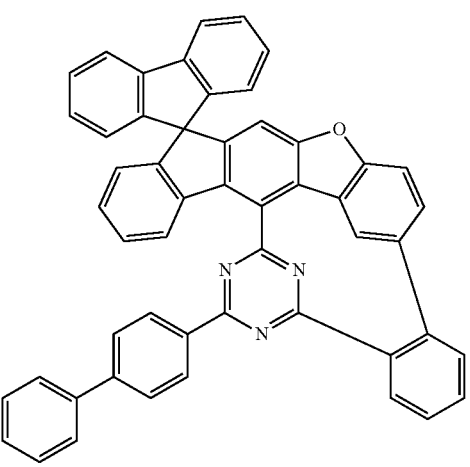

C-170
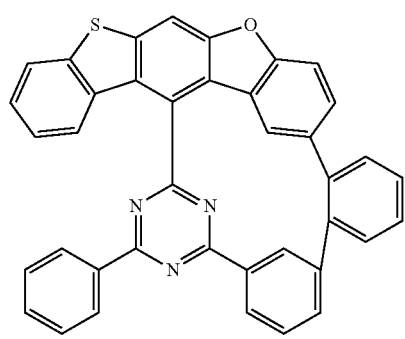
C-171
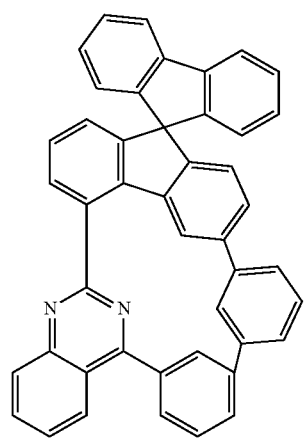
C-172
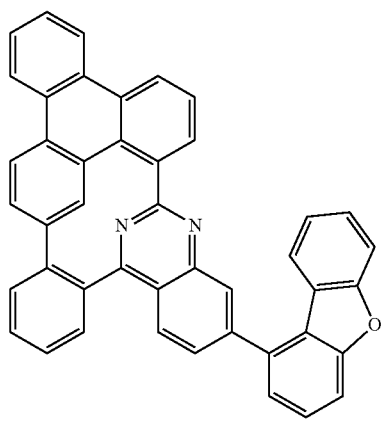
C-173
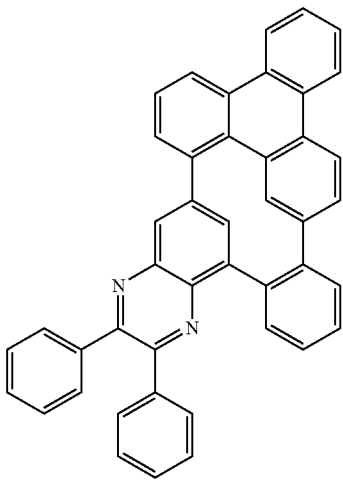
C-174
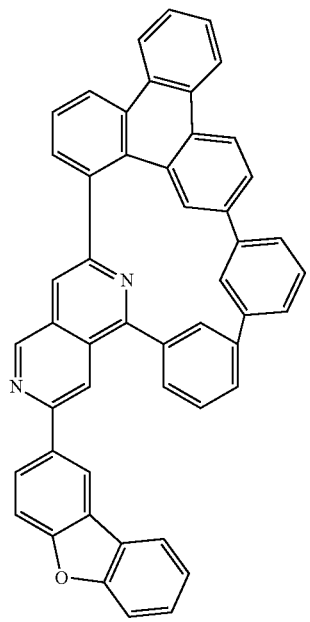
C-175
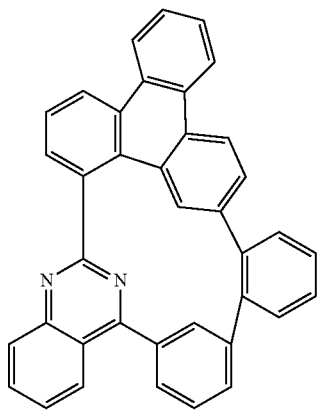

-continued
C-176
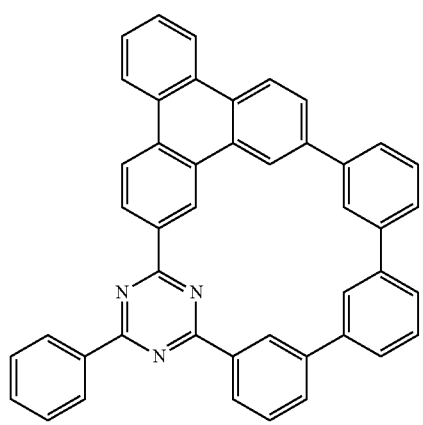
C-177
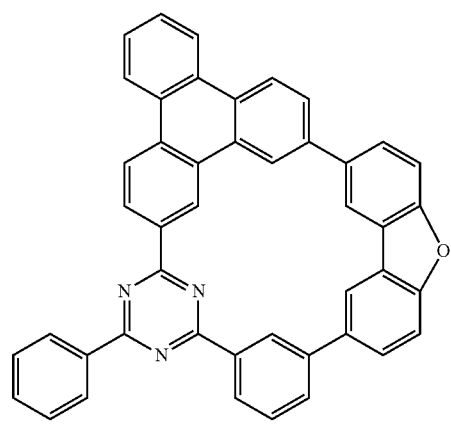
C-178
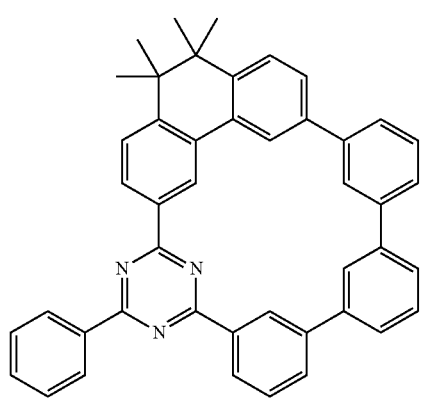
-continued
C-179
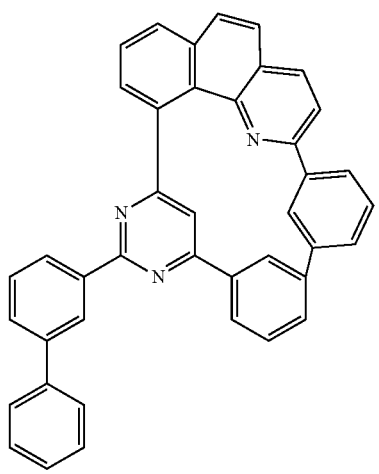
C-180
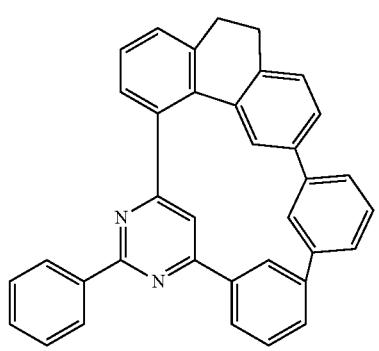
C-181

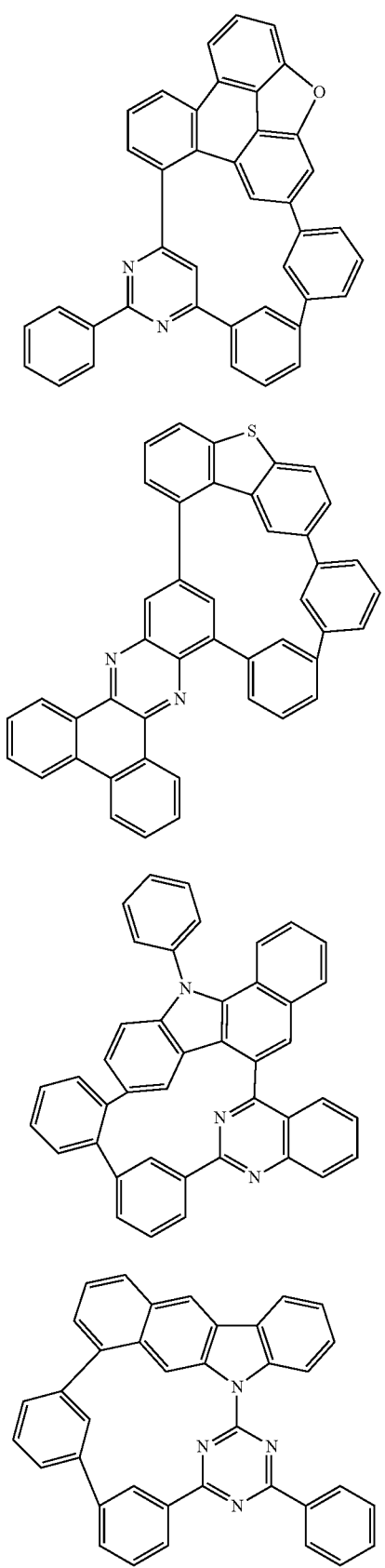
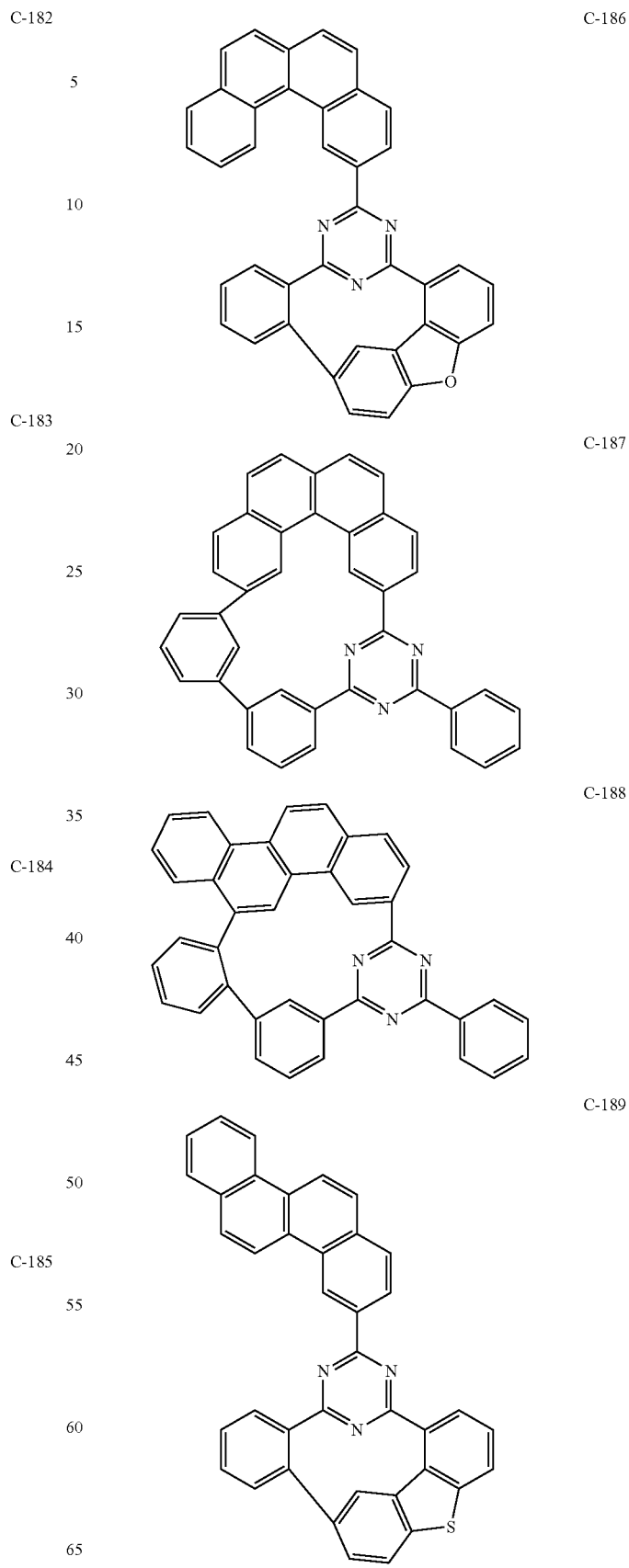

C-190
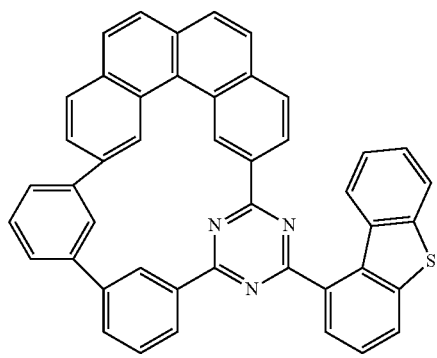
C-191
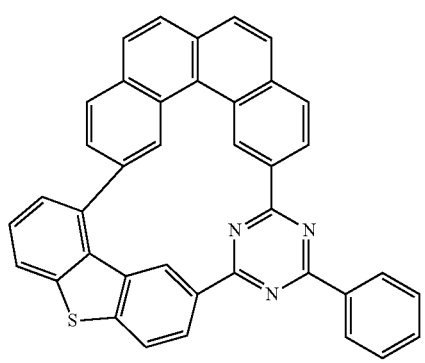
C-192
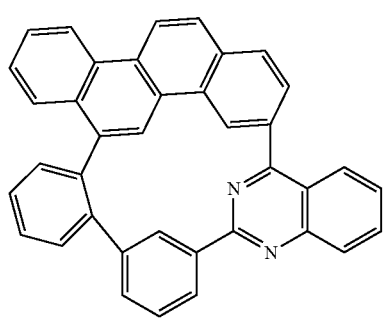
C-193
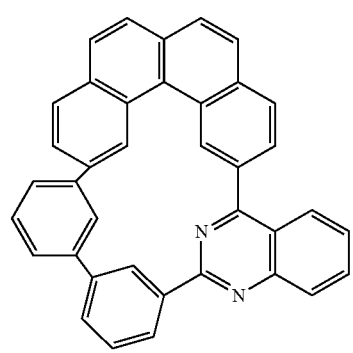
C-194
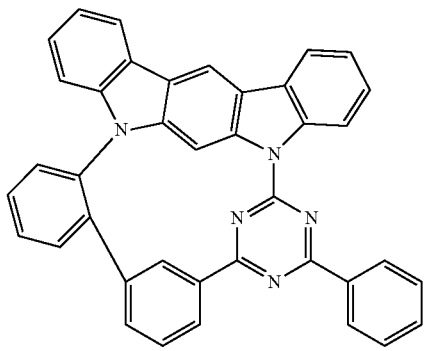
C-195
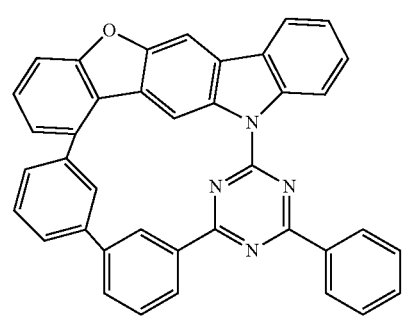
C-196
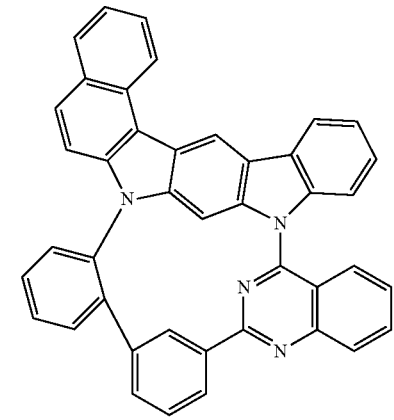
C-197
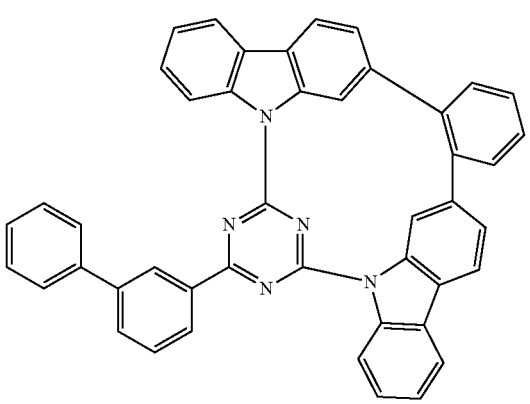

C-198
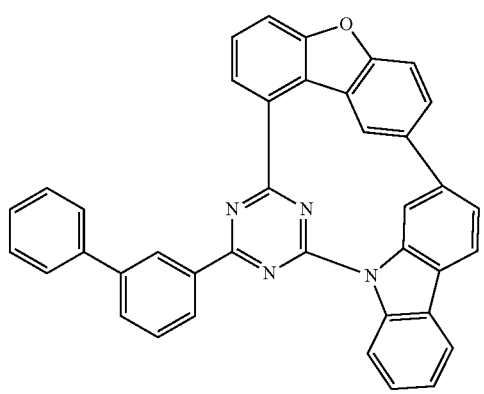
C-199
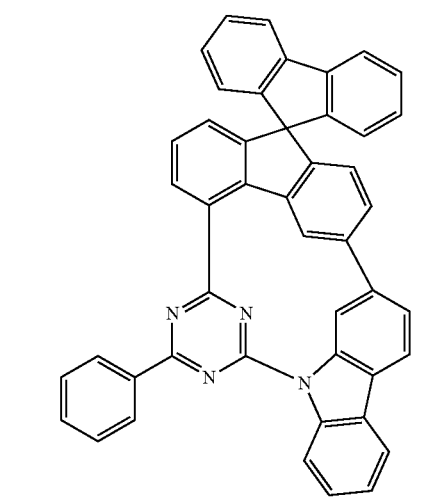
C-200
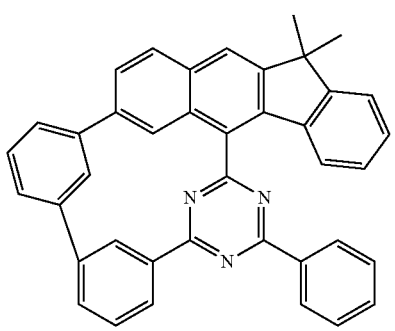
C-201
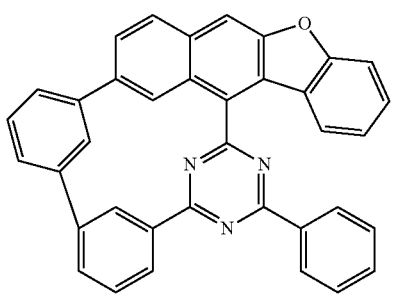
C-202
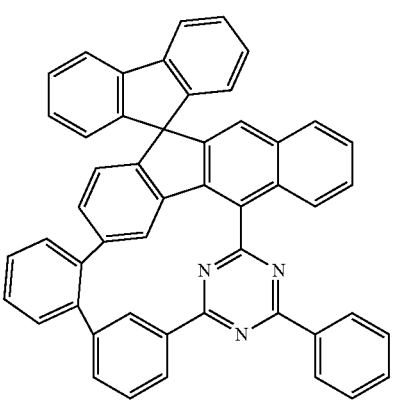
The organic electroluminescent compound represented by the formula 1 according to the present disclosure may be produced as represented by the following reaction scheme 1 or 2, but is not limited thereto; they may further be produced by a synthetic method known to a person skilled in the art.
[Reaction Scheme 1]
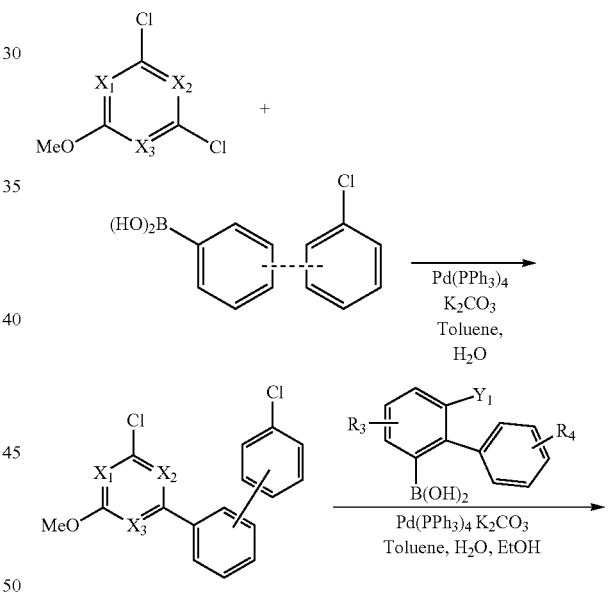
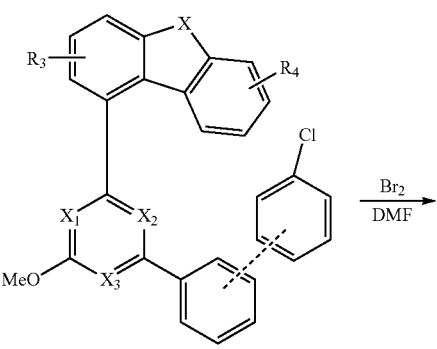

75
-continued
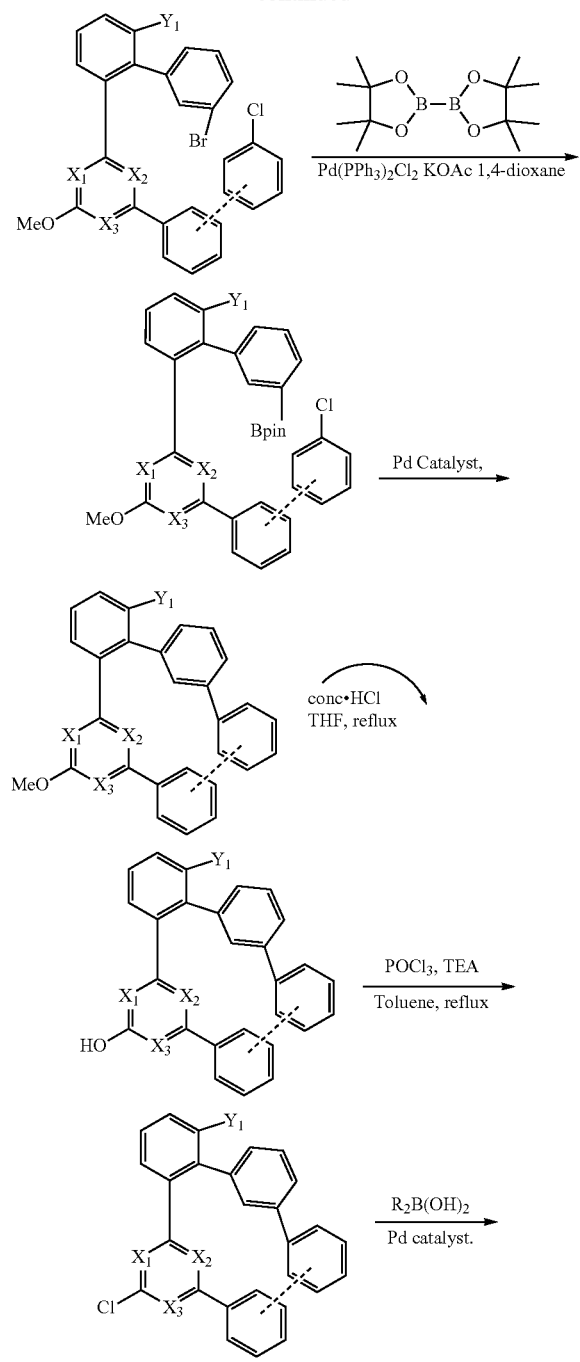
76
-continued
[Reaction Scheme 2]
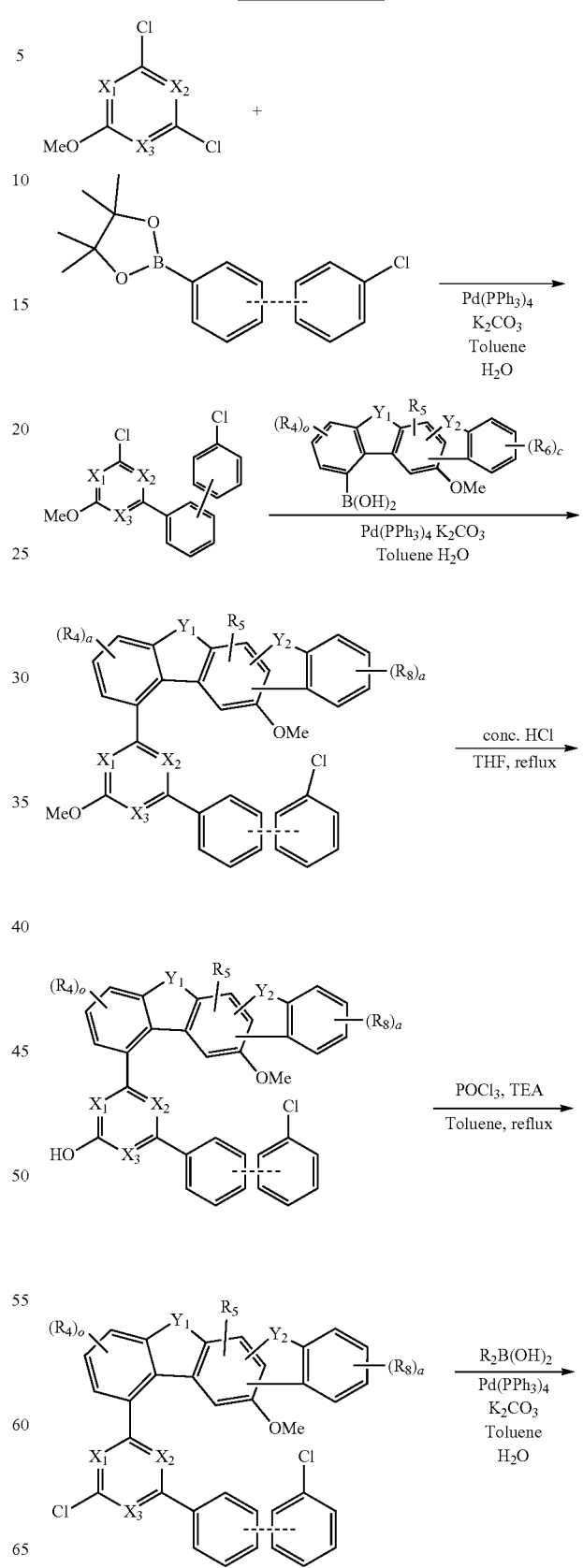

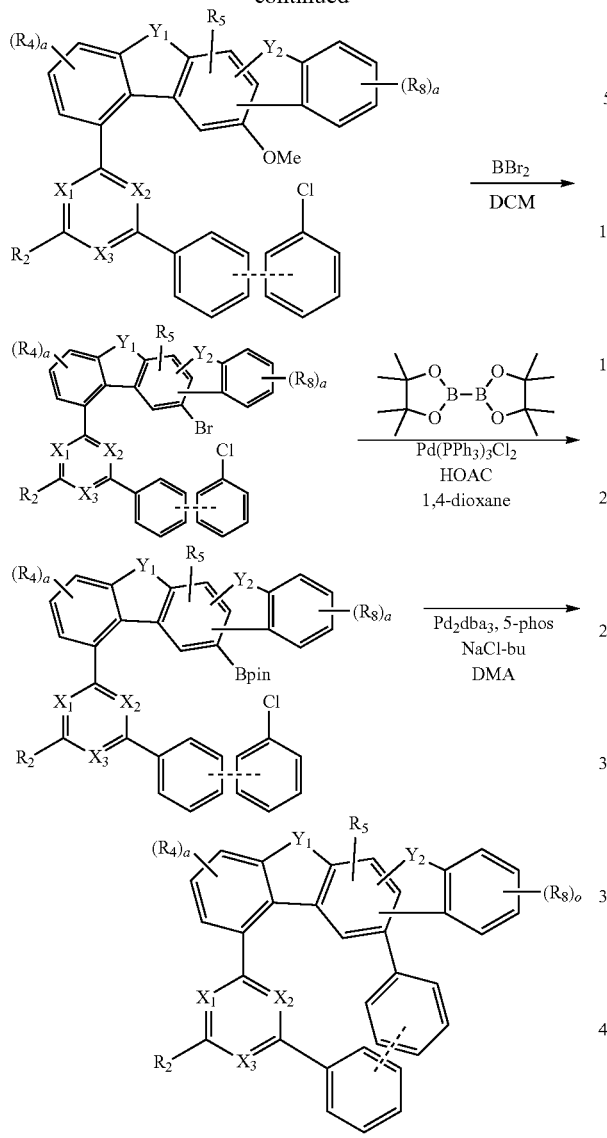

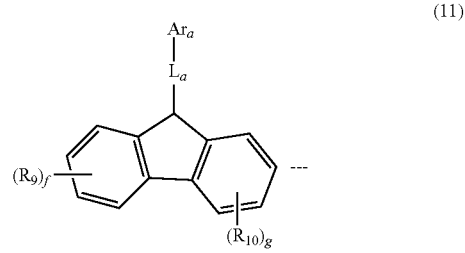

In reaction schemes 1 and 2, the definition of the substituents is as defined in formula 1 above.

As described above, exemplary synthesis examples of the compounds represented by formula 1 according to one embodiment are described, but they are based on Buchwald-Hartwig cross coupling reaction, N-arylation reaction, H-mont-mediated etherification reaction, Miyaura borylation reaction, Suzuki cross-coupling reaction, Intramolecular acid-induced cyclization reaction, Pd(II)-catalyzed oxidative cyclization reaction, Grignard reaction, Heck reaction, Cyclic Dehydration reaction, $SN_1$ substitution reaction, $SN_2$ substitution reaction, and Phosphine-mediated reductive cyclization reaction, etc. It will be understood by one skilled in the art that the above reaction proceeds even if other substituents defined in the formula 1 other than the substituents described in the specific synthesis examples are bonded.

According to one embodiment, the present disclosure provides an organic electroluminescent material comprising an organic electroluminescent compound of formula 1, and organic electroluminescent device comprising the organic electroluminescent material.

According to one embodiment of the present disclosure, the organic electroluminescent material of the present disclosure may be formed of the organic electroluminescent compound of formula 1 alone, and may further include other conventional materials included in the organic electroluminescent material. Specifically, the organic electroluminescent material of the present disclosure may include one or more compounds represented by formula 1 above. For example, the compound of formula 1 may be included in a light-emitting layer, and when included in the light-emitting layer, the compound of formula 1 may be included as a host, and more specifically, may be included as a phosphorescent green host.

According to another embodiment of the present disclosure, the organic electroluminescent material of the present disclosure may further include an organic electroluminescent compound which is different from the organic electroluminescent compound of formula 1 (a first host material) as a second host material. That is, the organic electroluminescent material according to one embodiment of the present disclosure may include a plurality of host materials. Specifically, a plurality of host materials according one embodiment may include at least one compound(s) of formula 1 as a first host material, and may include at least one second host material(s) which is different from the first host material. Herein, the weight ratio of the first host material to the second host material may be in the range of 1:99 to 99:1, preferably 10:90 to 90:10, more preferably 30:70 to 70:30.

The second host material according to one embodiment comprises a compound represented by the following formula 11.

(11)

In formula 11,
$L_a$ represents a single bond, a substituted or unsubstituted (C6-C30)arylene, or a substituted or unsubstituted (3- to 30-membered)heteroarylene;
$Ar_a$ represents a substituted or unsubstituted (C6-C30) aryl, or a substituted or unsubstituted (3- to 30-membered)heteroaryl;
$R_9$ and $R_{10}$ each independently represent hydrogen, deuterium, halogen, cyano, a substituted or unsubstituted (C1-C30)alkyl, a substituted or unsubstituted (C6-C30) aryl, a substituted or unsubstituted (3- to 50-membered) heteroaryl, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of an (C3-C30) aliphatic ring and an (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30) alkenylamino, a substituted or unsubstituted (C1-C30)

alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkeny(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or may be linked to the adjacent substituent to form a ring(s);

f and g each independently represent an integer of 1 to 4; and when f and g are 2 or more, each of $R_9$ and each of $R_{10}$ may be the same or different.

The second host material represented by formula 11 according to one embodiment may be represented by the following formula 12 or 13.

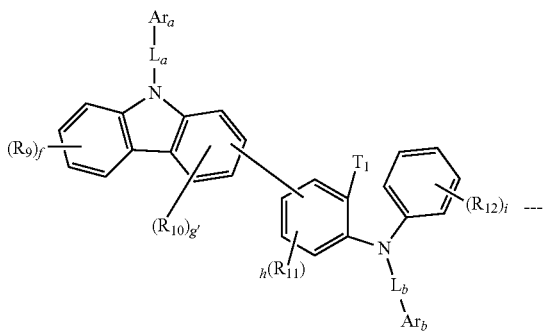
(12)

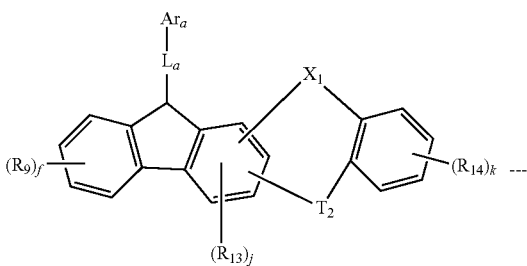
(13)

In formulas 12 and 13, $L_a$, $Ar_a$, $R_9$, $R_{10}$, and f are as defined in formula 11;

$T_1$ and $T_2$ each independently represent a single bond, O, or S;

$L_a$ is defined as $L_a$ in formula 11;

$Ar_b$ is defined as $Ar_a$ in formula 11;

$R_{11}$ to $R_{14}$ each independently are as defined as $R_9$ in formula 11;

$X_1$ represents O, S, or $NR_a$;

$R_a$ represents a substituted or unsubstituted (C6-C30)aryl;

g' and h each independently represent an integer of 1 to 3, i and k each independently represent an integer of 1 to 4, and j represents an integer of 1 or 2; and when g', h, i, j, and k are 2 or more, each of $R_{10}$, each of $R_{11}$, each of $R_{12}$, each of $R_{13}$, and each of $R_{14}$ may be the same or different.

In one embodiment, $L_a$ and $L_b$ each independently may be a single bond or a substituted or unsubstituted (C6-C30) arylene, preferably, a single bond or a substituted or unsubstituted (C6-C25)arylene, more preferably a single bond or a substituted or unsubstituted (C6-C18)arylene. For example, $L_a$ and $L_b$ each independently may be a single bond, phenylene, or biphenylene.

In one embodiment, $Ar_a$ and $Ar_b$ each independently represent a substituted or unsubstituted (C6-C30)aryl, preferably, may be a substituted or unsubstituted (C6-C25)aryl, more preferably, (C6-C25)aryl unsubstituted or substituted with (C6-C30)aryl or (5- to 30-membered)heteroaryl. For example, $Ar_a$ and $Ar_b$ each independently represent phenyl unsubstituted or substituted with at least one of methyl; cyano; triphenylsilane; phenyl; biphenyl; naphthyl; and carbazolyl unsubstituted or substituted with phenyl, a substituted or unsubstituted o-biphenyl, a substituted or unsubstituted m-biphenyl, a substituted or unsubstituted p-terphenyl, a substituted or unsubstituted m-terphenyl, a substituted or unsubstituted o-terphenyl, a substituted or unsubstituted fluorenyl, naphthyl unsubstituted or substituted with phenyl, or a substituted or unsubstituted triphenylenyl.

In one embodiment, $R_a$ represents substituted or unsubstituted (C6-C30)aryl, preferably, may be a substituted or unsubstituted (C6-C25)aryl, more preferably, may be (C6-C25)aryl unsubstituted or substituted with (C6-C30) aryl or (5- to 30-membered)heteroaryl. For example, $R_a$ may be phenyl unsubstituted or substituted with at least one of phenyl; biphenyl; naphthyl; and carbazolyl unsubstituted or substituted with phenyl, a substituted or unsubstituted o-biphenyl, a substituted or unsubstituted m-biphenyl, a substituted or unsubstituted p-terphenyl, a substituted or unsubstituted m-terphenyl, a substituted or unsubstituted o-terphenyl, naphthyl unsubstituted or substituted with phenyl, or a substituted or unsubstituted triphenylenyl.

In one embodiment, $R_9$ to $R_{14}$ each independently may be hydrogen, a substituted or unsubstituted (C1-C30)alkyl, a substituted or unsubstituted (C6-C30)aryl, or a substituted or unsubstituted (3- to 30-membered)heteroaryl, preferably, hydrogen, a substituted or unsubstituted (C1-C10)alkyl, a substituted or unsubstituted (C6-C25)aryl, or a substituted or unsubstituted (5- to 25-membered)heteroaryl, more preferably, hydrogen, a substituted or unsubstituted (C1-C4)alkyl, a substituted or unsubstituted (C6-C18)aryl, or a substituted or unsubstituted (5- to 18-membered)heteroaryl. For example, $R_9$ to $R_{14}$ each independently may be hydrogen, a substituted or unsubstituted methyl, a substituted or unsubstituted phenyl, or a substituted or unsubstituted carbazolyl.

According to one embodiment, the compound represented by formula 11 above may be more specifically illustrated by the following compounds, but is not limited thereto.

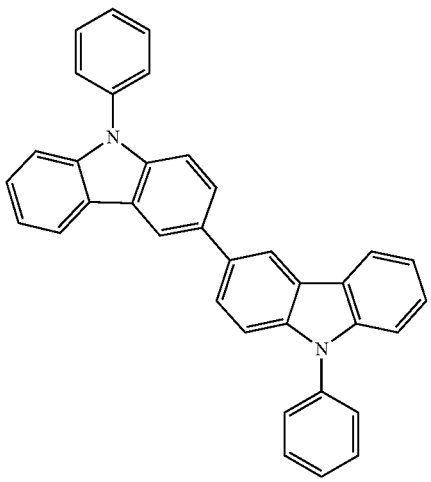
H-1

H-2
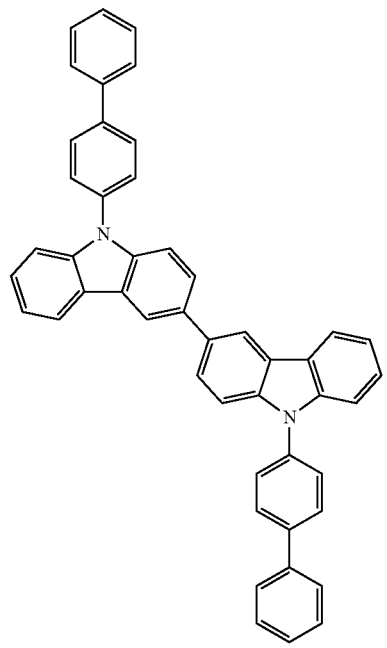
H-4
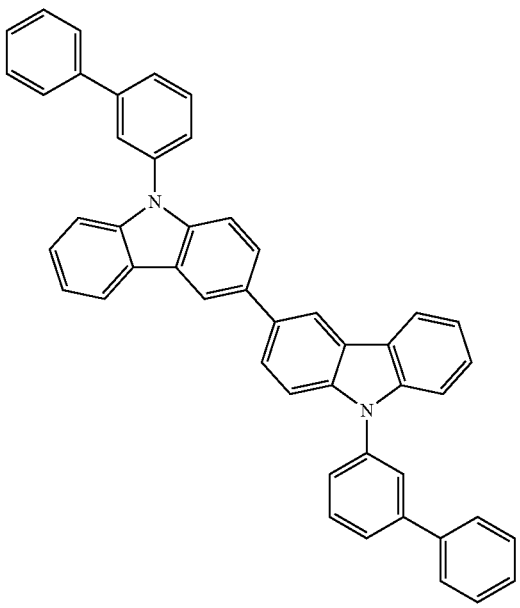
H-3
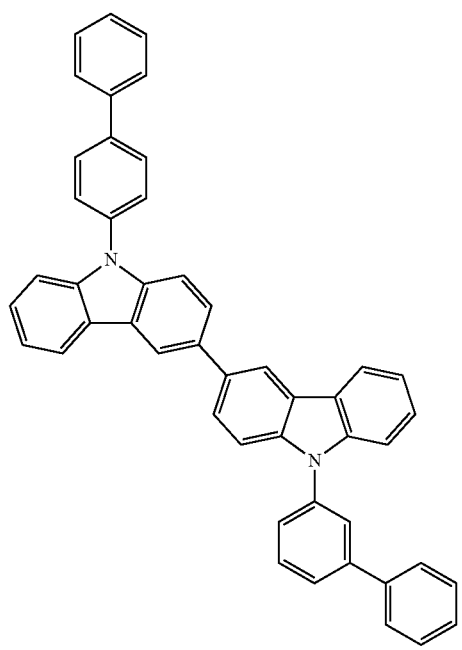
H-5
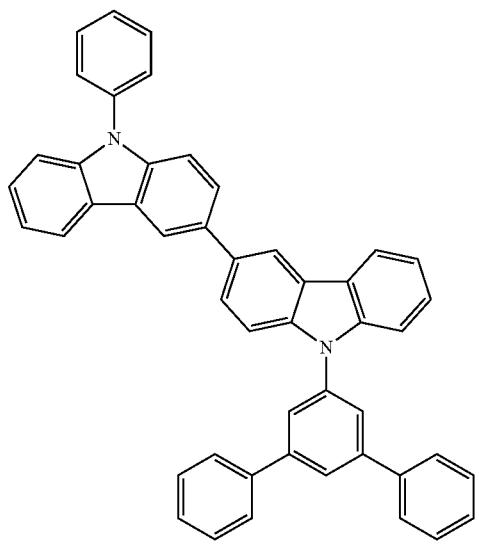

H-6
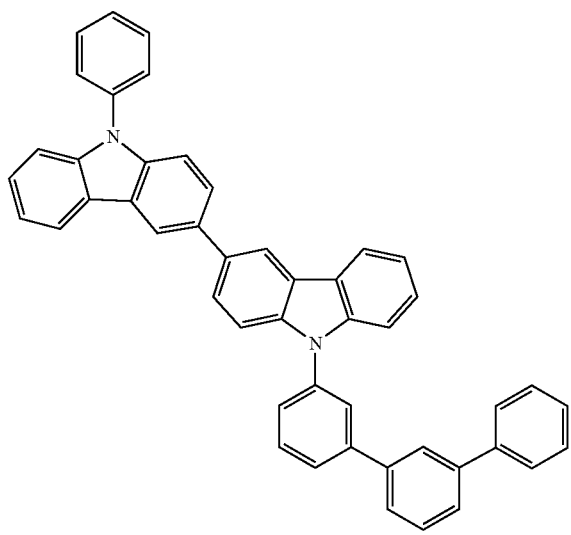
H-7
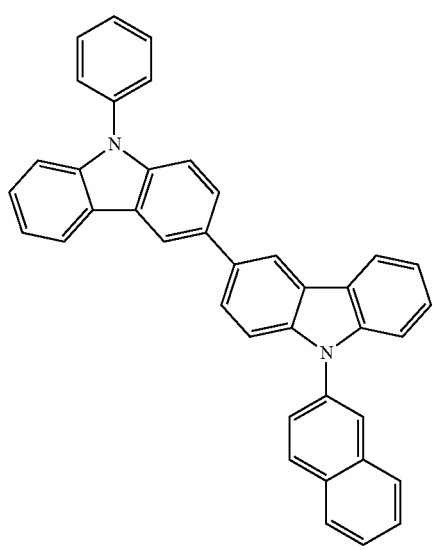
H-8
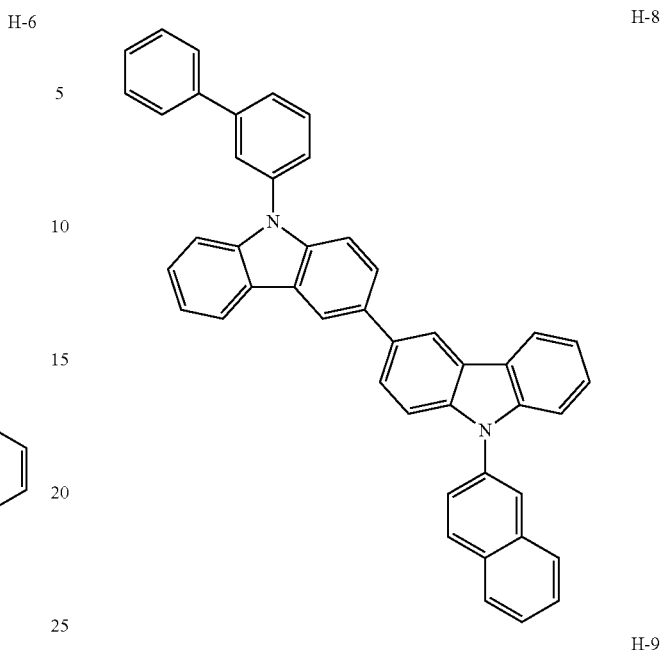
H-9
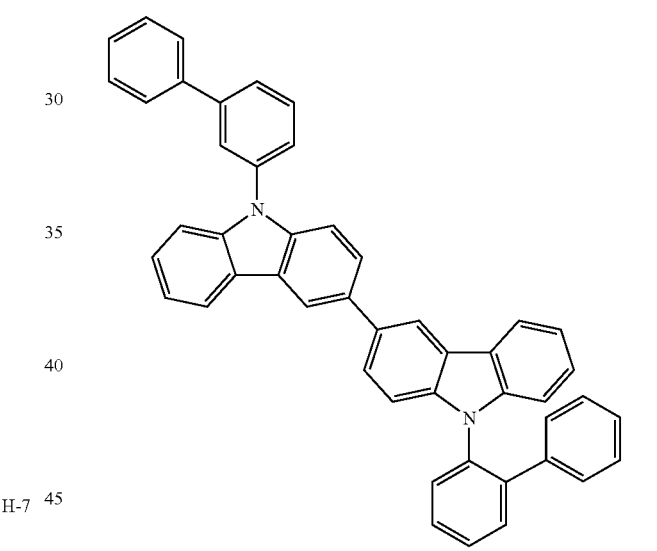
H-10
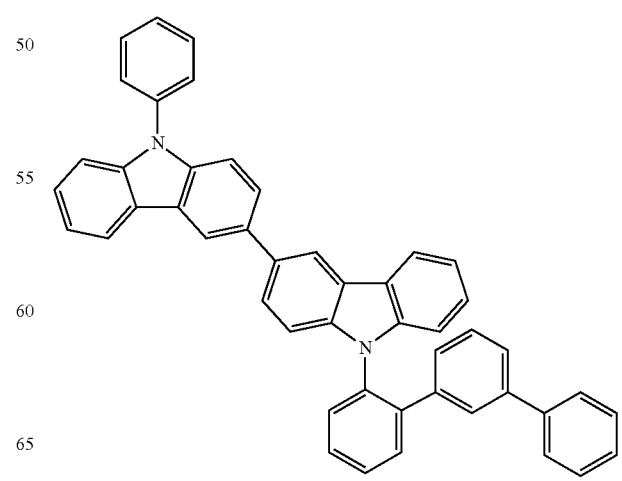

H-11
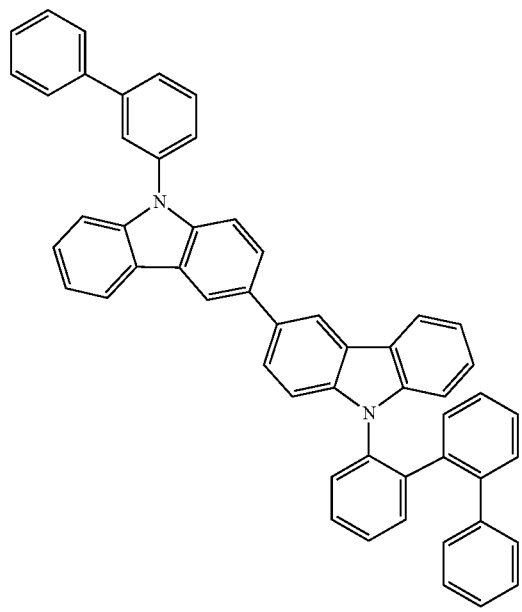
H-12
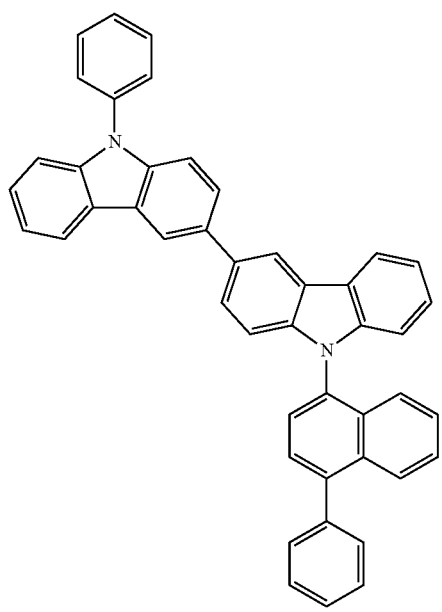
H-13
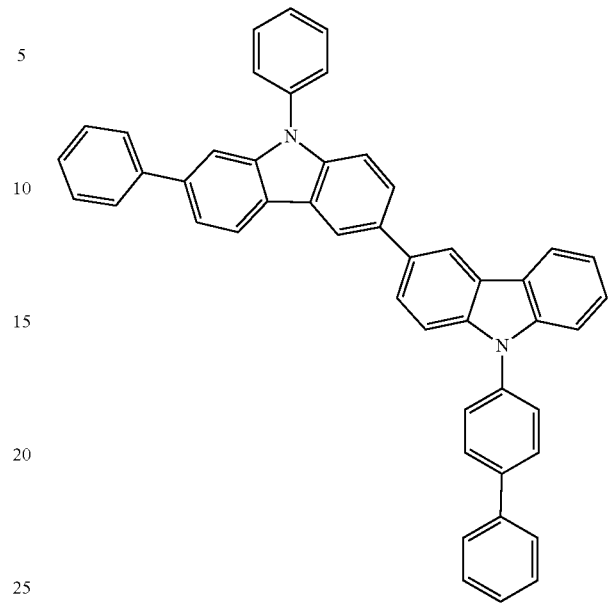
H-14
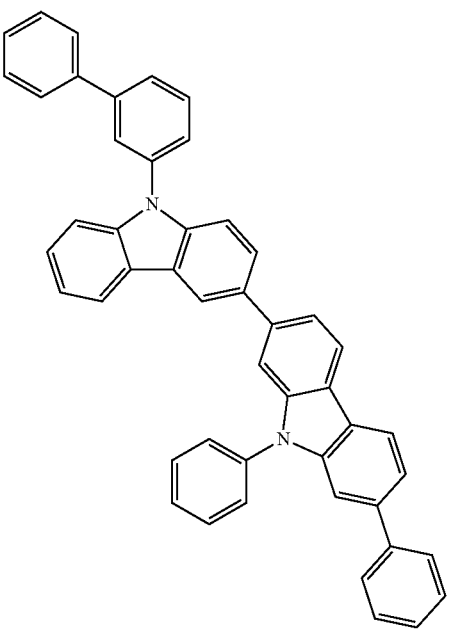

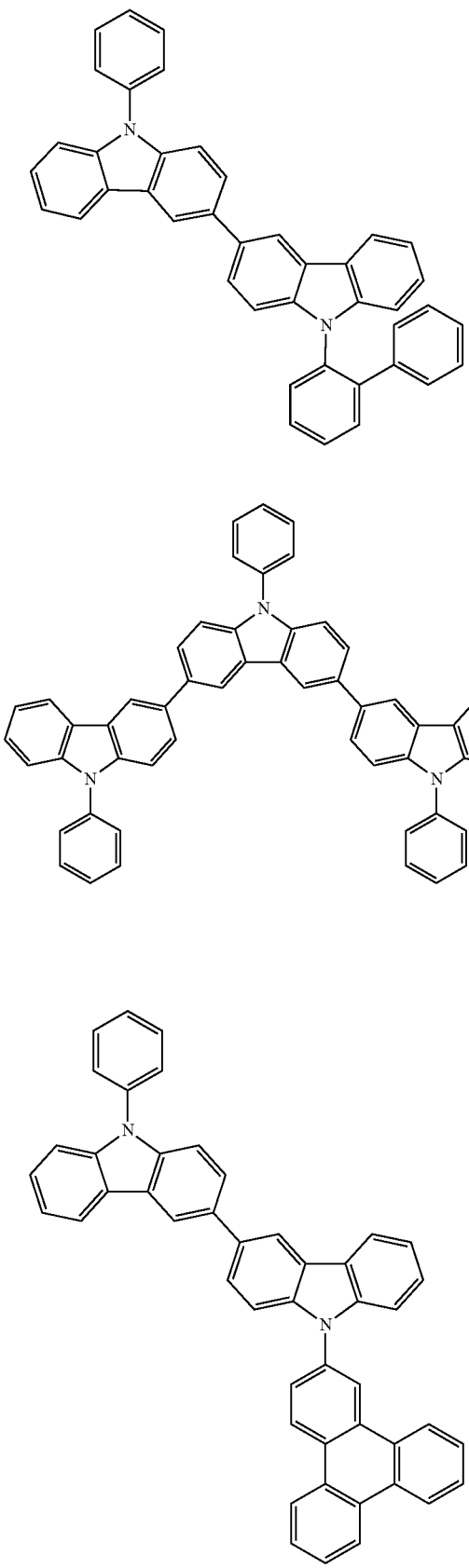
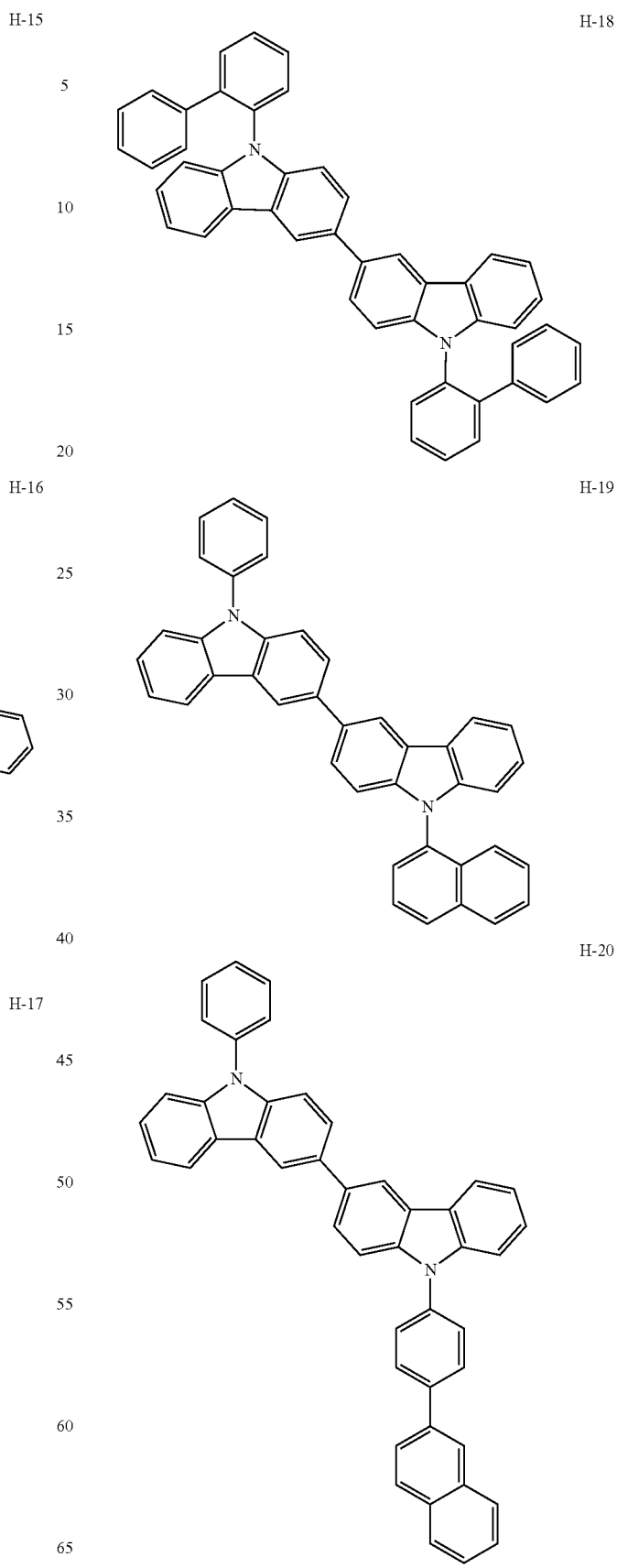

H-21
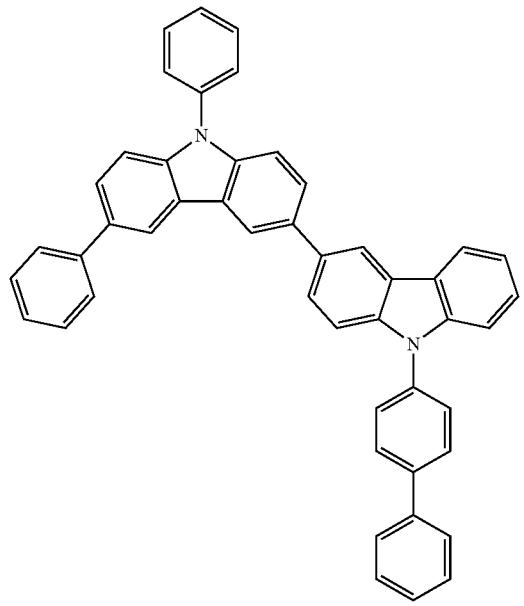
H-22
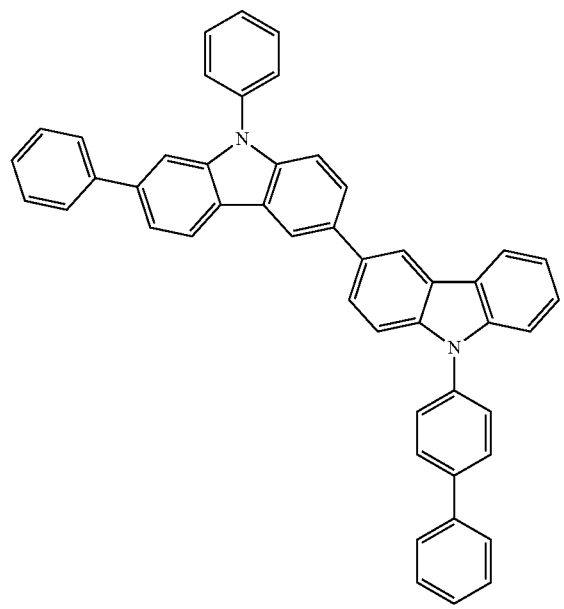
H-23
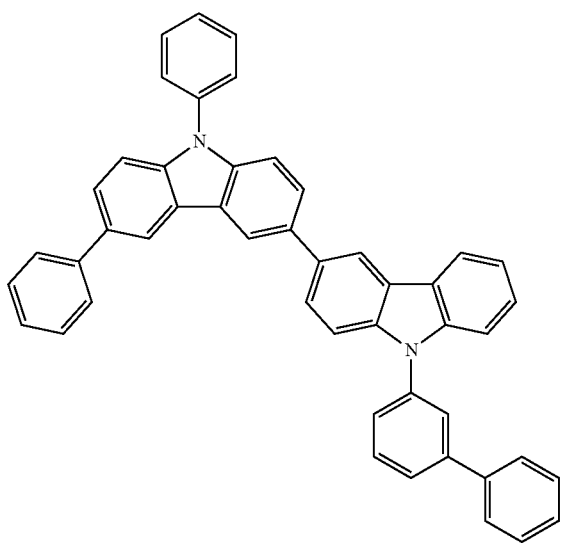
H-24
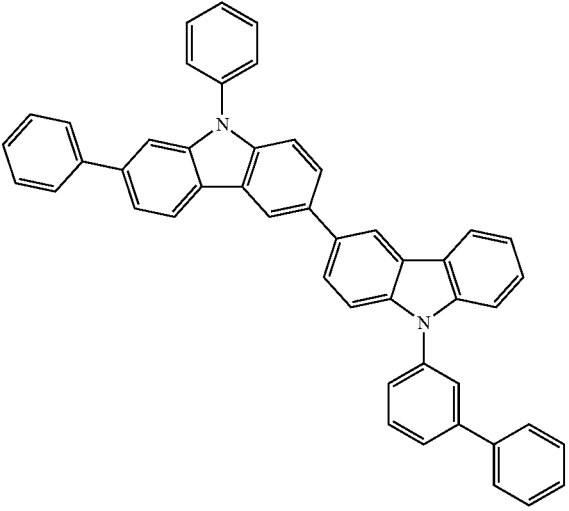

H-25
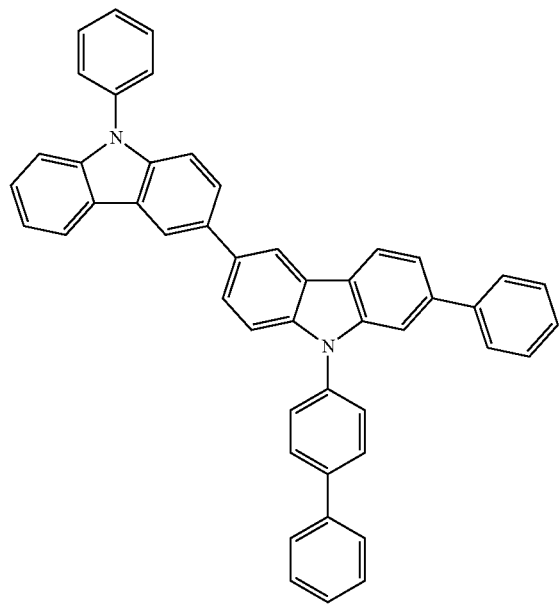
H-27
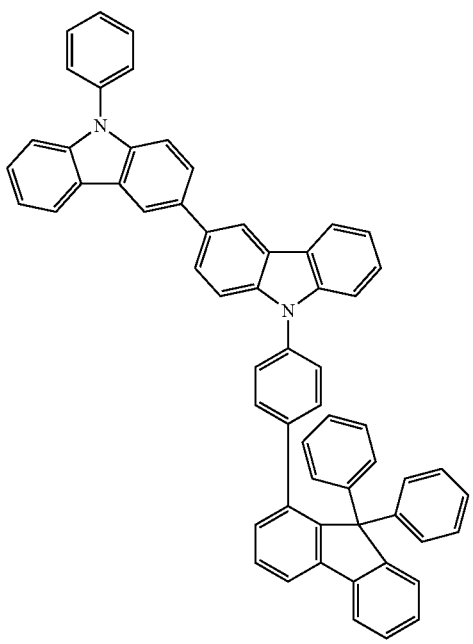
H-26
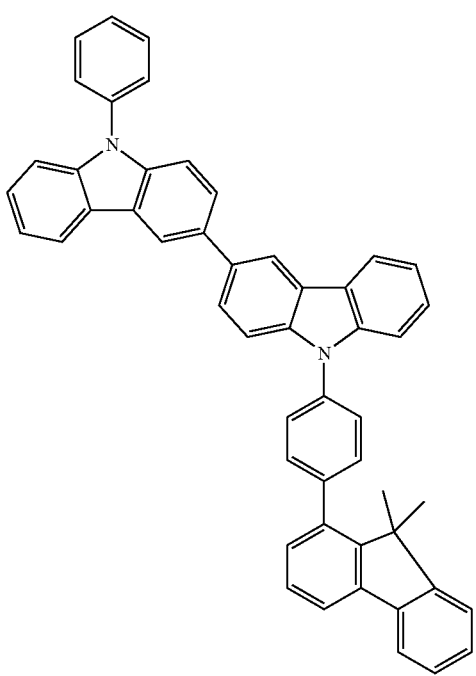
H-28
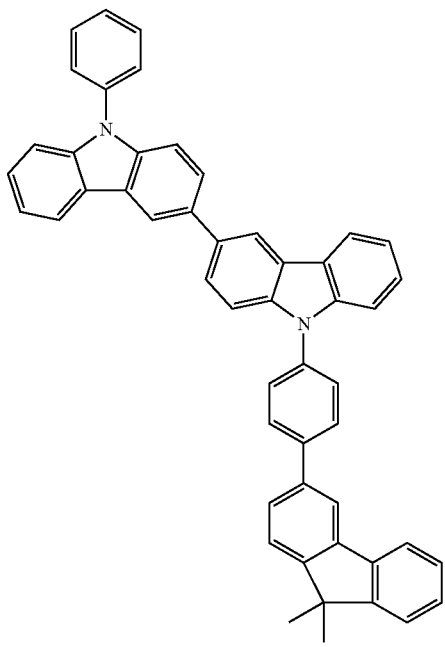

H-29
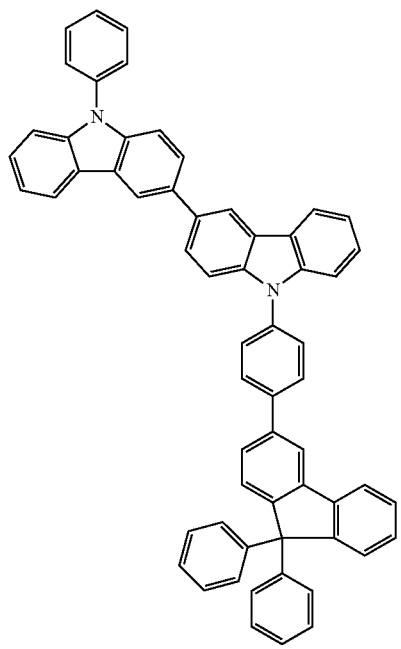
H-30
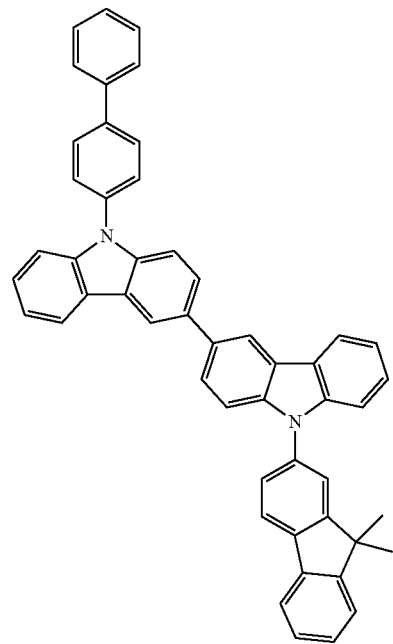
H-31
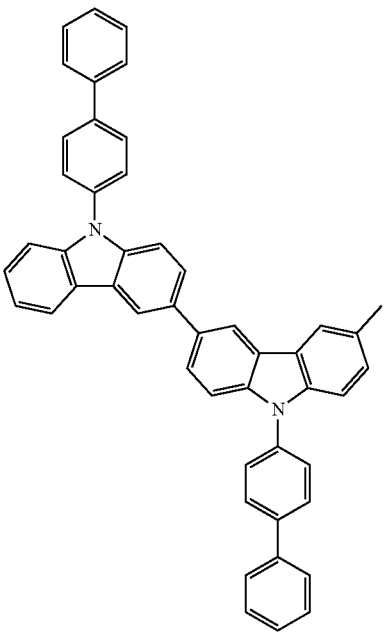
H-32
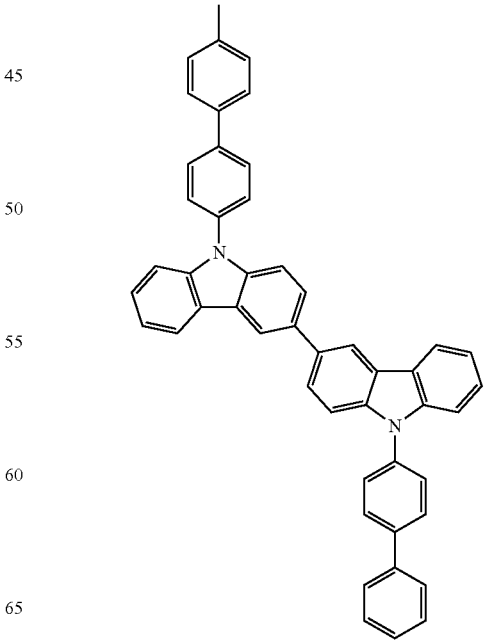

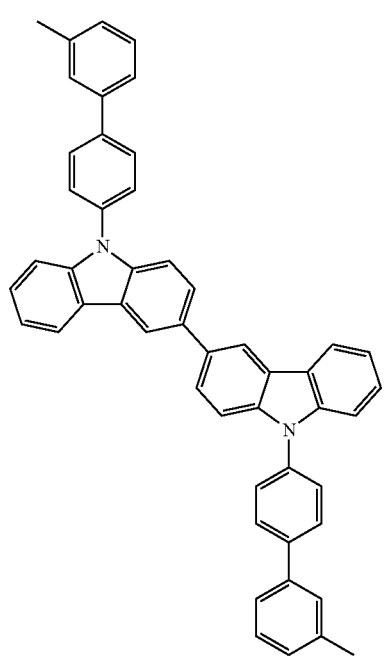
H-33
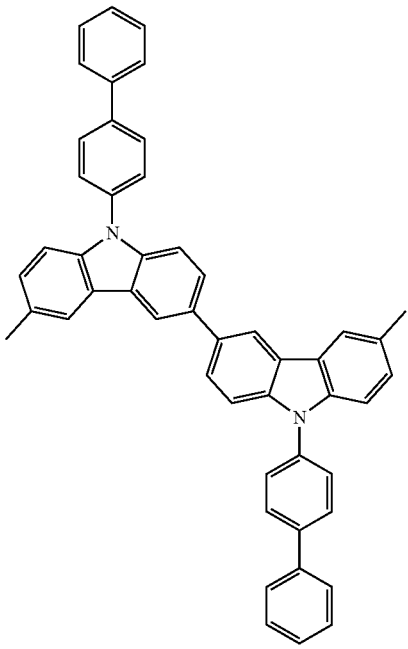
H-35
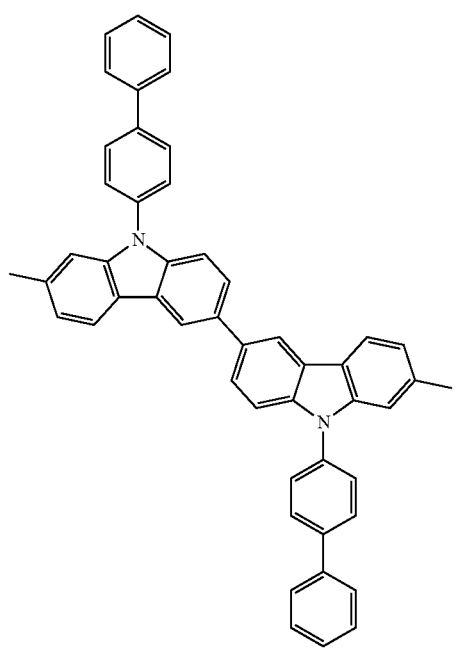
H-34
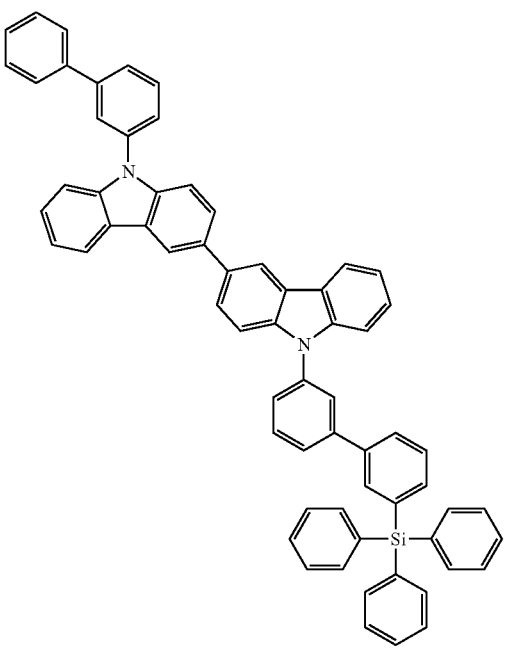
H-36

97
-continued
H-37
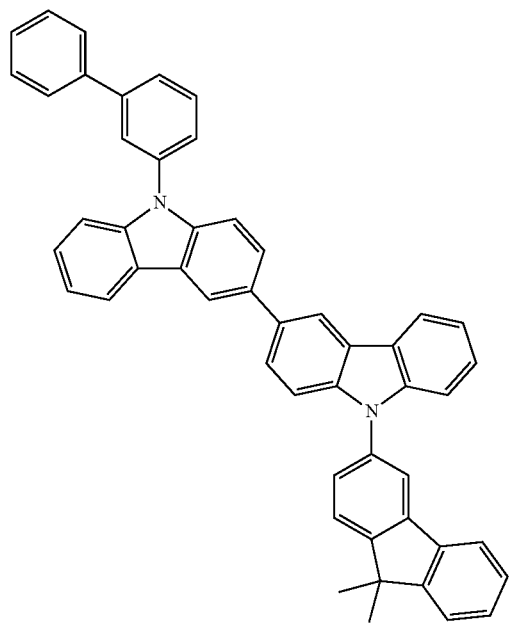
H-38
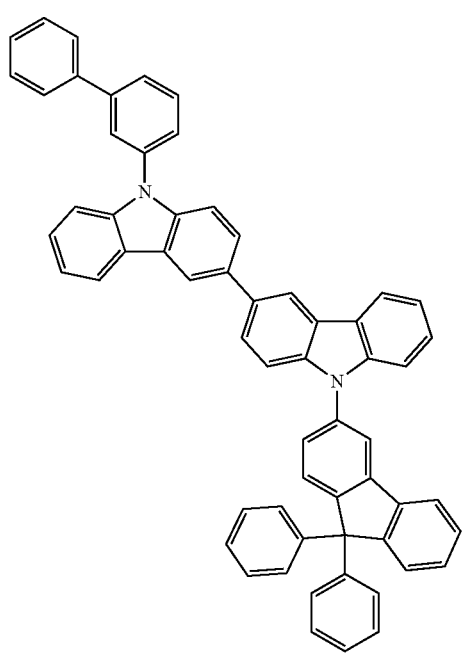
98
-continued
H-39
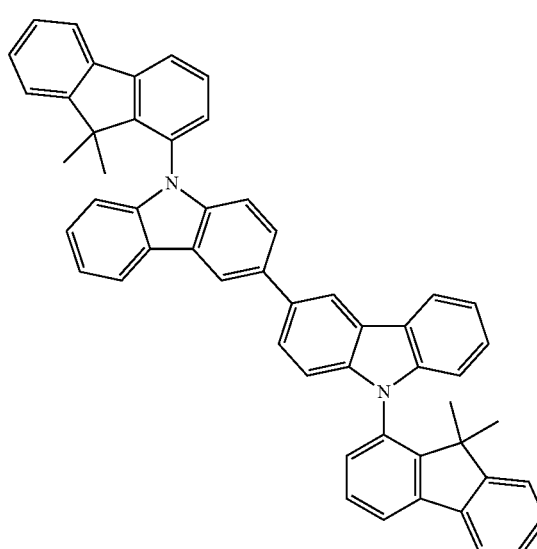
H-40
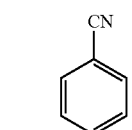
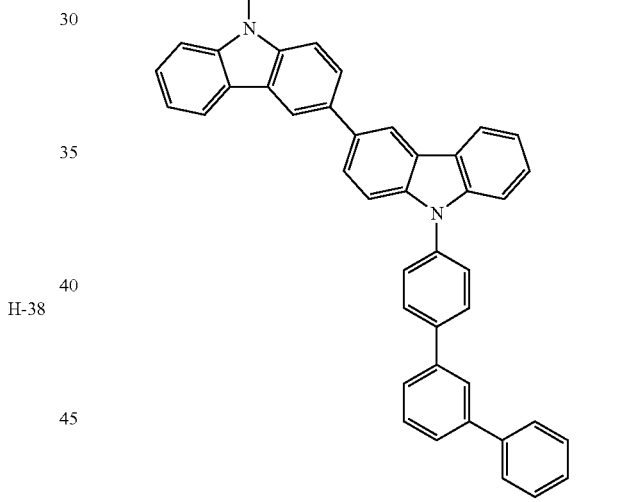
H-41
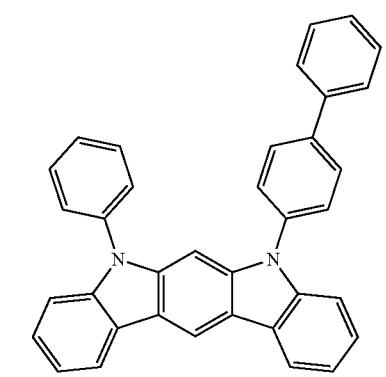

-continued
H-42
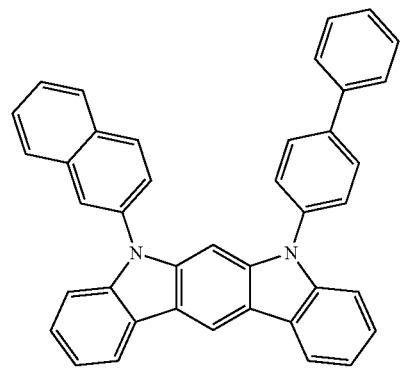
H-43
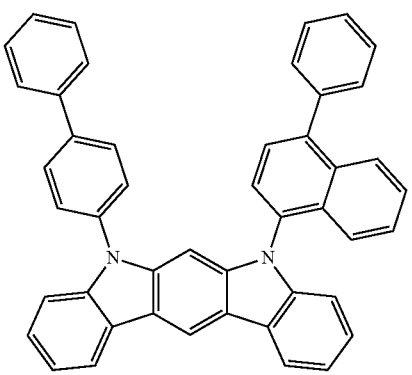
H-44
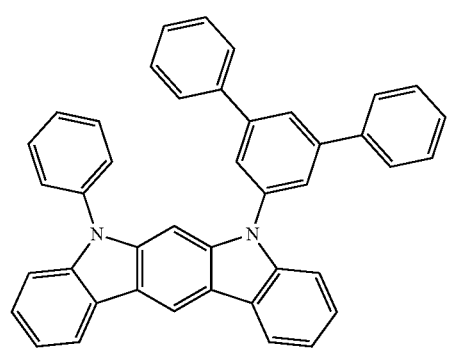
H-45
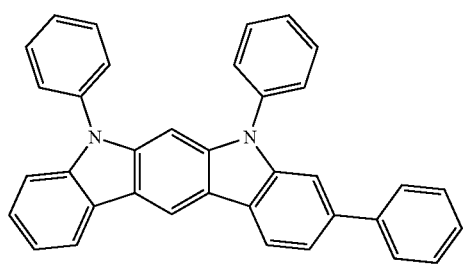
-continued
H-46
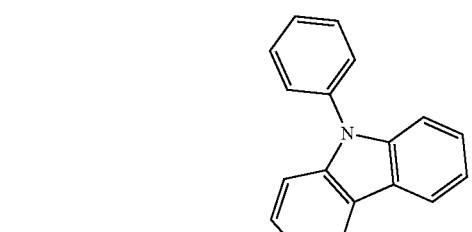
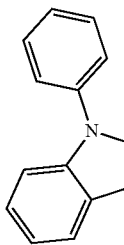
H-47
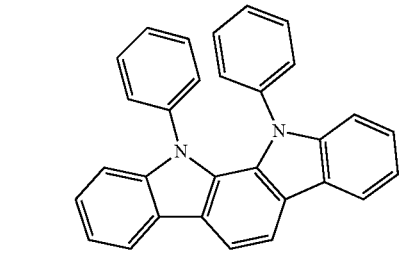
H-48
H-49
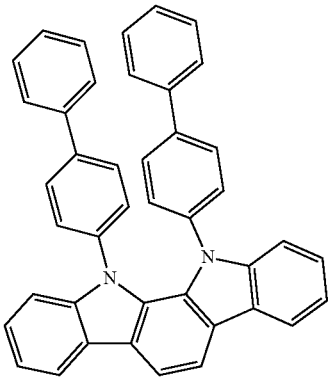

-continued
H-50
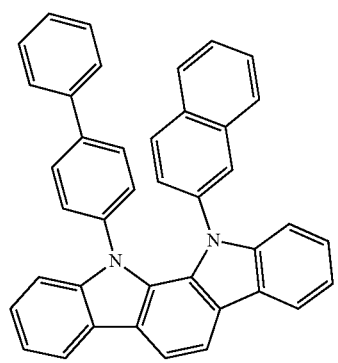
H-53
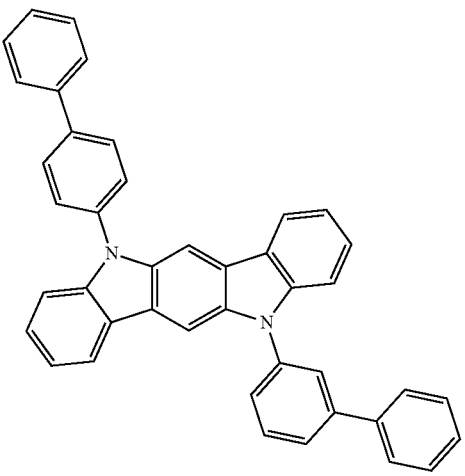
H-51
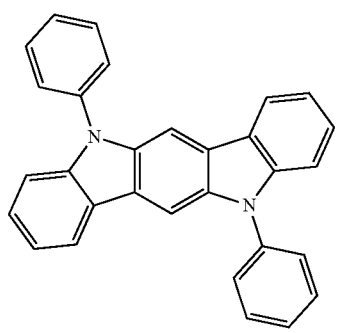
H-54
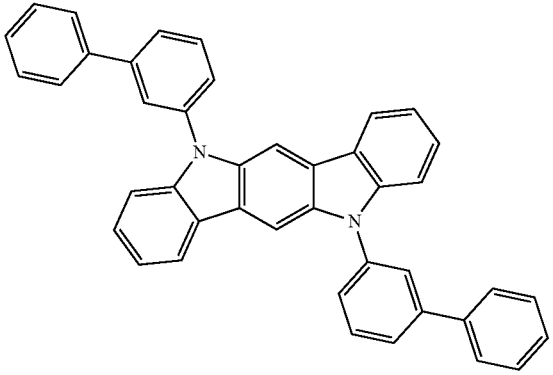
H-52
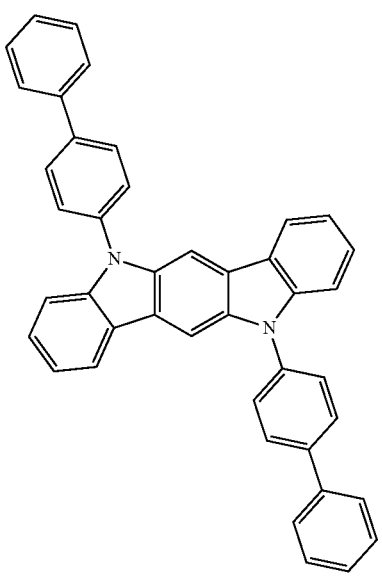
H-55
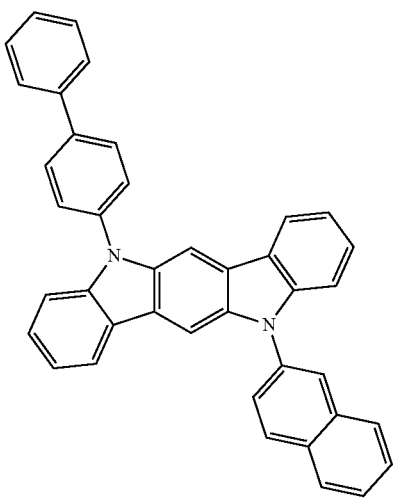

-continued
H-56
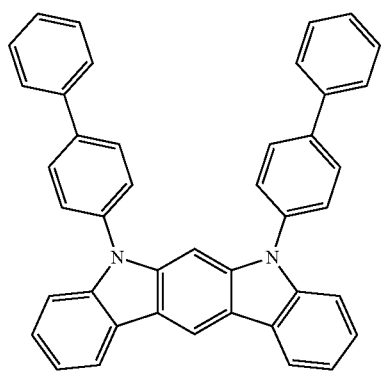
H-57
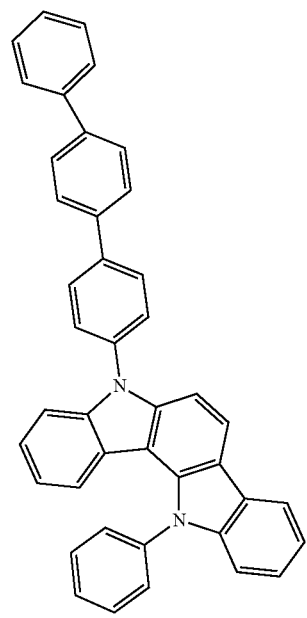
H-58
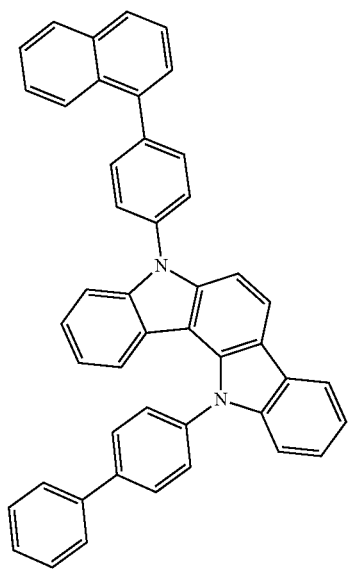
-continued
H-59
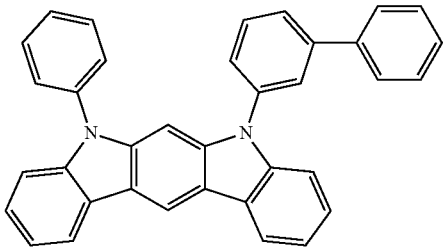
H-60
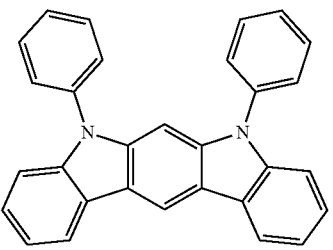
H-61
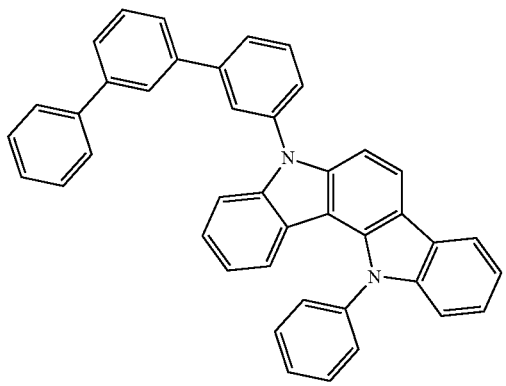
H-62
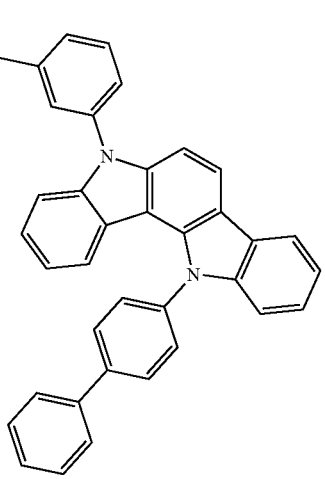

H-63
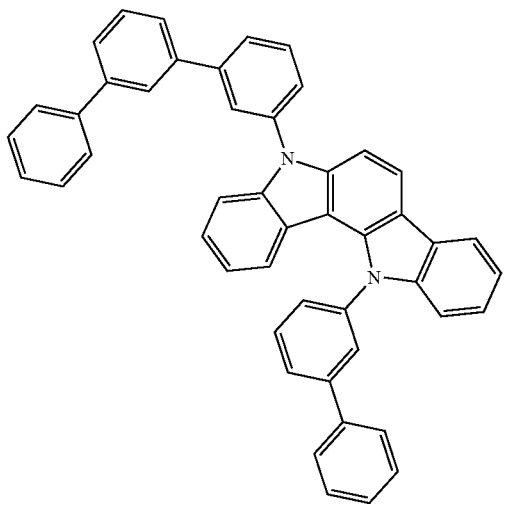
H-64
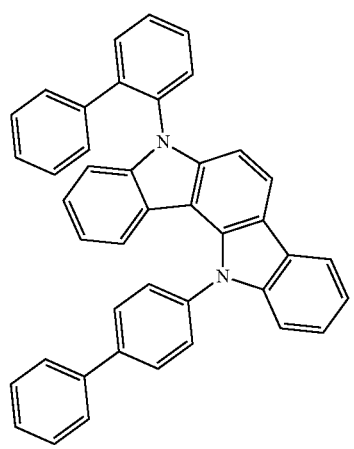
H-65
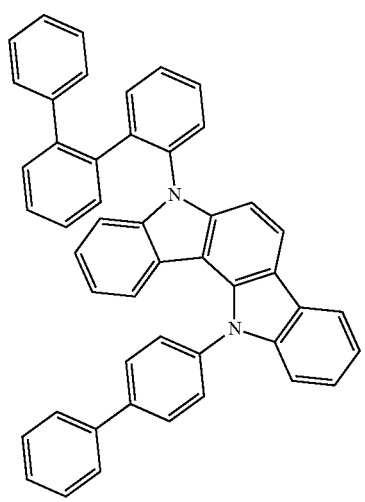
H-66
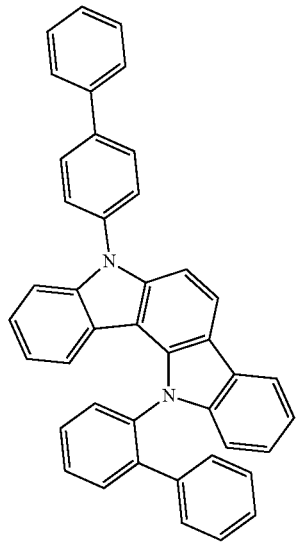
H-67
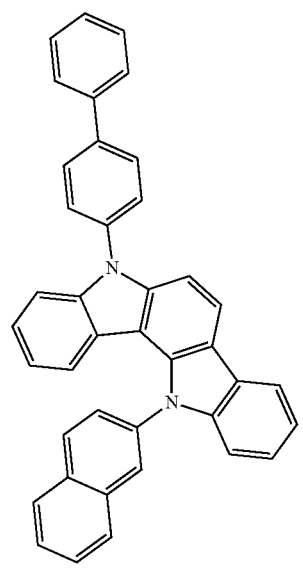
H-68
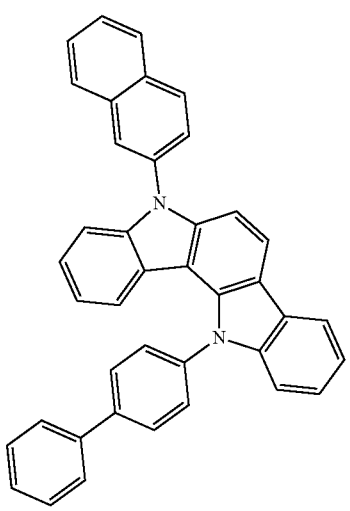

107
-continued
H-69
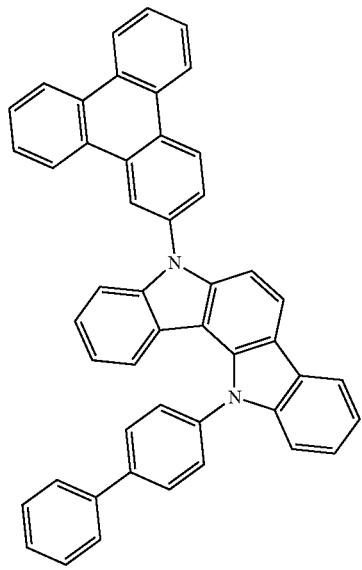
H-70
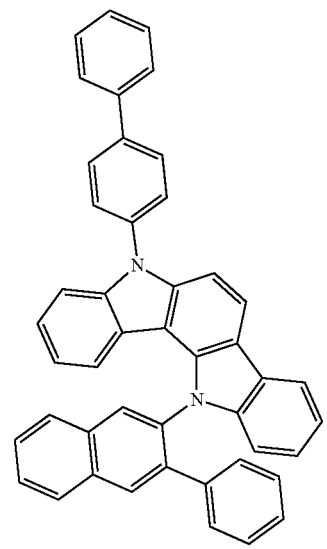
H-71
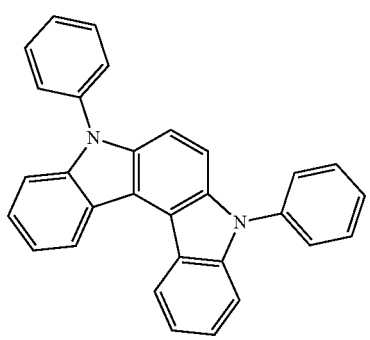
108
-continued
H-72
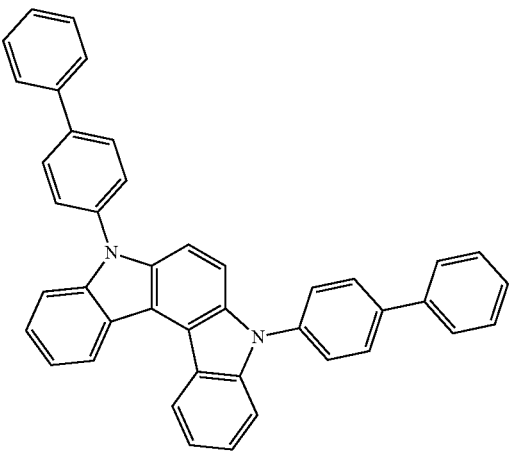
H-73
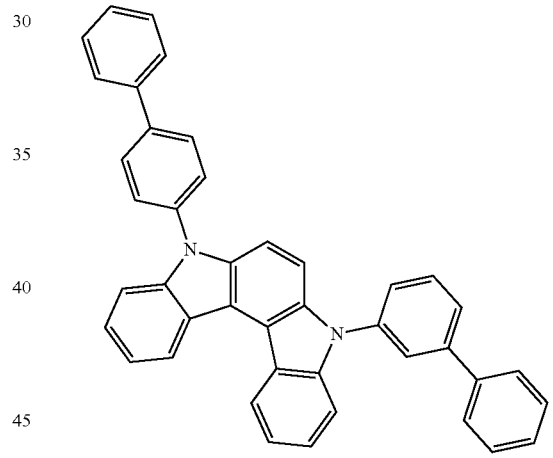
H-74
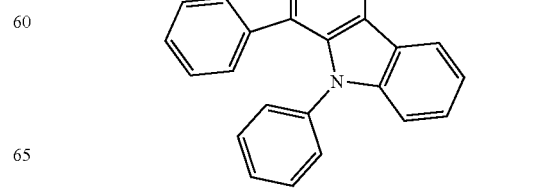

H-75
H-76
H-77
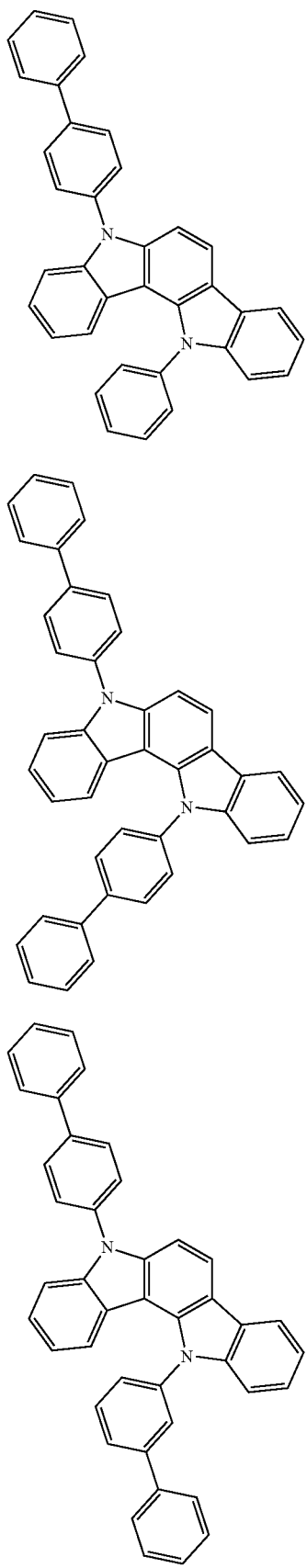
H-78
H-79
H-80
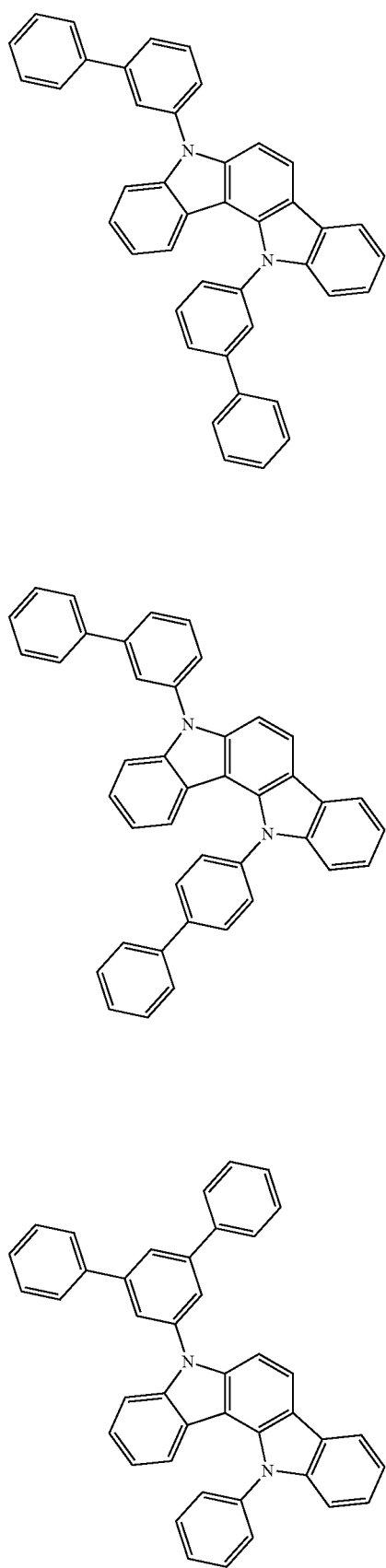

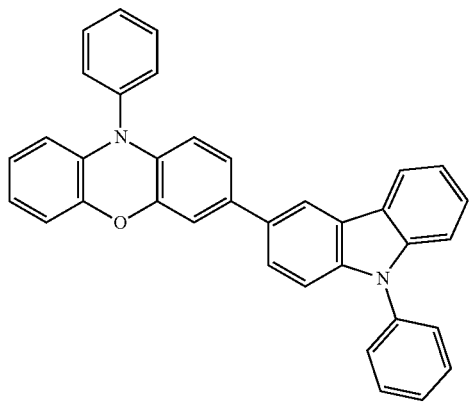

H-81

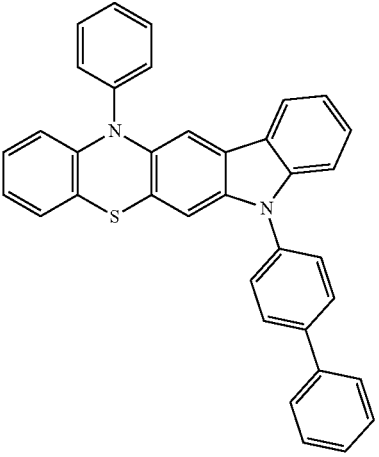

H-84

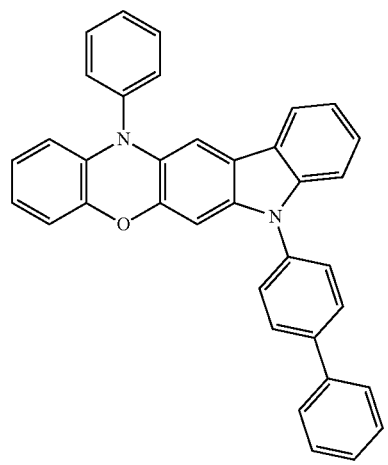

H-82

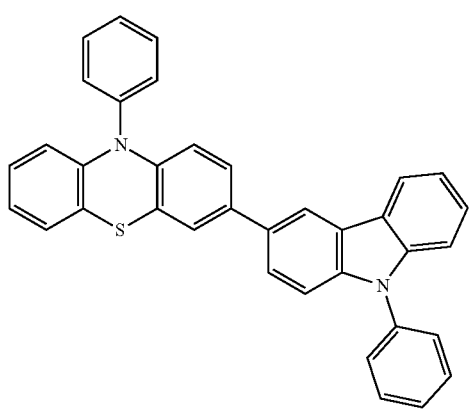

H-83

The compound of formula 11 according to the present disclosure can be prepared by referring to a synthesis method known to those skilled in the art.

Hereinafter, an organic electroluminescent device being applied to an organic electroluminescent material comprising the aforementioned organic electroluminescent compound and/or a plurality of host materials will be described.

The organic electroluminescent device according to one embodiment may comprise a first electrode; a second electrode; and at least one organic layer(s) between the first and second electrodes. The organic layer may include a light-emitting layer, and the light-emitting layer may include an organic electroluminescent compound represented by formula 1, or a plurality of host materials comprising at least one first host material(s) represented by formula 1 and at least one second host material(s) represented by formula 11.

According to one embodiment, the organic electroluminescent material of the present disclosure comprises at least one compound(s) of compounds C-1 to C-202 as the first host material represented by formula 1 and at least one compound(s) of compounds H-1 to H-84 as the second host material represented by formula 11. These plural host materials may be included in the same organic layer, for example, a light-emitting layer, or may be included in different light-emitting layers. The organic layer may further comprise at least one layer(s) selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer, in addition to a light-emitting layer.

The organic layer may further comprise an amine-based compound and/or an azine-based compound other than the light-emitting material according to the present disclosure. Specifically, the hole injection layer, the hole transport layer, the hole auxiliary layer, the light-emitting layer, the light-emitting auxiliary layer, or the electron blocking layer may contain the amine-based compound, e.g., an arylamine-based compound and a styrylarylamine-based compound, etc., as a hole injection material, a hole transport material, a hole auxiliary material, a light-emitting material, a light-emitting auxiliary material, or an electron blocking material. Also, the electron transport layer, the electron injection layer, the electron buffer layer, or the hole blocking layer may contain the azine-based compound as an electron transport material, an electron injection material, an electron buffer material, or a hole blocking material.

Also, the organic layer may further comprise at least one compound(s) selected from the group consisting of an arylamine-based compound and a styrylarylamine-based compound, and further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising such a metal.

An organic electroluminescent material according to one embodiment may be used as light-emitting materials for a white organic light-emitting device. The white organic light-emitting device has suggested various structures such as a parallel side-by-side arrangement method, a stacking arrangement method, or color conversion material (CCM) method, etc., according to the arrangement of R (Red), G (Green), YG (yellowish green), or B (blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer is a layer that is between the electron transport layer (or electron injection layer) and the light-emitting layer and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X(1 \leq X \leq 2)$, $AlO_X(1 \leq X \leq 1.5)$, SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include one or more dopants in the light-emitting layer.

The dopant comprised in the organic electroluminescent material of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary, more preferably an ortho-metallated complex compound(s) of a metal atom(s) selected from iridium (Ir), osmium (Os), copper (Cu), and platinum (Pt), as necessary, and even more preferably ortho-metallated iridium complex compound(s), as necessary.

The dopant comprised may use the compound represented by the following formula 101, but is not limited thereto:

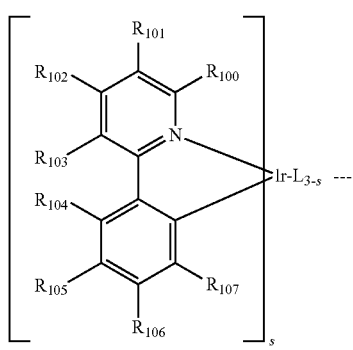

(101)

In formula 101,
L is selected from the following structure 1 or 2;

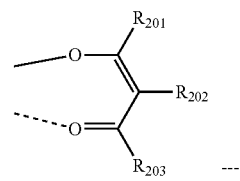

structure (1)

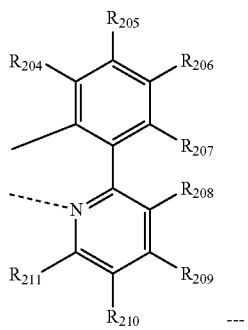

structure (2)

$R_{100}$ to $R_{103}$ each independently represent, hydrogen, deuterium, halogen, (C1-C30)alkyl unsubstituted or substituted with halogen, a substituted or unsubstituted (C3-C30)cycloalkyl, a substituted or unsubstituted (C6-C30)aryl, cyano, a substituted or unsubstituted (C3-C30) heteroaryl, or a substituted or unsubstituted (C1-C30)alkoxy; or may be linked to the adjacent substituent to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent, hydrogen, deuterium, halogen, (C1-C30)alkyl unsubstituted or substituted with halogen, a substituted or unsubstituted (C3-C30)cycloalkyl, a substituted or unsubstituted (C6-C30)aryl, a substituted or unsubstituted (C3-C30) heteroaryl, cyano, or a substituted or unsubstituted (C1-C30)alkoxy; or may be linked to the adjacent substituent to form a ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{211}$ each independently represent, hydrogen, deuterium, halogen, (C1-C30)alkyl unsubstituted or substituted with halogen, a substituted or unsubstituted (C3-C30)cycloalkyl, or a substituted or unsubstituted (C6-C30)aryl; or may be linked to the adjacent substituent to form a ring(s); and s represents an integer of 1 to 3.

Specifically, the specific examples of the dopant compound include the following, but are not limited thereto

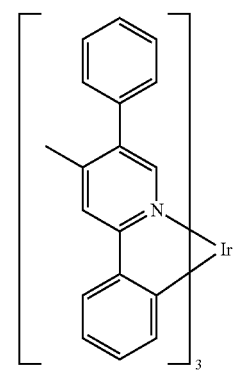

D-1

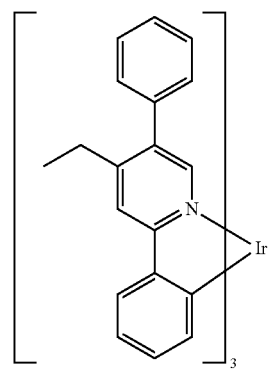

D-2

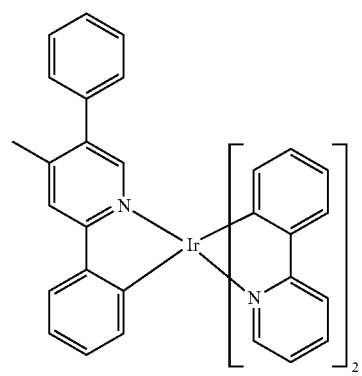

D-3

D-4
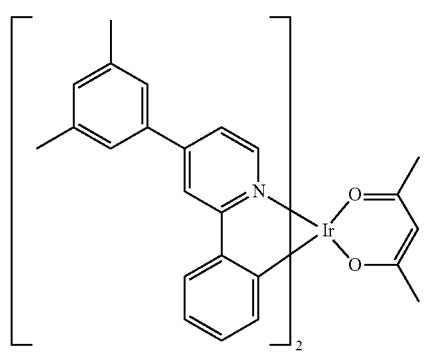
D-5
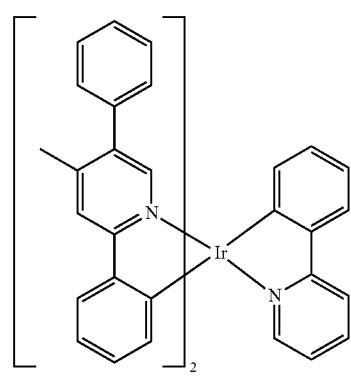
D-6
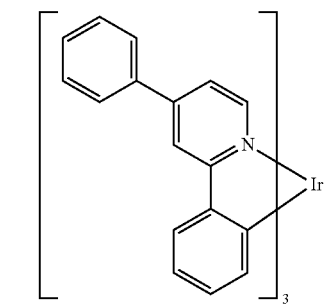
D-7
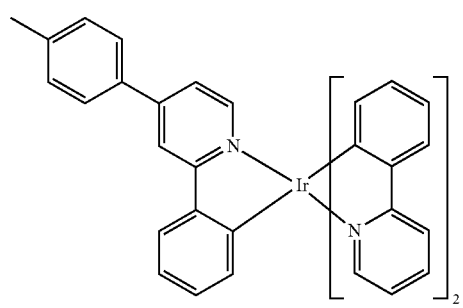
D-8
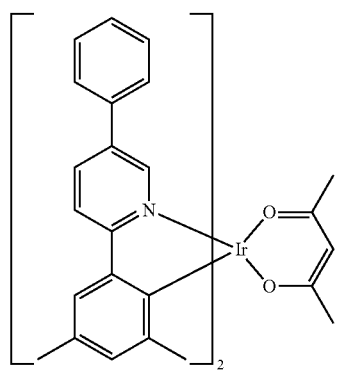
D-9
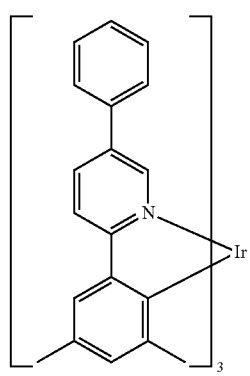
D-10
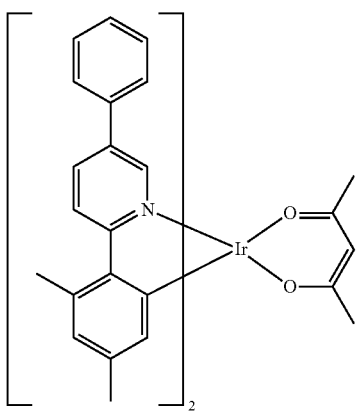
D-11
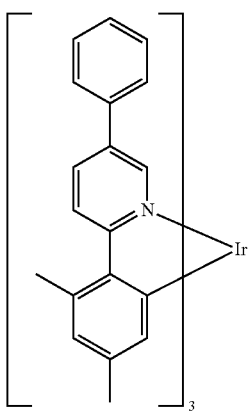

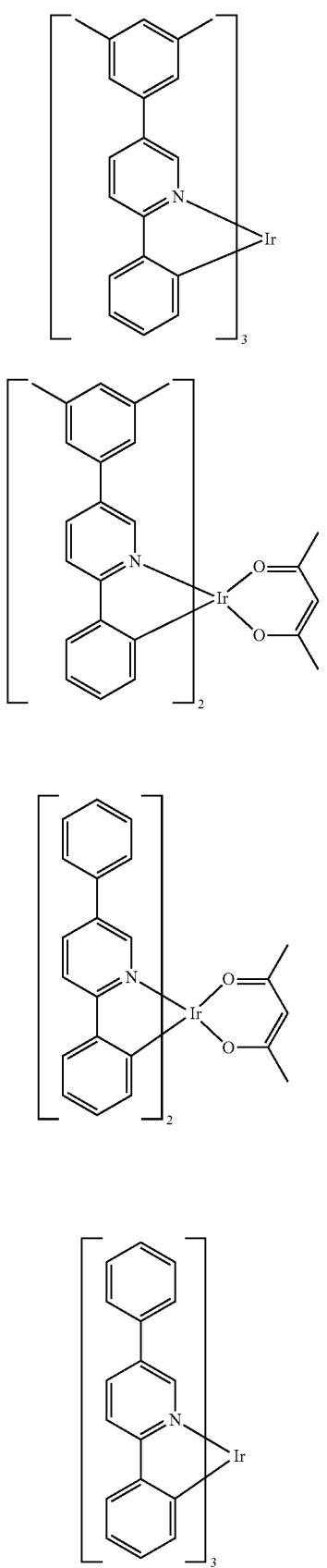

-continued
D-21
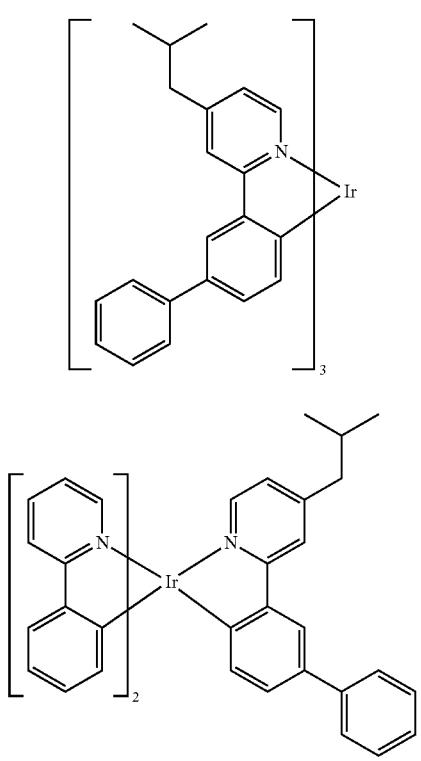
D-22
D-23
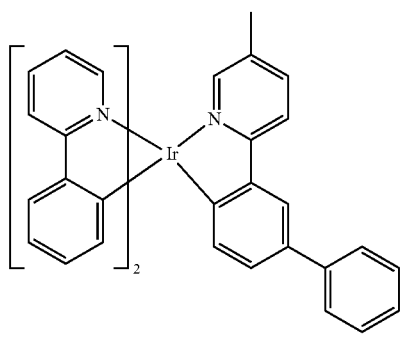
D-24
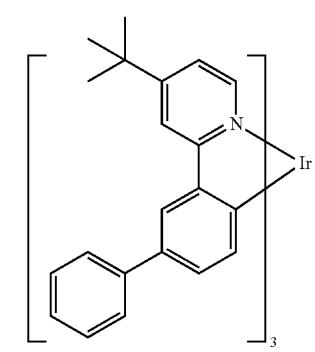
-continued
D-25
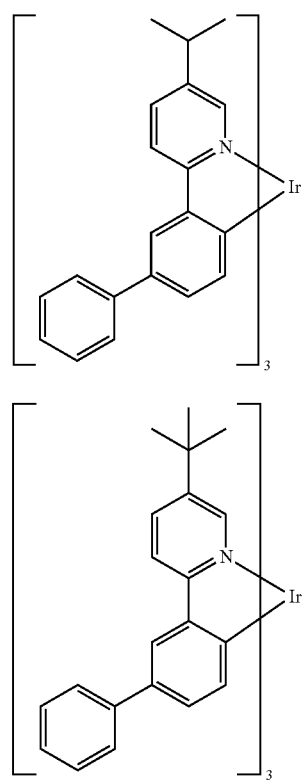
D-26
D-27
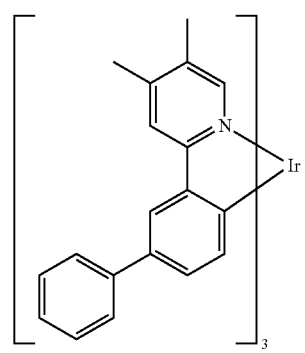
D-28
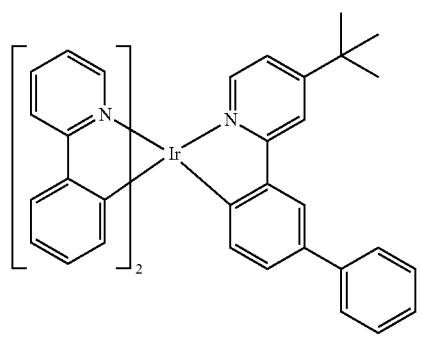

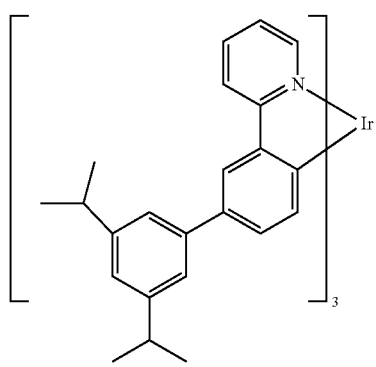
D-29
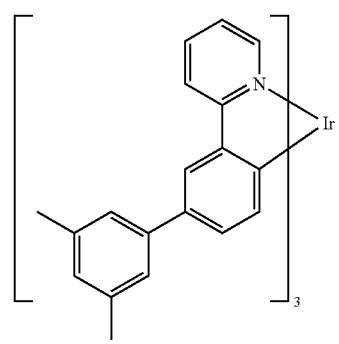
D-30
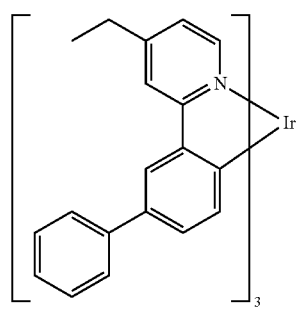
D-31
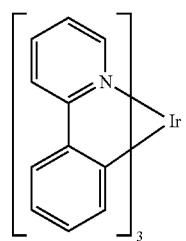
D-32
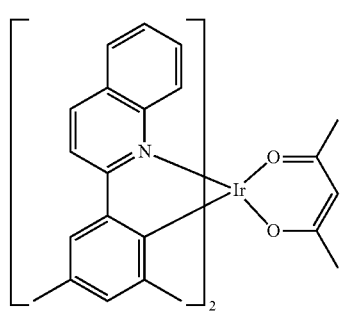
D-33
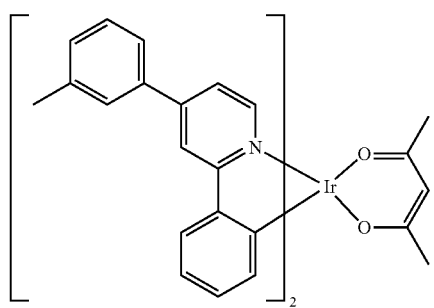
D-34
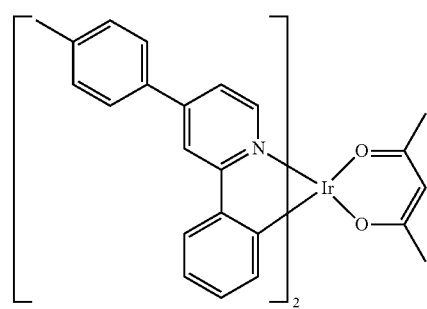
D-35
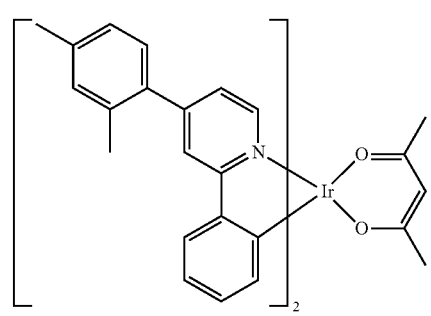
D-36
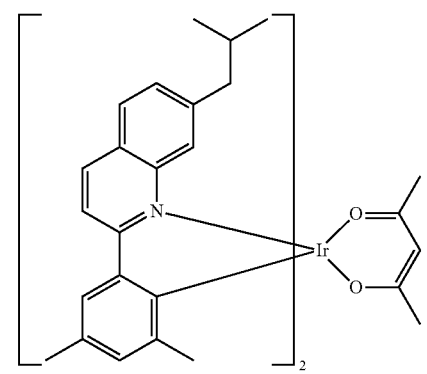
D-37
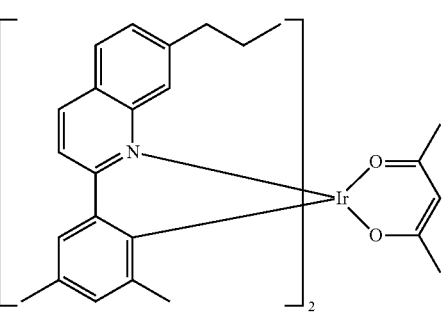
D-38

-continued
D-39
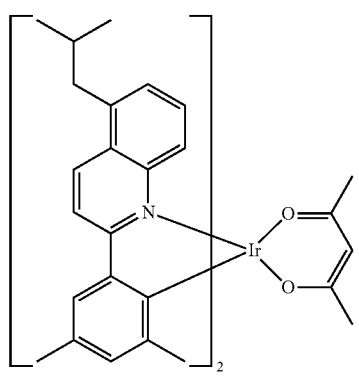
D-40
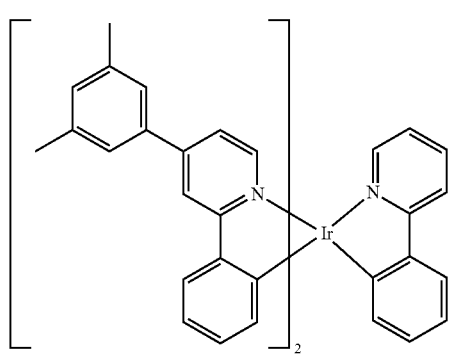
D-41
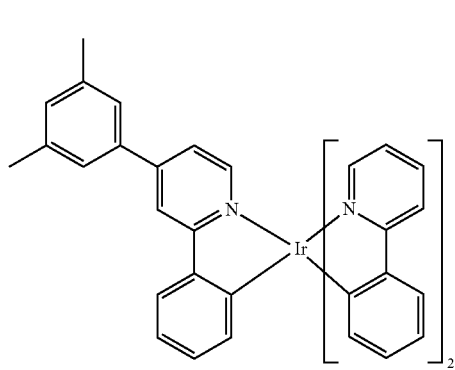
D-42
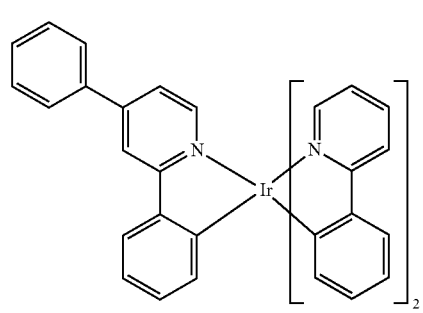
-continued
D-43
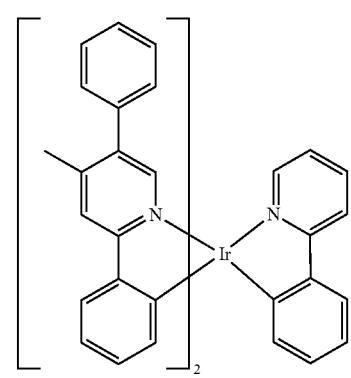
D-44
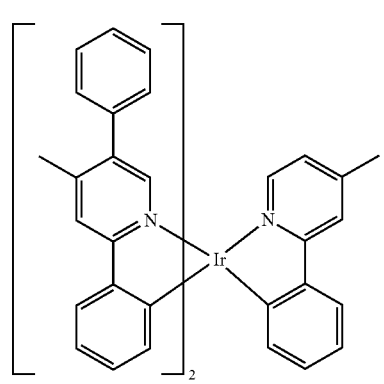
D-45
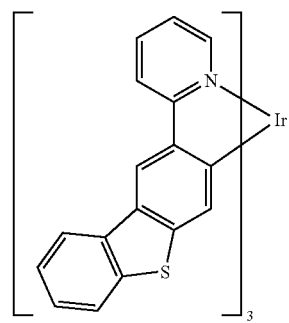
D-46
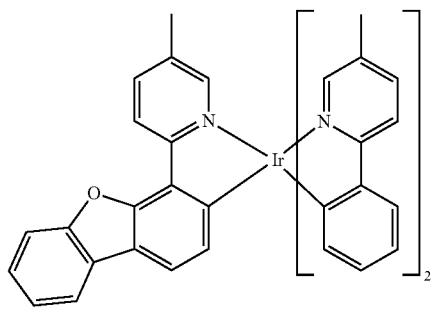

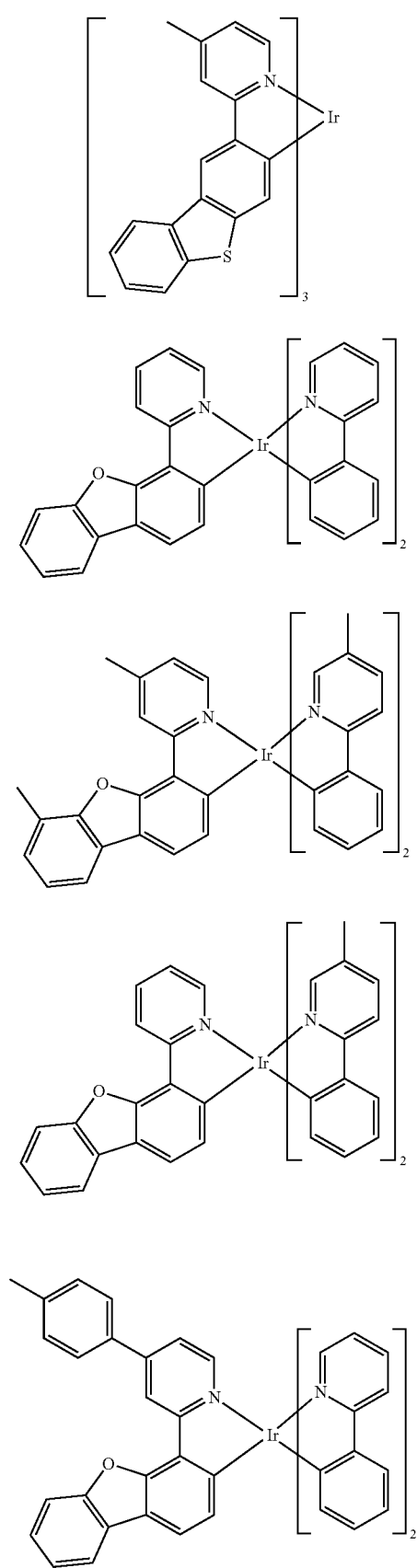

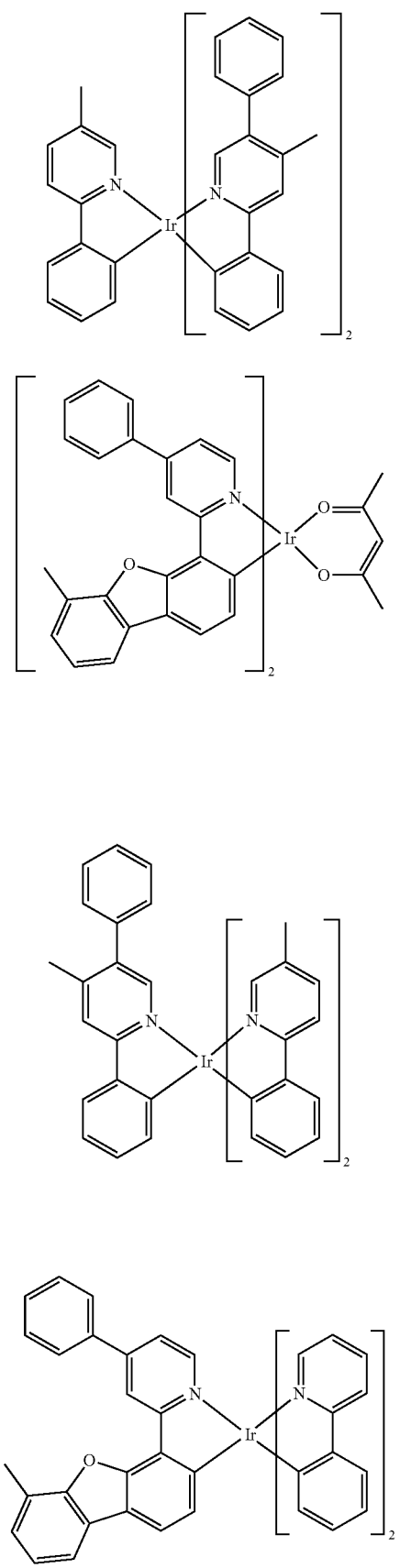

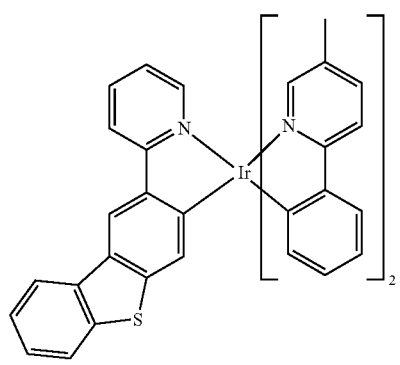
D-66
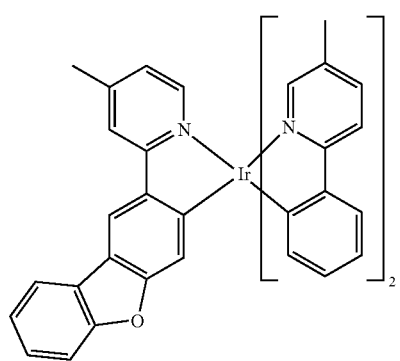
D-67
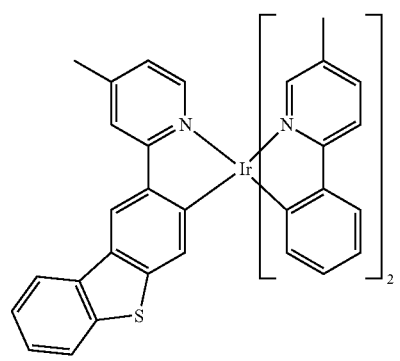
D-68
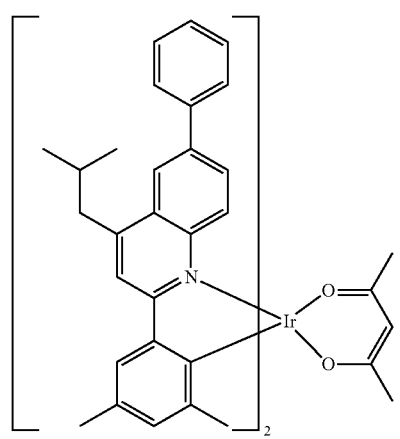
D-69
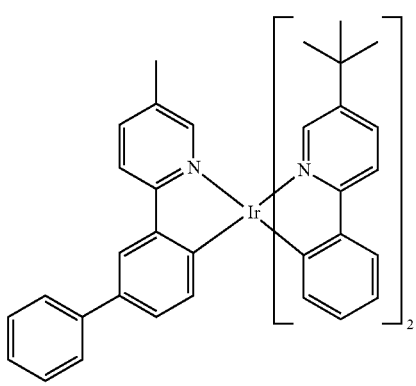
D-70
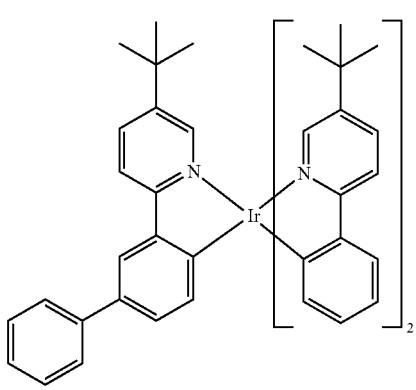
D-71
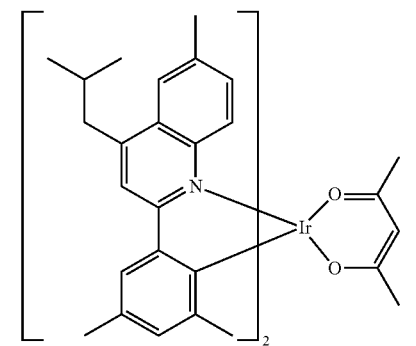
D-72
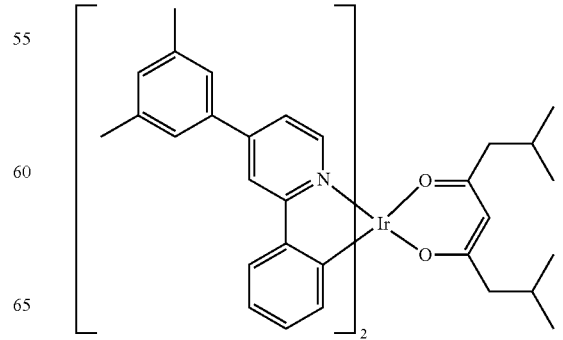
D-73

D-74
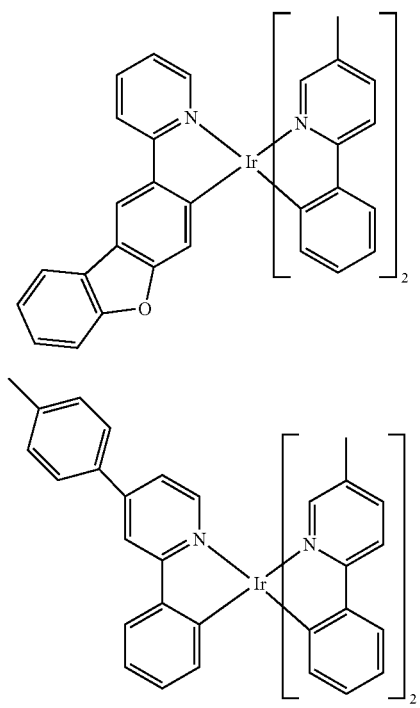
D-75
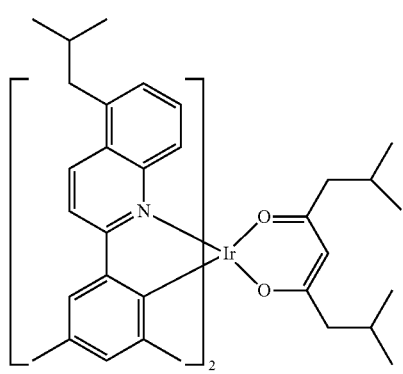
D-76
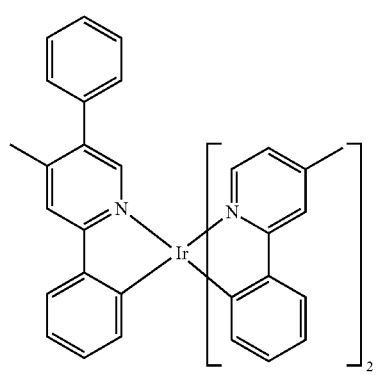
D-78
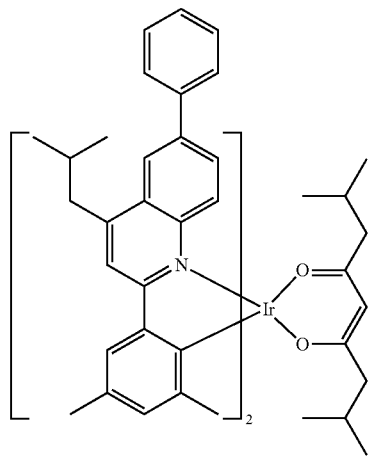
D-79
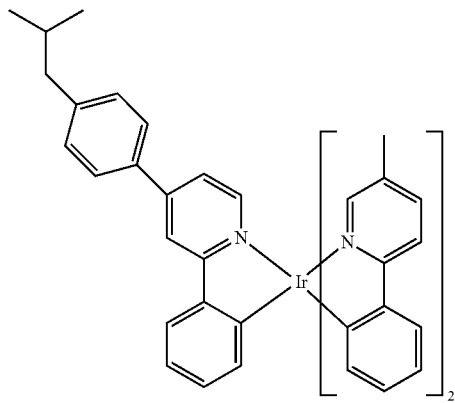
D-77
D-80
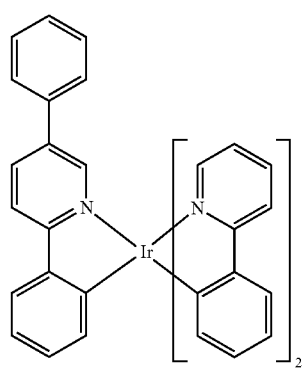

D-81
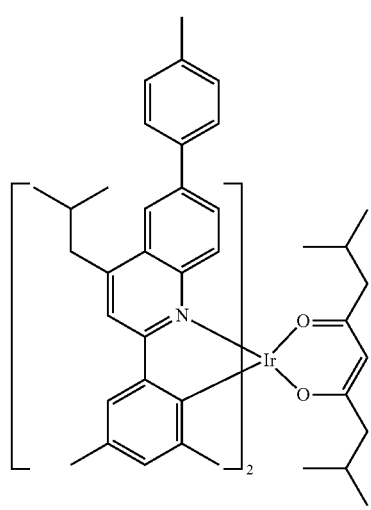
D-82
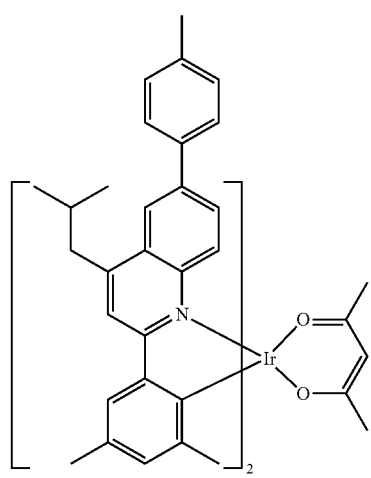
D-83
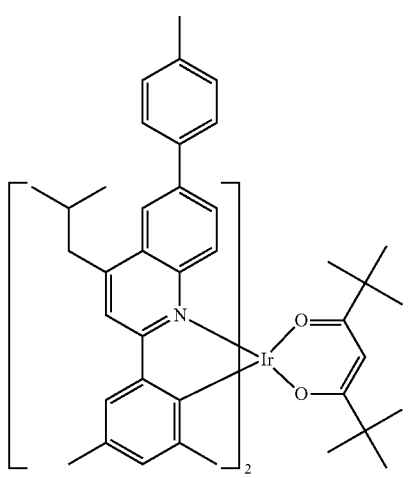
D-84
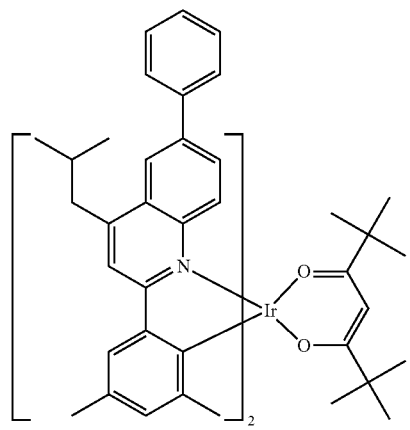
D-85
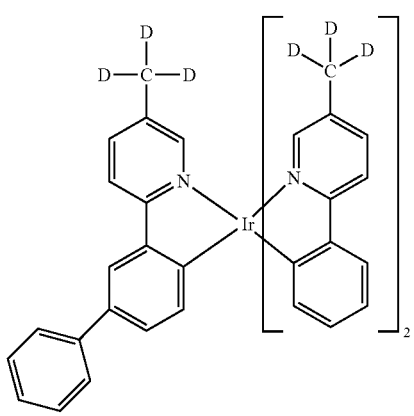
D-86
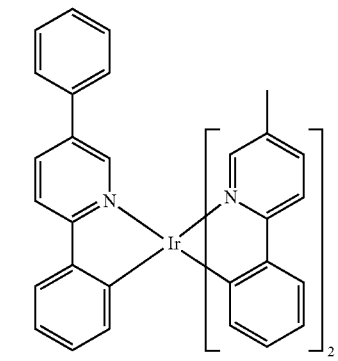
D-87
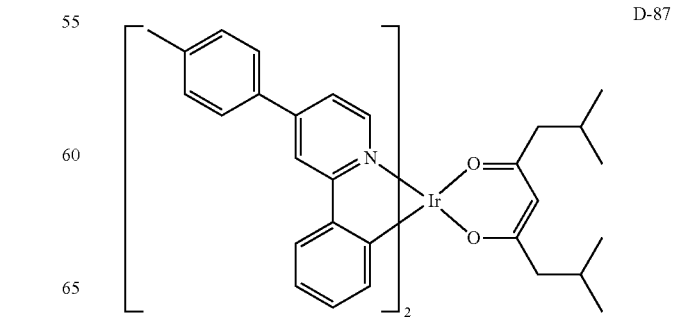

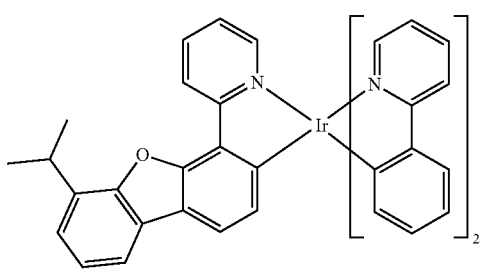
D-88
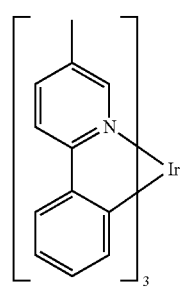
D-89
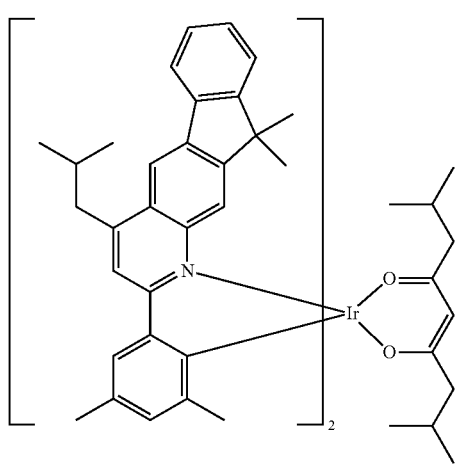
D-90
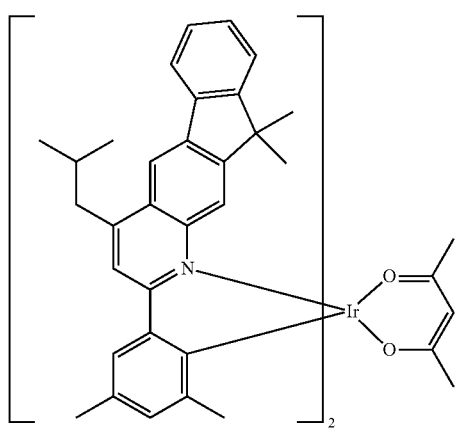
D-91
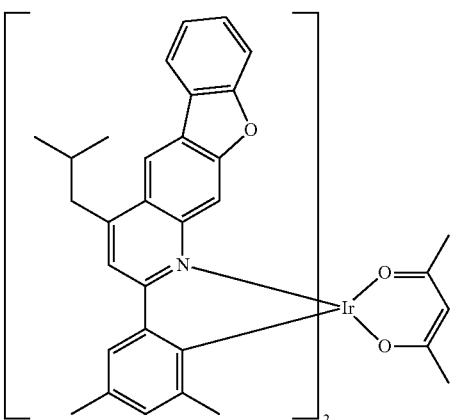
D-92, D-93, D-94

-continued
D-95
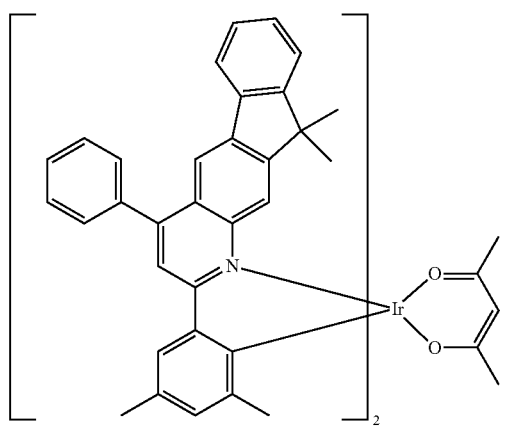
D-96
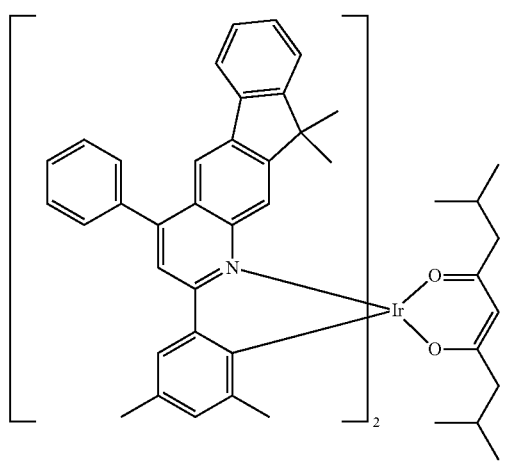
D-97
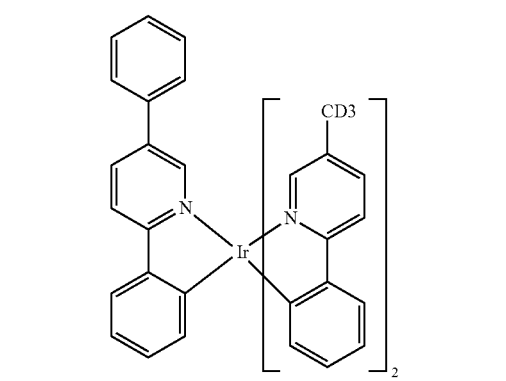
D-98
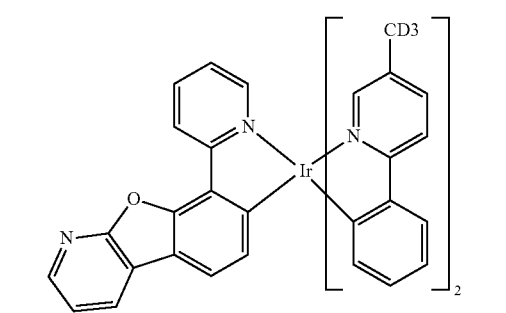
-continued
D-99
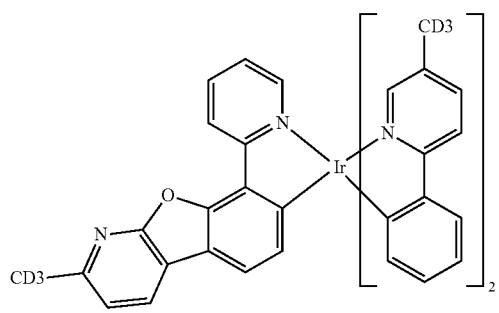
D-100
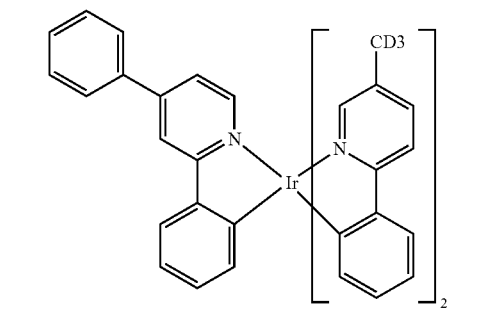
D-101
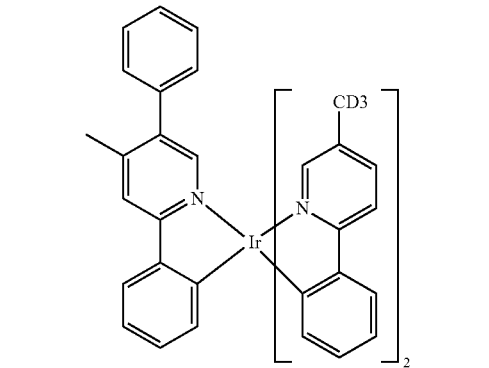
D-102
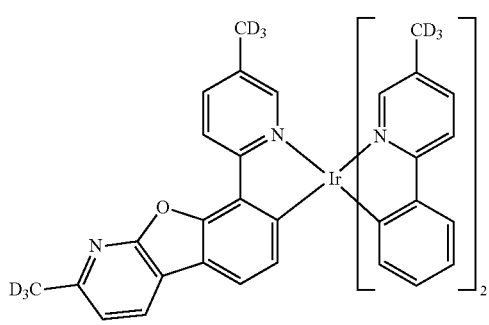
D-103
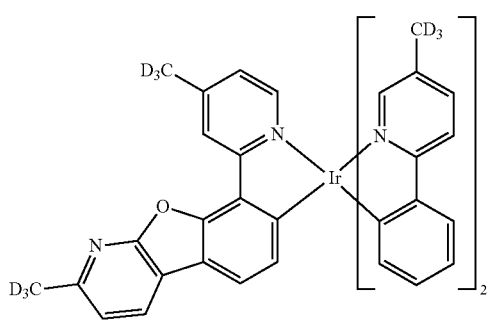

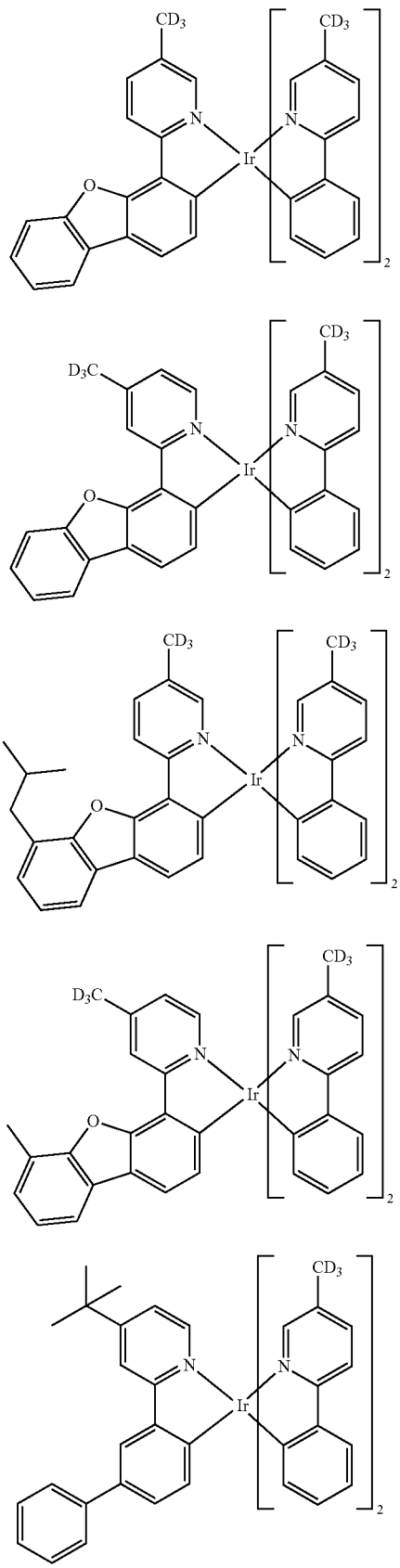
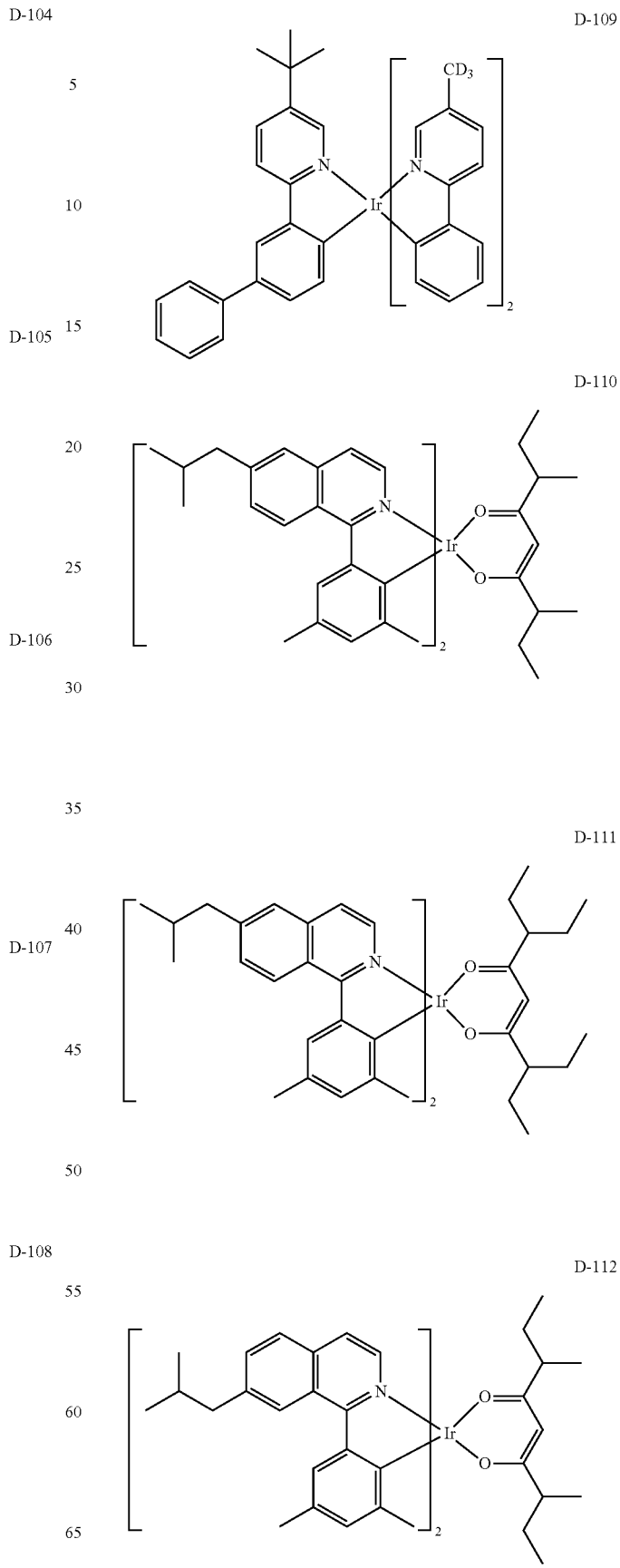

-continued

D-113
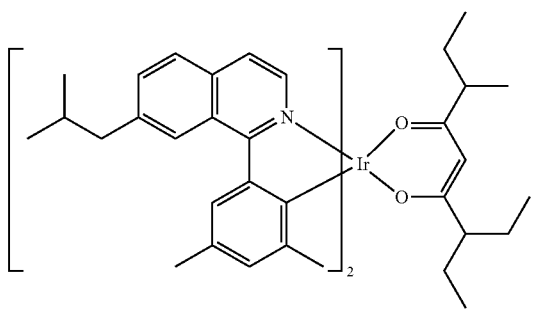

D-114
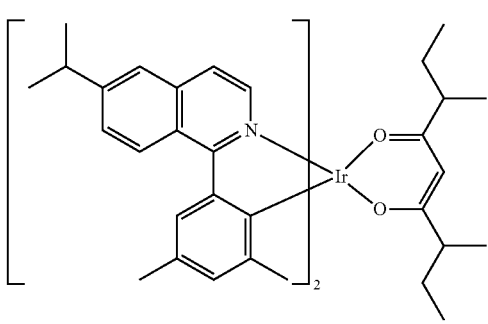

D-115
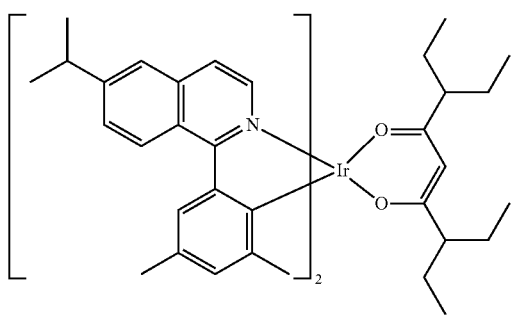

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first and second host materials according to one embodiment, the methods listed above may be used, and the layer may often be formed by co-evaporation or mixture-evaporation. The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

According to one embodiment, when the first host material and the second host material are present in the same layer or different layers in the organic electroluminescent device, each of the two host materials may be deposited individually. For example, the second host material may be deposited after the first host material is deposited.

According to one embodiment, the present disclosure can provide a display device including a plurality of host materials including a first host material represented by formula 1 and a second host material represented by formula 11. Further, the present disclosure can provide display devices such as smartphones, tablets, notebooks, PCs, TVs, or display devices for vehicles, or lighting devices such as outdoor or indoor lighting, by using an organic electroluminescent device.

Hereinafter, the preparation method of compounds according to the present disclosure will be explained with reference to the synthesis method of a representative compound or the intermediate compound of the present disclosure in order to understand the present disclosure in detail.

[Example 1] Synthesis of Compound C-1

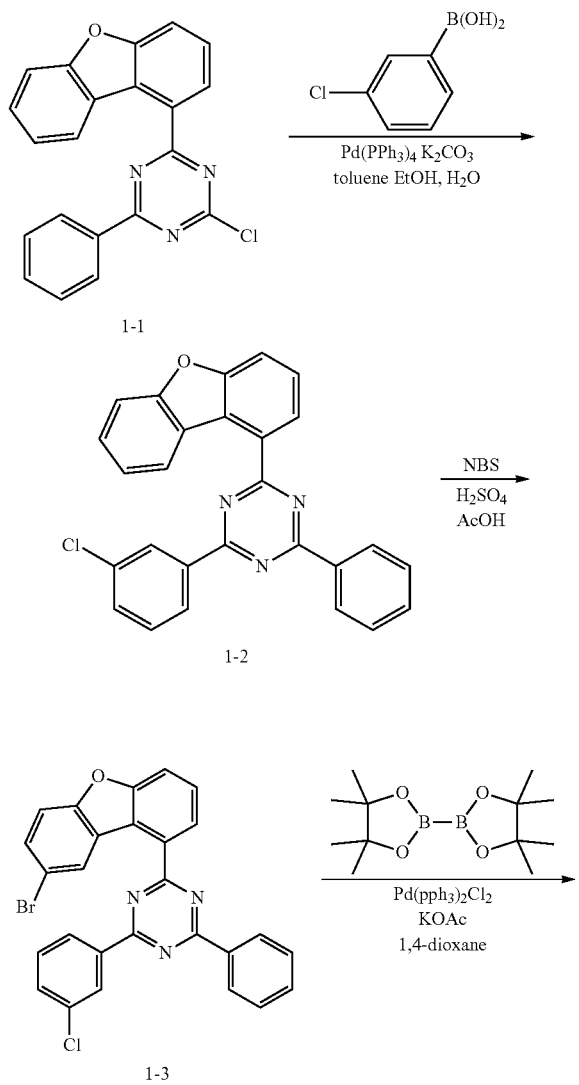

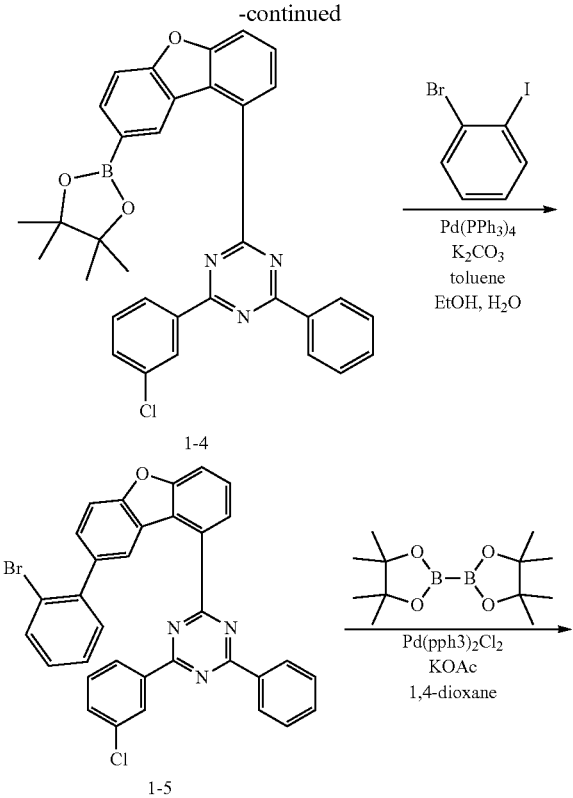

1-4

1-5

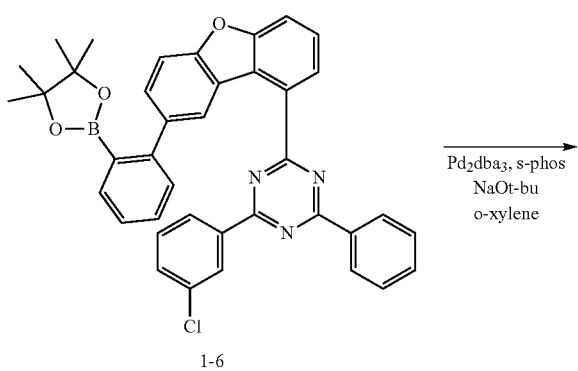

1-6

C-1

1) Preparation of Compound 1-2

Compound 1-1 (30 g, 84 mmol), (3-chlorophenyl)boronic acid (14 g, 92.2 mmol), Pd(PPh$_3$)$_4$ (4.9 g, 4.2 mmol), K$_2$CO$_3$ (23.2 g. 168 mmol), 336 mL of toluene, 84 mL of ethanol (EtOH), and 84 mL of water (H$_2$O) were added into a round bottom flask (RBF) of 3 L followed by refluxing for 1 hour at 140° C. After completion of the reaction, the reaction mixture was cooled to room temperature, and the organic layer was extracted with dichloromethane. The remaining water in the extracted organic layer was removed with MgSO$_4$ and dried. Thereafter, the organic layer was filtered and concentrated, and the resulting mixture was purified by column chromatography to obtain compound 1-2 (33 g. 90%).

2) Preparation of Compound 1-3

Compound 1-2 (33 g, 76.0 mmol), 380 mL of sulfuric acid (H$_2$SO$_4$), and 380 mL of acetic acid (AcOH) were added into a RBF of 3 L and were stirred, and then N-bromosuccinimide (NBS) (15 g, 83.6 mmol) was added thereto, followed by refluxing for 18 hours at a room temperature. After completion of the reaction, the reactant was added dropwise to water, and the resulting solid was filtered. Thereafter, the obtained solid was purified by column chromatography to obtain compound 1-3 (33 g, 85%).

3) Preparation of Compound 1-4

Compound 1-3 (30.5 g, 59.5 mmol), Bis(pinacolato) diboron) (19.5 g, 77.3 mmol). Pd(pph$_3$)$_2$Cl$_2$ (2.1 g, 13 mmol), KOAc (12 g, 119 mmol), and 600 mL of 1,4-dioxane were added into a RBF of 2 L followed by refluxing for 3 hours at 140° ° C. After completion of the reaction, the reaction mixture was cooled to room temperature, and the organic layer was extracted with dichloromethane. The remaining water in the extracted organic layer was removed with MgSO$_4$ and dried. Thereafter, the organic layer was filtered and concentrated, and the resulting mixture was purified by column chromatography to obtain compound 1-4 (28.4 g, 85%).

4) Preparation of Compound 1-5

Compound 1-4 (36.4 g, 65 mmol), 2-bromo iodobenzene (37 g, 130 mmol), Pd(PPh$_3$)$_4$ (3.8 g, 3.25 mmol), K$_2$CO$_3$ (18 g, 130 mmol), 520 mL of toluene, 65 mL of EtOH, and 65 mL of H$_2$O were added into a RBF of 2 L, followed by refluxing for 3 days at 140° C. After completion of the reaction, the reaction mixture was cooled to room temperature, and the organic layer was extracted with dichloromethane. The remaining water in the extracted organic layer was removed with MgSO$_4$ and dried. Thereafter, the organic layer was filtered and concentrated, and the resulting mixture was purified by column chromatography to obtain compound 1-5 (21 g, 54%).

5) Preparation of Compound 1-6

Compound 1-5 (21 g. 36 mmol), bis(pinacolato)diboron) (13.5 g. 53 mmol), Pd(pph$_3$)$_2$Cl$_2$ (1.3 g, 1.8 mmol), KOAc (7.1 g, 72 mmol), and 360 mL of 1,4-dioxane were added into a RBF of 1 L followed by refluxing for 3 hours at 140° C. After completion of the reaction, the mixture was filtered through Celite filter and the organic layer was concentrated. The mixture was purified by column chromatography to obtain compound 1-6 (10.5 g, 44%).

6) Preparation of Compound C-1

Compound 1-6 (10 g, 16 mmol), Pd$_2$db$_3$ (7.3 g, 8 mmol), S-phos (6.4 g. 16 mmol), NaOt-bu (3.1 g, 32 mmol), and 390 mL of o-xylene were added into a RBF of 1 L followed by refluxing for 6 hours at 160° C. After completion of the reaction, the mixture was filtered through Celite filter and the organic layer was concentrated. The mixture was purified by column chromatography to obtain compound C-1 (1 g. 13%).

Hereinafter, the preparation method and the light-emitting properties of an organic electroluminescent device comprising an organic electroluminescent compound of the present disclosure will be explained in order to understand the present disclosure in detail.

[Device Example 1] Preparation of OLED Comprising the Compound According to the Present Disclosure as a Host An OLED comprising the compound according to the present disclosure was produced. First, a transparent electrode indium tin oxide (ITO) thin film (10 Ω/sq) on a glass substrate for an OLED device (GEOMATEC CO., LTD., Japan) was subject to an ultrasonic washing with acetone and isopropyl alcohol, sequentially, and then was stored in isopropanol and used. The ITO substrate was then mounted on a substrate holder of a vacuum vapor deposition apparatus. Next, compound HI-1 as a first hole injection compound was introduced into a cell of the vacuum vapor deposition apparatus, and compound HT-1 as a first hole transport compound was introduced into another cell. Thereafter, the two materials were evaporated at different rate, and the first hole injection compound was doped in a doping amount of 3 wt % with respect to the total amount of the first hole injection compound and the first hole transport compound to form a first hole injection layer having a thickness of 10 nm. Next, compound HT-1 was deposited to form a first hole transport layer having a thickness of 80 nm on the first hole injection layer. Next, compound HT-2 was introduced into another cell of the vacuum vapor deposition apparatus. Thereafter, an electric current was applied to the cell to evaporate the introduced material, thereby forming a second hole transport layer having a thickness of 30 nm on the first hole transport layer. After forming the hole injection layer and the hole transport layers, a light-emitting layer was then deposited thereon as follows: Each of the host materials listed the following Table 1 was introduced into two cells of the vacuum vapor depositing apparatus as hosts, and compound D-50 was introduced into another cell as a dopant. The two host materials were evaporated at a different rate of 2:1 and simultaneously, the dopant was evaporated at different rate and was deposited in a doping amount of 10 wt % with respect to the total amount of the host and dopant to form a light-emitting layer having a thickness of 40 nm on the second hole transport layer. Next, compounds ETL-1 and EIL-1 as electron transport materials were deposited in a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. Each compound was purified by vacuum sublimation under 10-6 torr and then used.

[Device Example 2] Preparation of OLED Comprising the Compound According to the Present Disclosure as a Host OLED was produced in the same manner as in Device Example 1, except that compound C-1 was used solely as the host of the light-emitting material.

[Comparative Example 1] Preparation of OLED Comprising the Conventional Compound as a Host OLED was produced in the same manner as in Device Example 1, except that as light-emitting materials, a light-emitting layer having a thickness of 40 nm was deposited on the second hole transport layer by using compound CBP as a host and compound D-50 as a dopant; BAlq as a hole blocking layer having a thickness of 5 nm was deposited; Next, ETL-1 and EIL-1 were evaporated at a weight ratio of 40:60, and were deposited to form an electron transport layer having a thickness of 30 nm on the hole blocking layer.

The results of the driving voltage, the luminous efficiency, and the light-emitting color at a luminance of 1,000 nits, and the time taken to reduce from 100% to 95% at a luminance of 20,000 nits (lifespan; T95), of the organic electroluminescent devices of Device Examples 1 and 2, and Comparative Example 1 produced as described above, are shown in the following Table 3.

TABLE 1

| Host Materials | | | | | Life- |
|---|---|---|---|---|---|
| First Host Material | Second Host Material | Driving Voltage (V) | Luminous Efficiency (cd/A) | Light-Emitting Color | span (T95, hr) |
| Device Example 1 | C-1 | H-2 | 2.8 | 82.6 | Green | 134.2 |
| Device Example 2 | C-1 | — | 3.0 | 80.3 | Green | 7.0 |
| Comparative Example 1 | CBP | — | 5.6 | 72.0 | Green | 0.5 |

Referring to the Table 1 above, it was confirmed that the organic electroluminescent device including the organic electroluminescent compound according to the present disclosure as host materials exhibits lower driving voltage, high luminous efficiency, and long lifespan characteristics compared to an organic electroluminescent device using a conventional sole host material.

The compounds used in Device Examples 1 and 2, and Comparative Example 1 above are shown in the following Table 2.

TABLE 2
Hole Injection Layer/
Hole Transport Layer
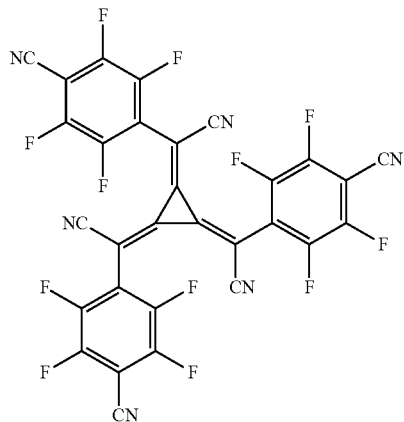 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]
HI-1
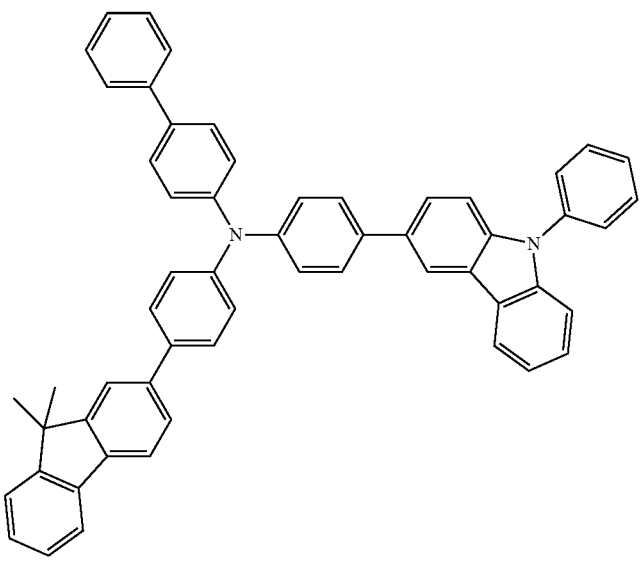 [SMILES: CC1(C)c2ccccc2-c2ccc(-c3ccc(N(c4ccc(-c5ccccc5)cc4)c4ccc(-c5ccc6c(c5)c5ccccc5n6-c5ccccc5)cc4)cc3)cc21]
HT-1
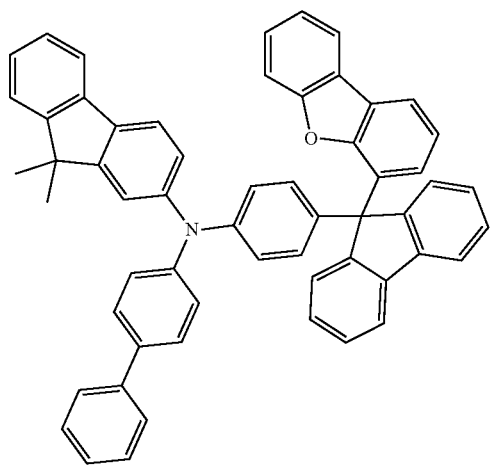 [SMILES: CC1(C)c2ccccc2-c2ccc(N(c3ccc(-c4ccccc4)cc3)c3ccc(C4(c5cccc6c5oc5ccccc56)c5ccccc5-c5ccccc54)cc3)cc21]
HT-2

TABLE 2-continued
Light-
Emitting
Layer
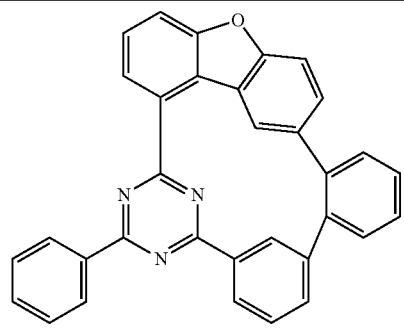
C-1
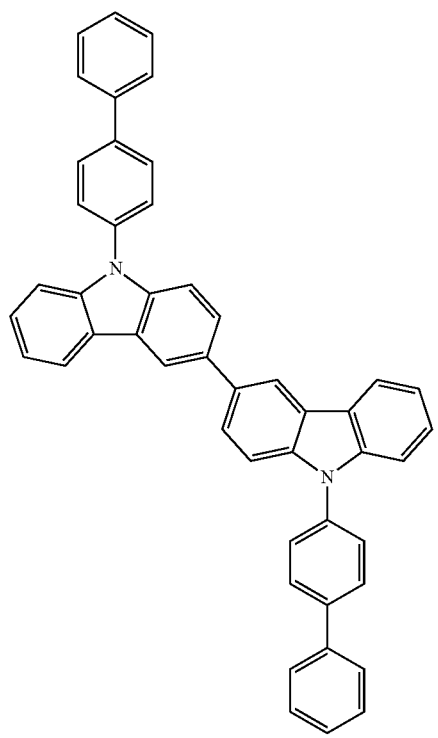 [SMILES: c1ccc(-c2ccc(-n3c4ccccc4c4cc(-c5ccc6c(c5)c5ccccc5n6-c5ccc(-c6ccccc6)cc5)ccc43)cc2)cc1]
H-2

TABLE 2-continued
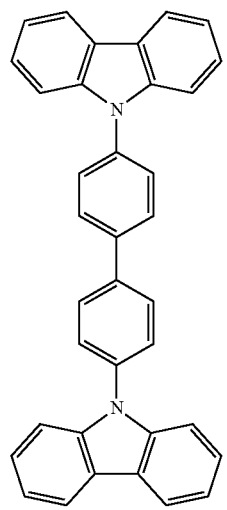 [SMILES: c1ccc2c(c1)c1ccccc1n2-c1ccc(-c2ccc(-n3c4ccccc4c4ccccc43)cc2)cc1]
CBP
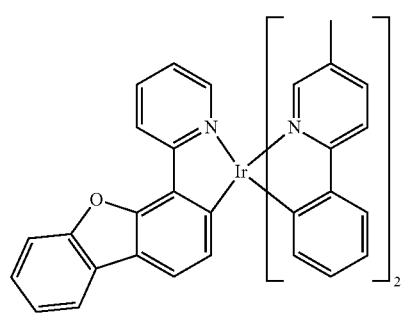
D-50
Electron Transport Layer/ Electron Injection Layer
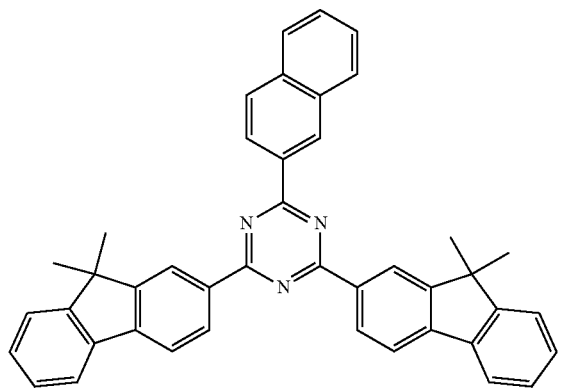 [SMILES: CC1(C)c2ccccc2-c2ccc(-c3nc(-c4ccc5c(c4)C(C)(C)c4ccccc4-5)nc(-c4ccc5ccccc5c4)n3)cc21]
ETL-1
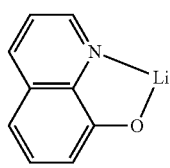
EIL-1

2. In Claim 8, the formula (12). The formular appearing in Column 163, from Line 6 to Line 20:
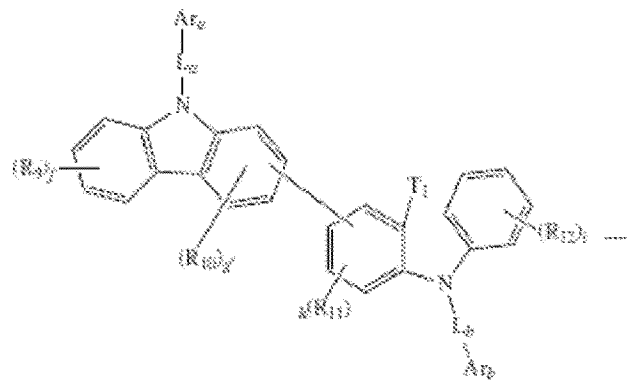
Should be:
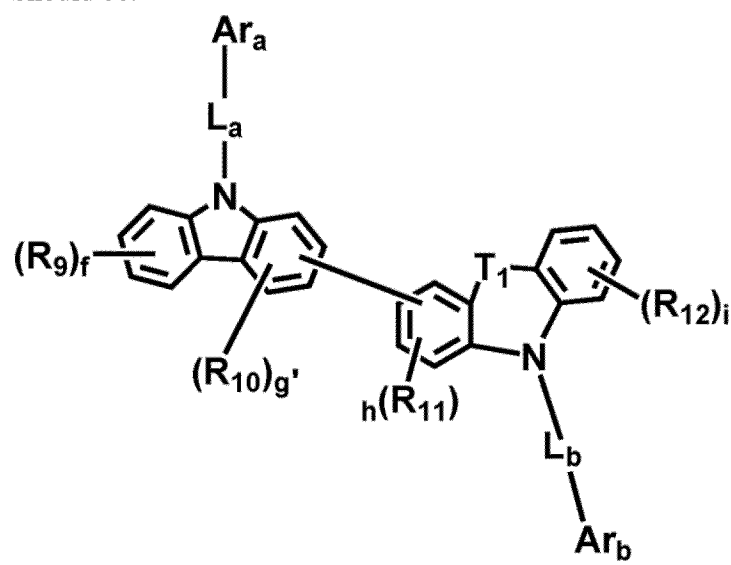

The invention claimed is:

1. An organic electroluminescent compound represented by the following formula 1:

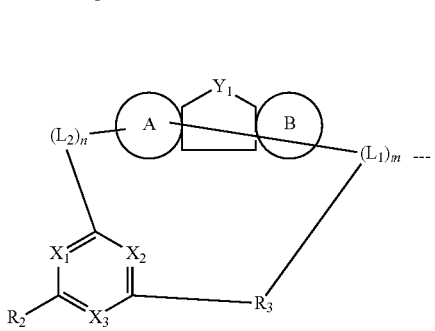
(1)

wherein,

A ring and B ring each independently represent an unsubstituted (C6-C30)aryl;

$X_1$ to $X_3$ each independently represent N;

$R_2$ represents an unsubstituted (C6-C30)aryl;

$L_1$ and $R_3$ each independently represent an unsubstituted (C6-C30)arylene;

$L_2$ represents a single bond;

$Y_1$ represents —O—; and m and n each independently represent an integer of 1.

2. The organic electroluminescent compound according to claim 1, wherein

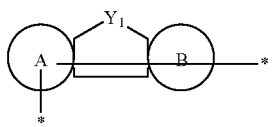

in the formula (1) is represented by the following formula 1-1:

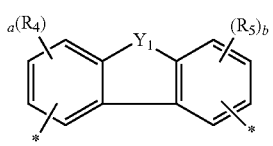
(1-1)

wherein, $Y_1$ is as defined in claim 1;

$R_4$ to $R_5$ are hydrogen;

a and b each independently represent 3.

3. The organic electroluminescent compound according to claim 2, wherein

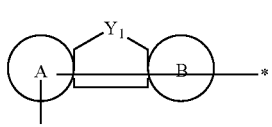

in formula (1) is represented by the following formula 1-14:

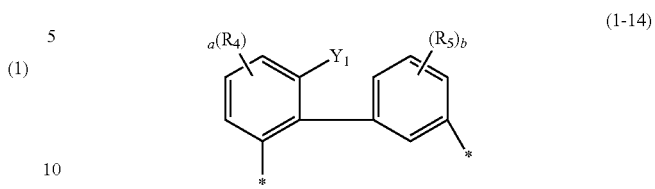
(1-14)

wherein, $R_4$, $R_5$, $Y_1$, and a to b are as defined in claim 2.

4. The organic electroluminescent compound according to claim 1, wherein the compounds represented by the formula 1 are selected from the following compounds:

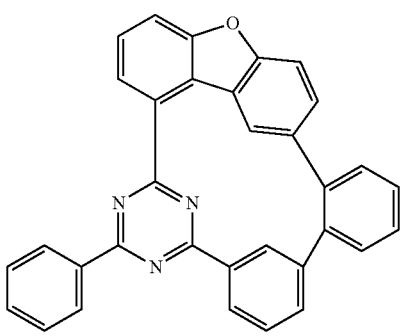
C-1

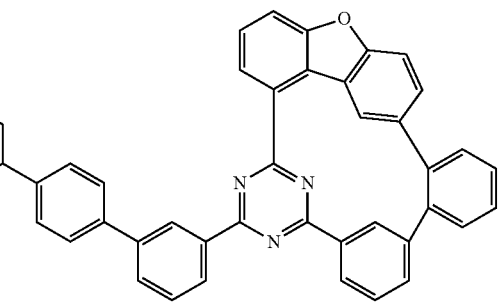
C-2

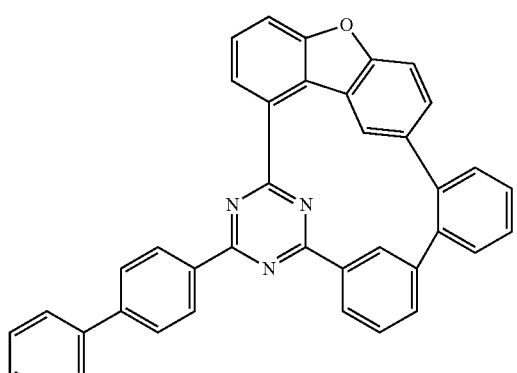
C-3

C-4
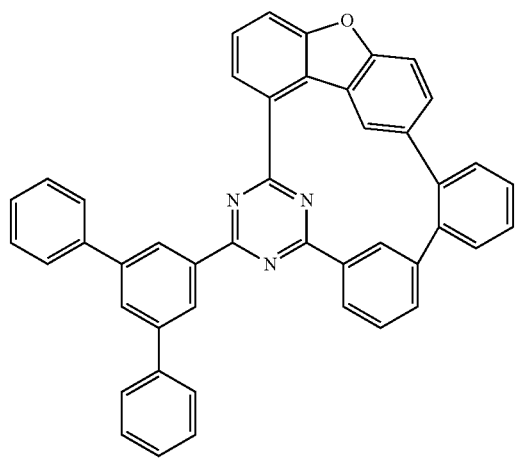
C-5
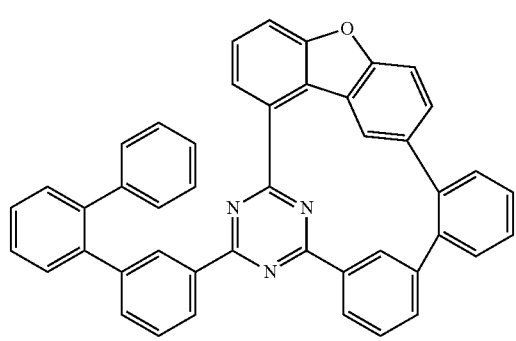
C-10
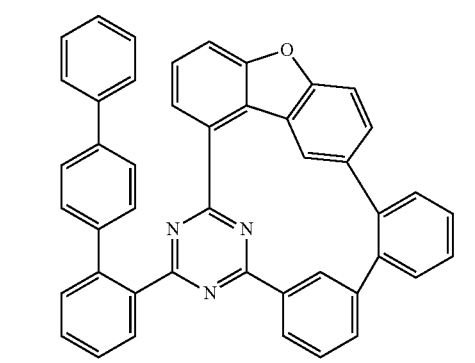
C-13
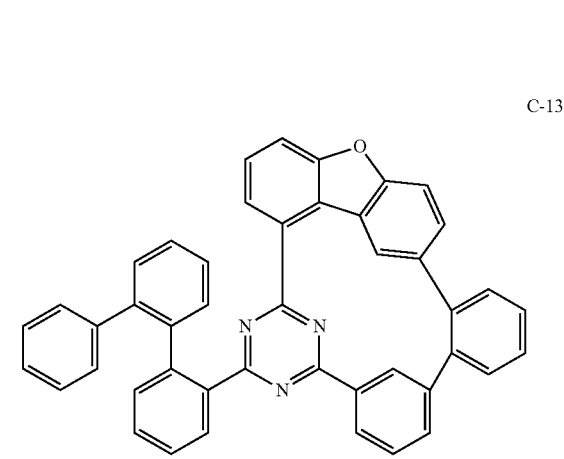
C-14
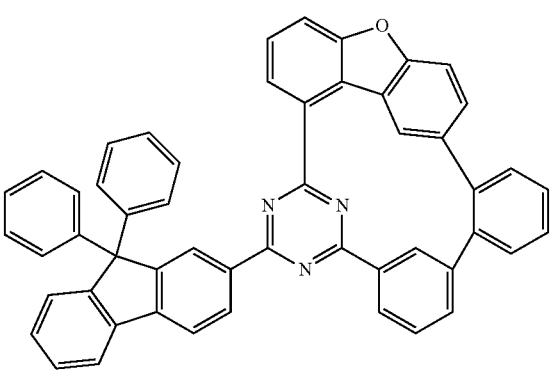
C-15
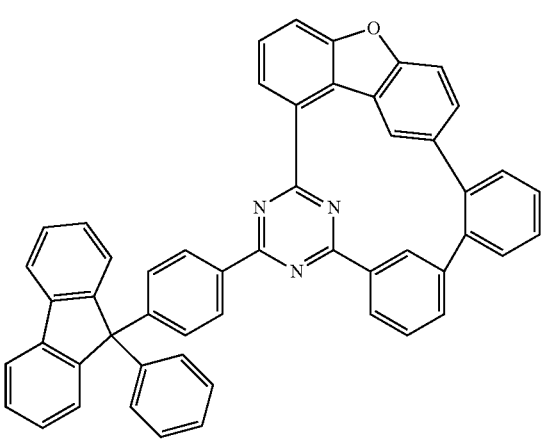
C-21
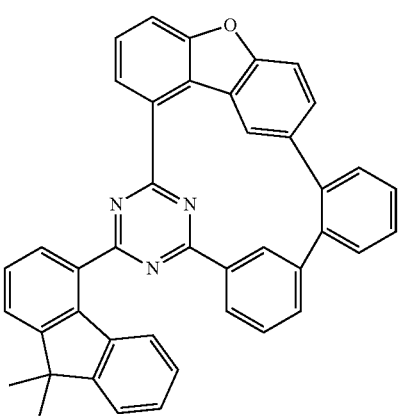

C-22
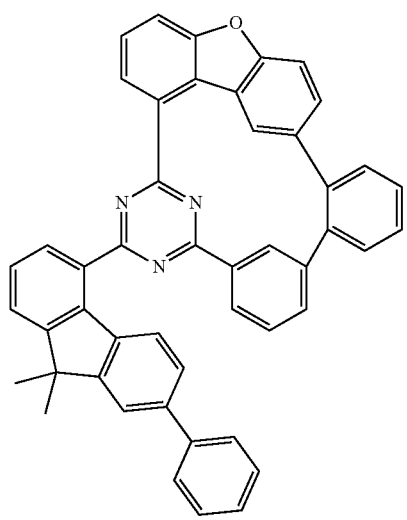
C-30
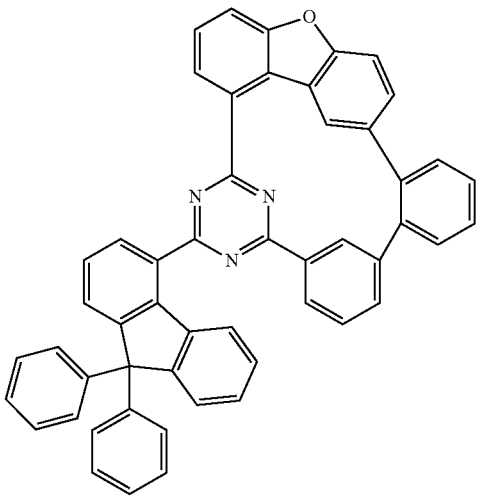
C-25
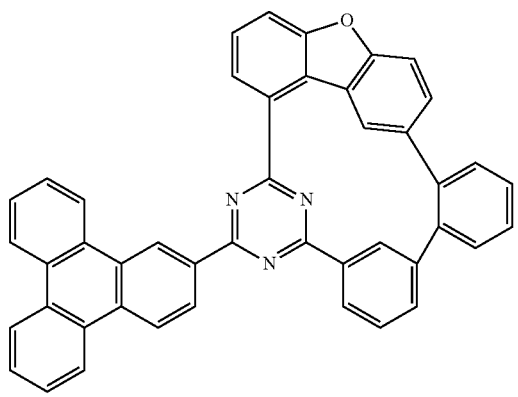
C-31
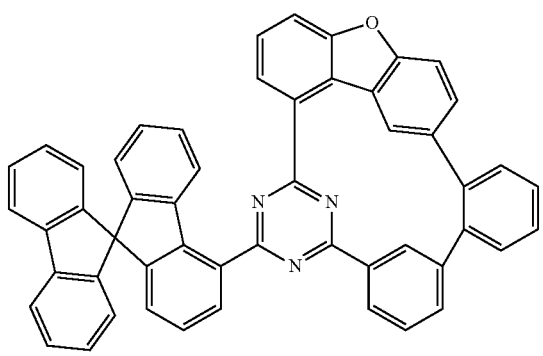
C-28
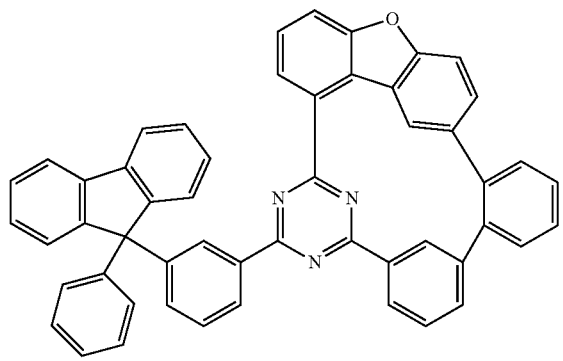
C-34
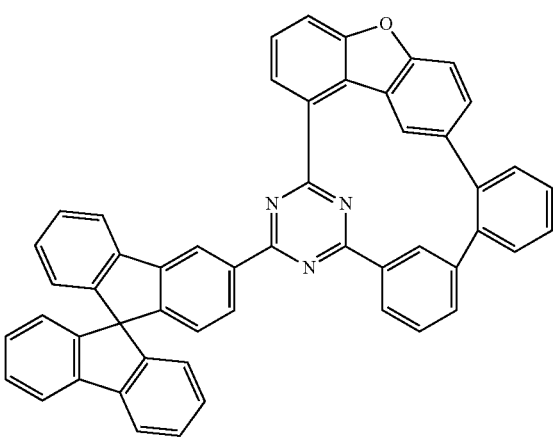

-continued

C-35

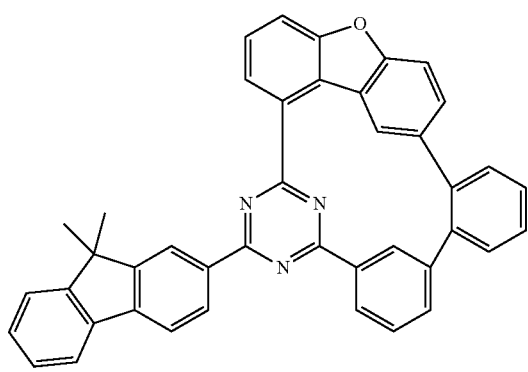

C-41

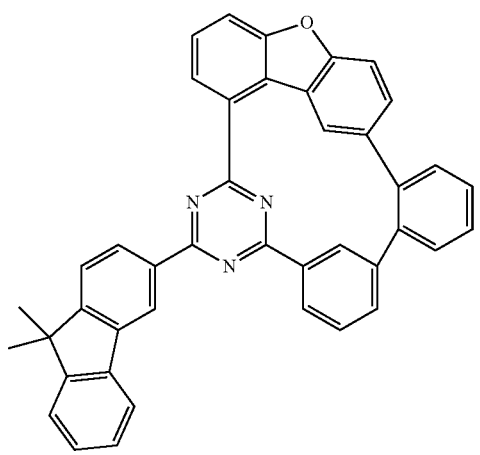
and

C-42

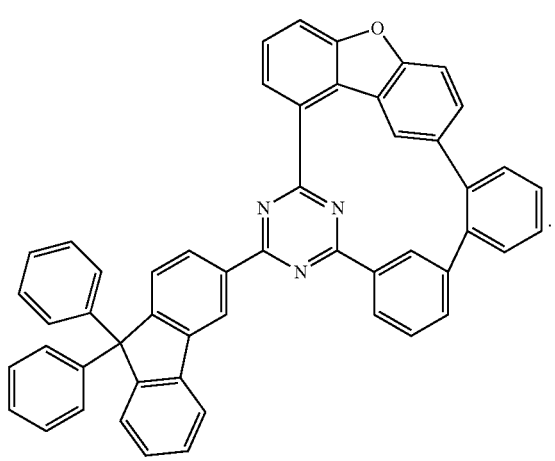

5. An organic electroluminescent material comprising the organic electroluminescent compound according to claim 1.

6. A plurality of host materials comprising at least one of the organic electroluminescent material(s) according to claim 5 as a first host material, and at least one of a second host material which is different from the first host material.

7. The plurality of host materials according to claim 6, wherein the second host material comprises a compound represented by the following formula 11:

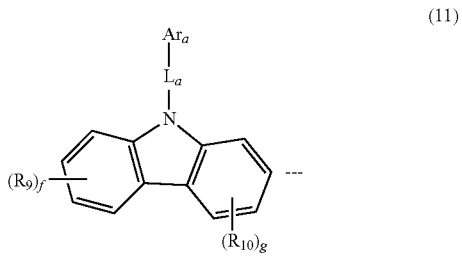

(11)

wherein, $L_a$ represents a single bond, a substituted or unsubstituted (C6-C30)arylene, or a substituted or unsubstituted (3- to 30-membered)heteroarylene;

$Ar_a$ represents a substituted or unsubstituted (C6-C30) aryl, or a substituted or unsubstituted (3- to 30-membered)heteroaryl;

$R_9$ and $R_{10}$ each independently represent hydrogen, deuterium, halogen, cyano, a substituted or unsubstituted (C1-C30)alkyl, a substituted or unsubstituted (C6-C30) aryl, or a substituted or unsubstituted (3- to 50-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of an (C3-C30) aliphatic ring and an (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or may be linked to an adjacent substituent to form a ring(s);

f and g each independently represents an integer of 1 to 4; and when f and g are 2 or more, each of $R_9$ and each of $R_{10}$ may be the same or different.

8. The plurality of host materials according to claim 7, wherein the compound represented by formula 11 is represented by the following formula 12 or 13:

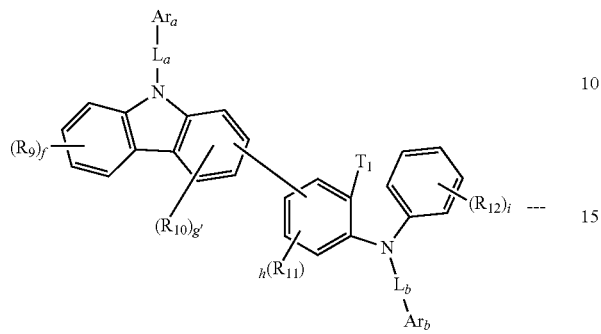
(12)

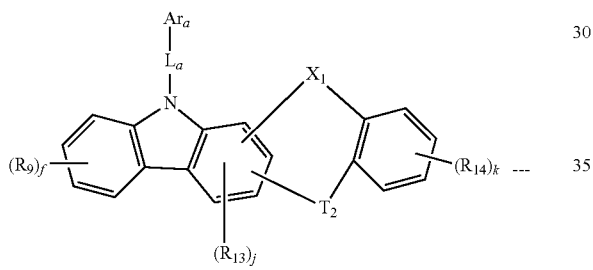
(13)

wherein, $L_a$, $Ar_a$, $R_9$, $R_{10}$, and f, and g are as defined in claim 7;

$T_1$ and $T_2$ each independently represent a single bond, O, or S;

$L_b$ is defined as $L_a$ in claim 7;

$Ar_b$ is defined as $Ar_a$ in claim 7;

$R_{11}$ to $R_{14}$ each independently are as defined as $R_9$ in claim 7;

$X_1$ represents O, S, or $NR_a$;

$R_a$ represents a substituted or unsubstituted (C6-C30)aryl;

g' and h each independently represent an integer of 1 to 3, i and k each independently represent an integer of 1 to 4, and j represents an integer of 1 or 2; and when g', h, i, j, and k are 2 or more, each of R10, each of R11, each of R12, each of R13, and each of R14 may be the same or different.

9. The plurality of host materials according to claim 7, wherein the compound represented by the formula 11 are selected from the following compounds:

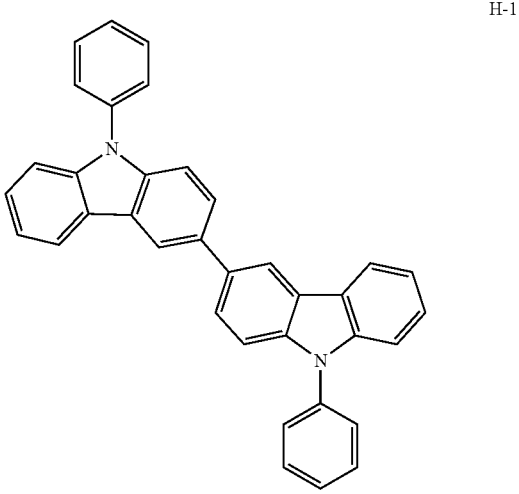
H-1

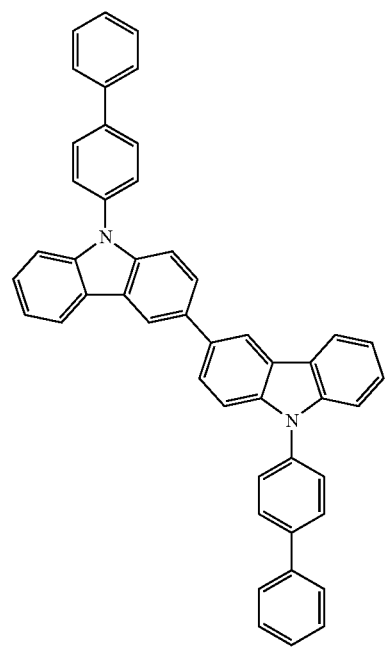
H-2

H-3
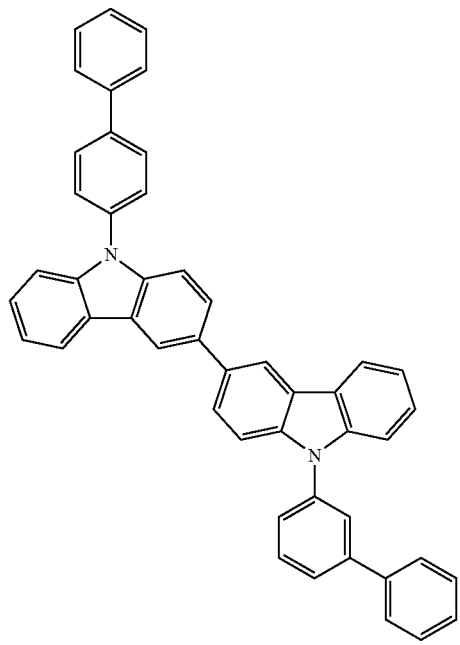
H-4
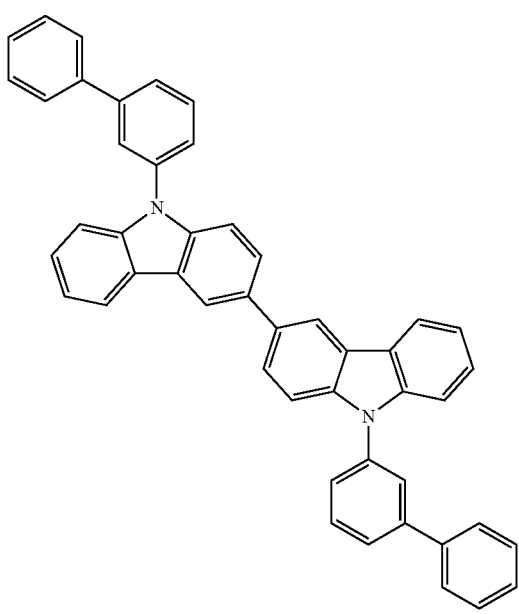
H-5
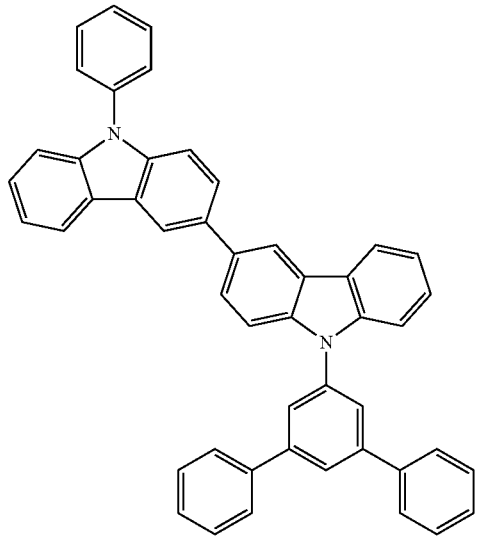
H-6
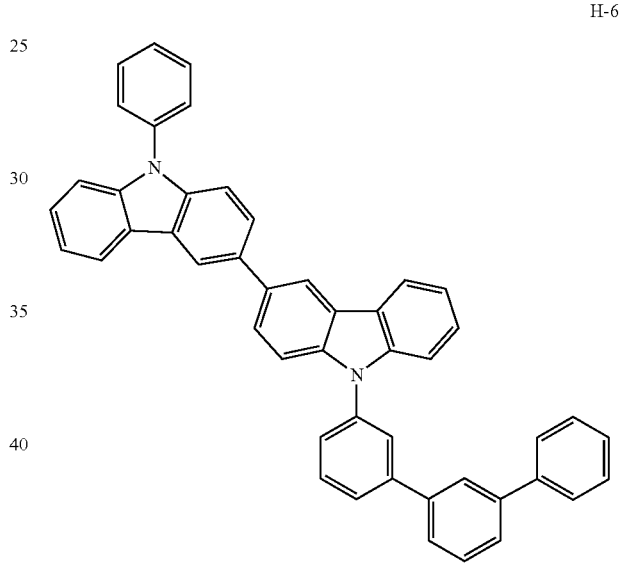
H-7
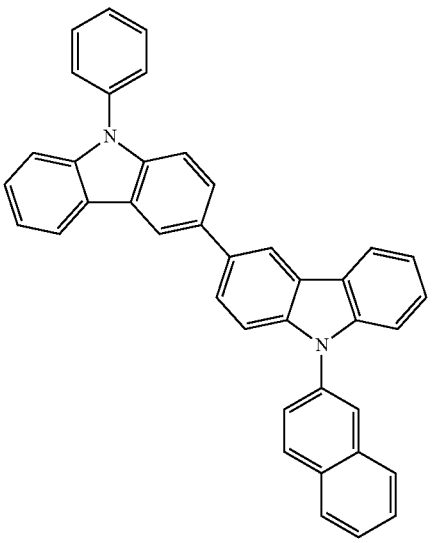

H-8
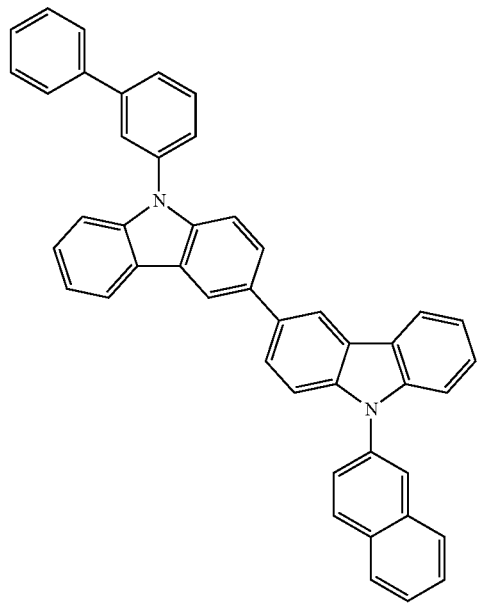
H-9
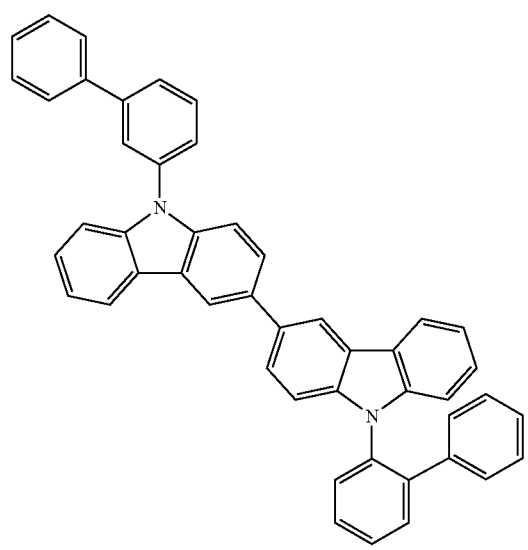
H-10
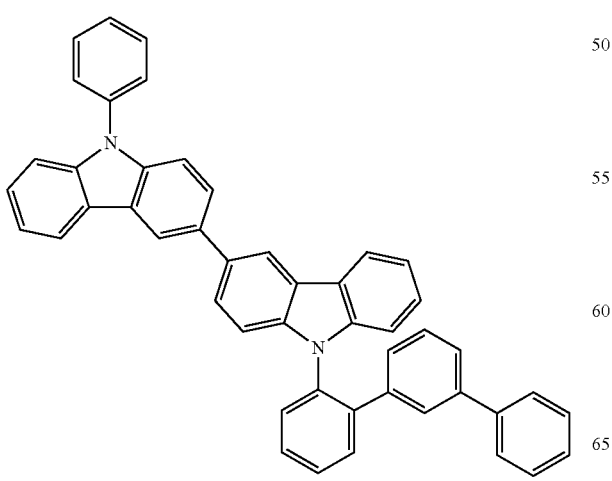
H-11
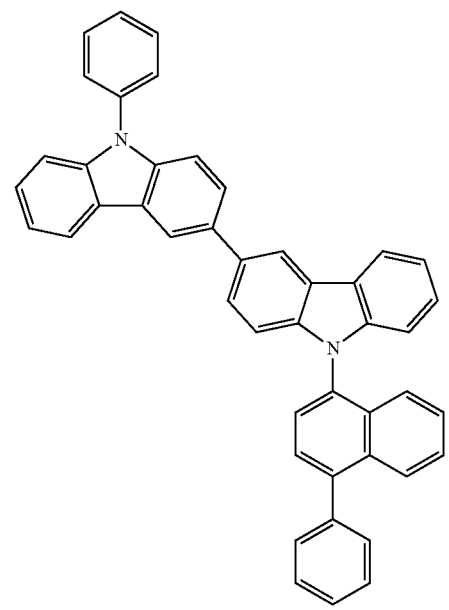
H-12

H-13
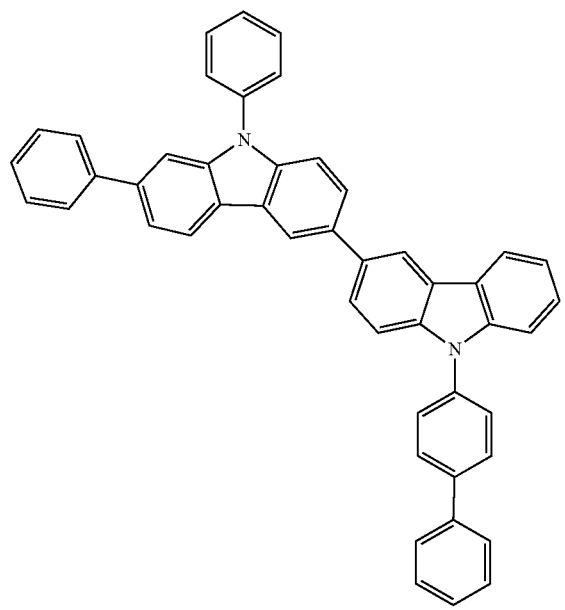
H-15
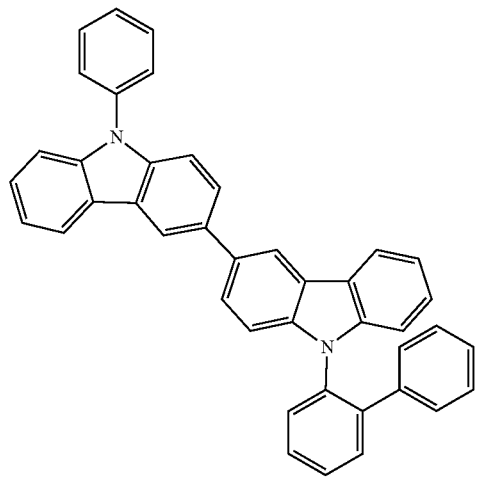
H-16
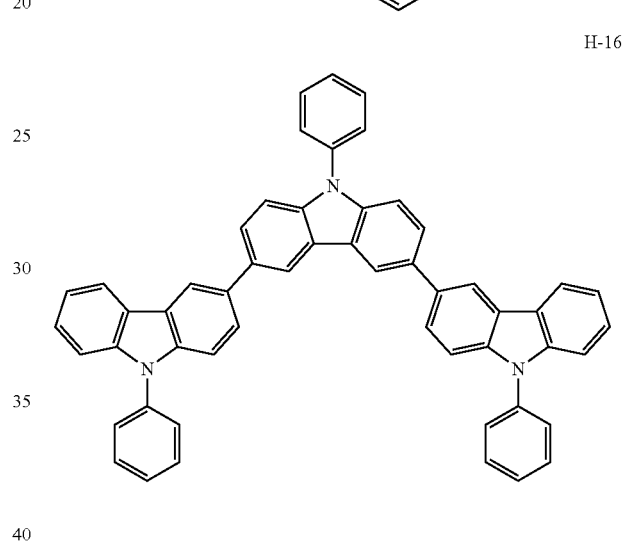
H-14
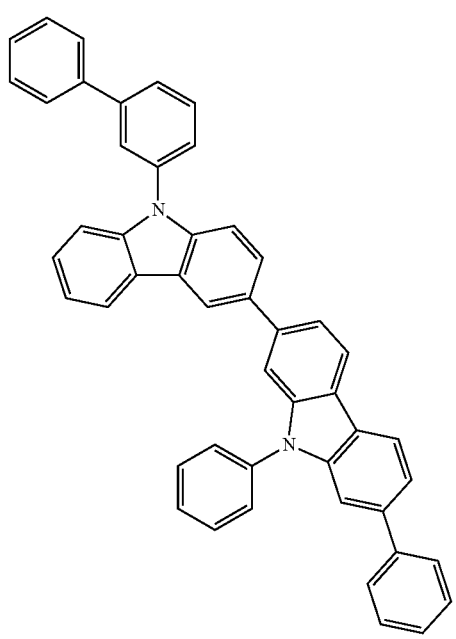
H-17
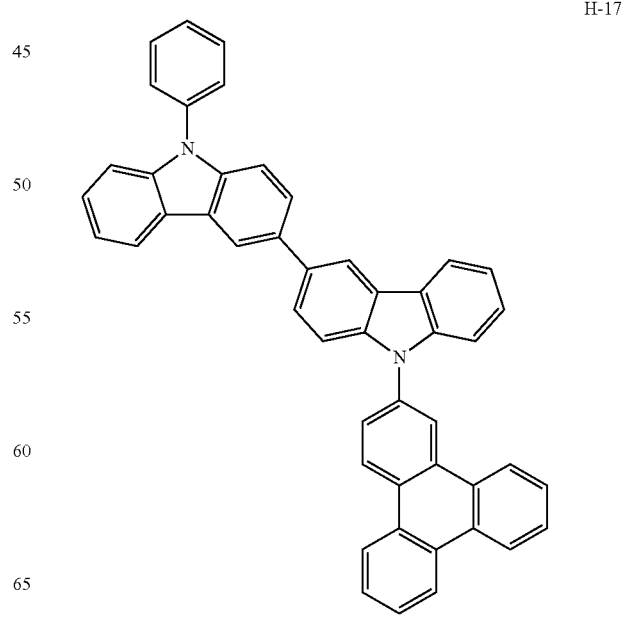

H-18
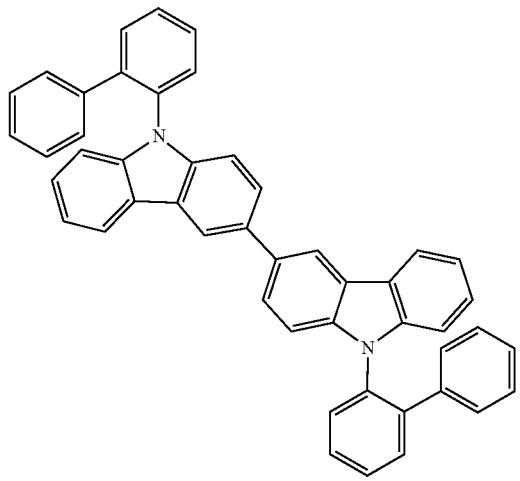
H-19
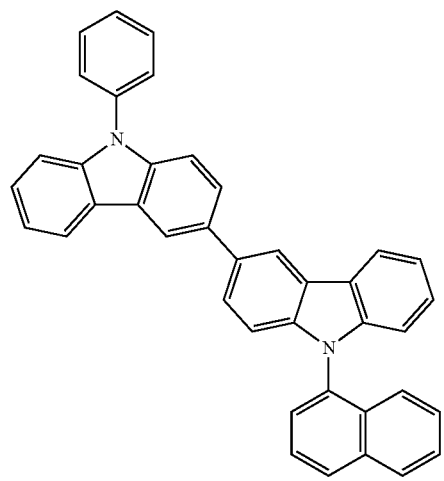
H-20
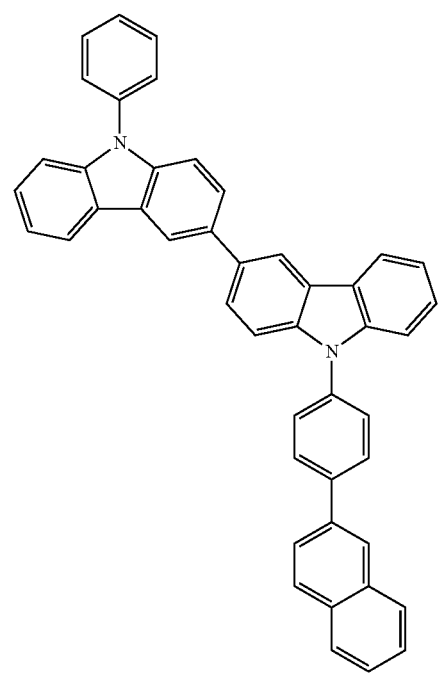
H-21
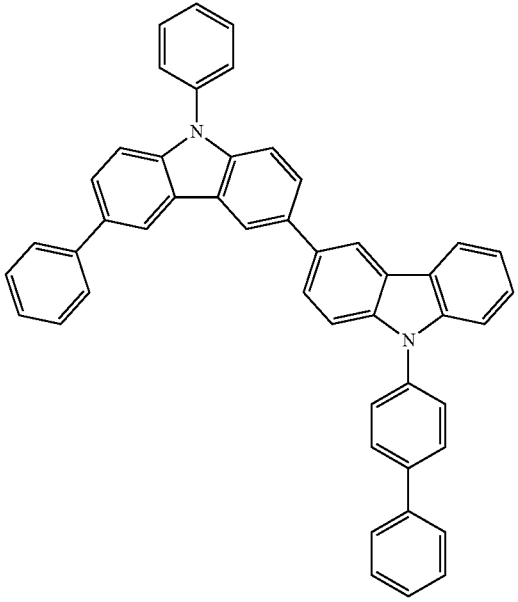
H-22
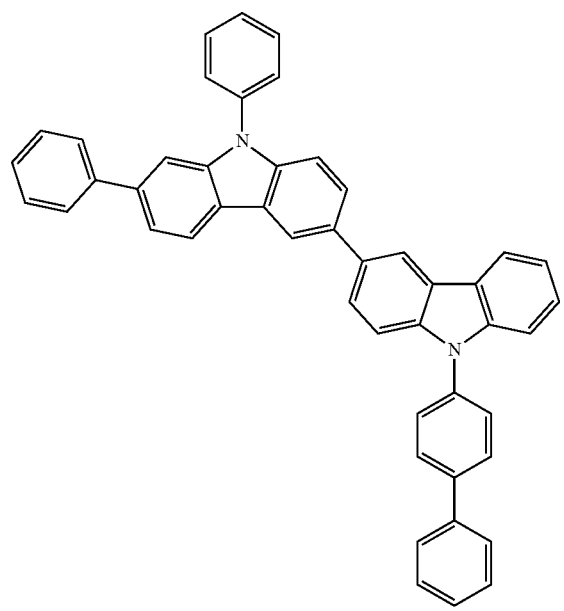

H-23
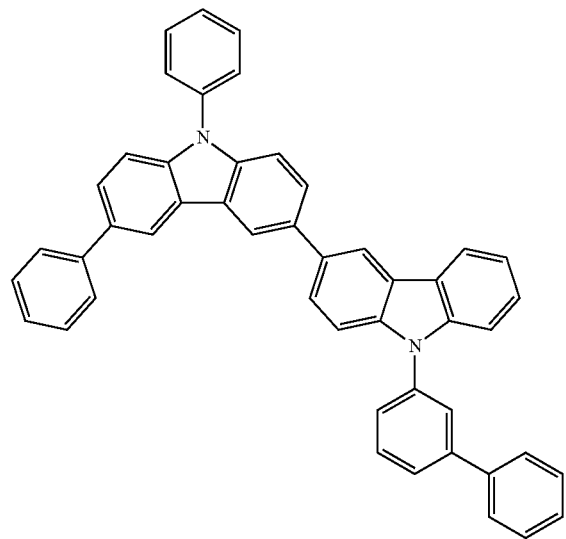
H-25
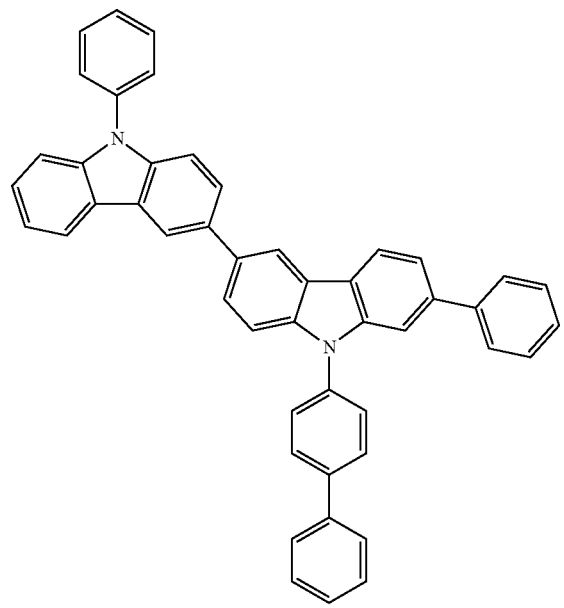
H-24
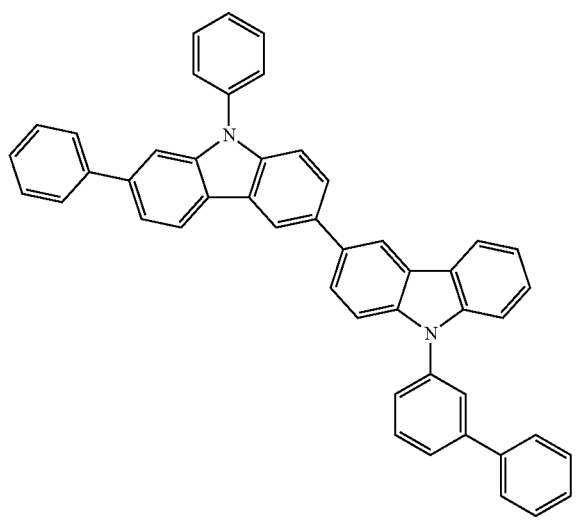
H-26
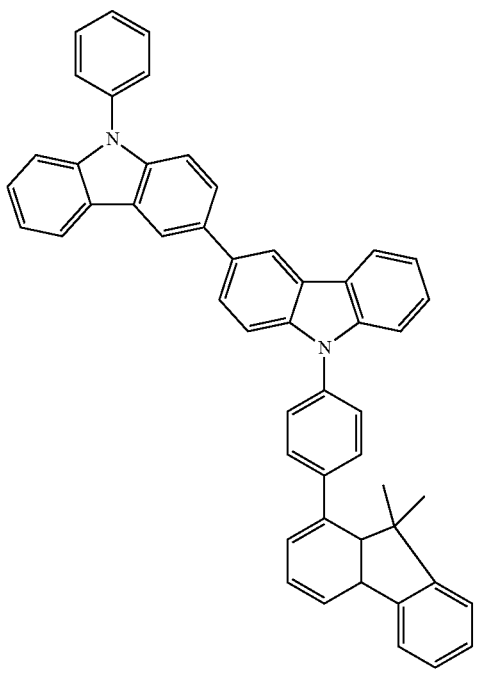

H-27
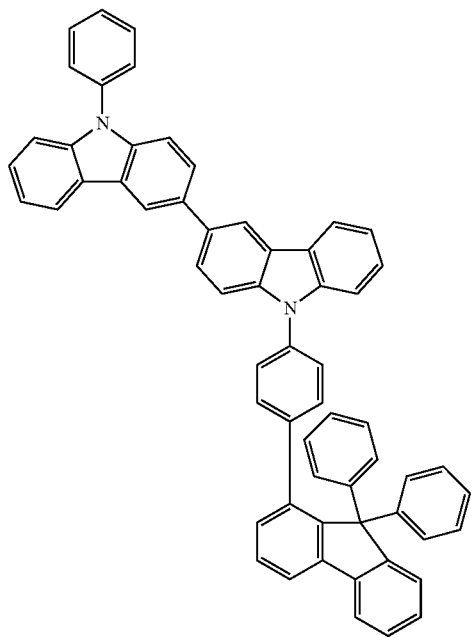
H-28
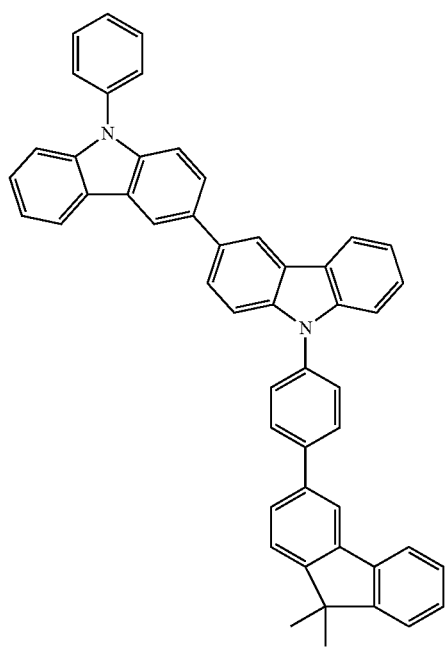
H-29
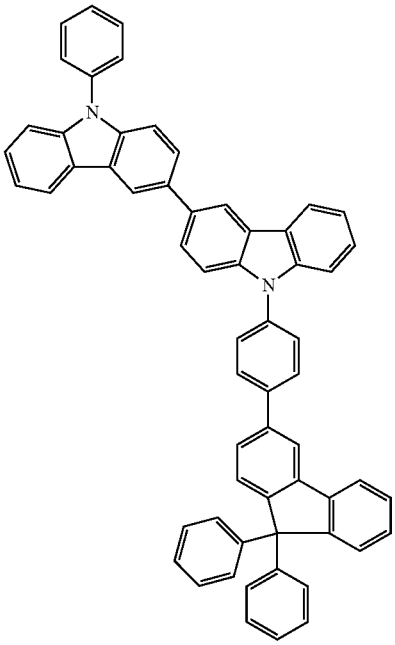
H-30
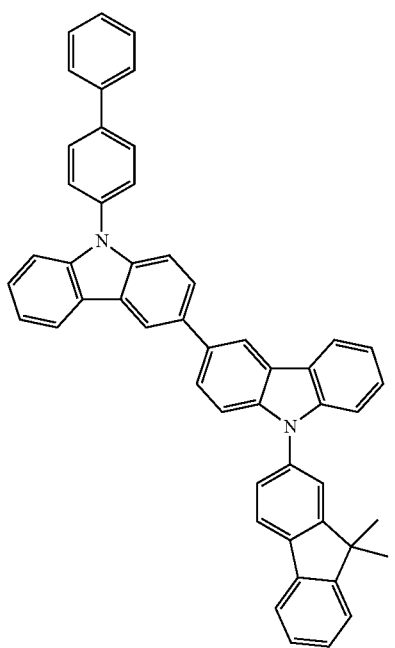

H-31
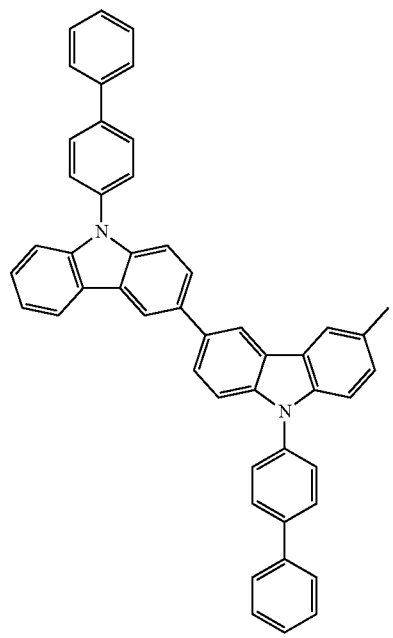
H-32
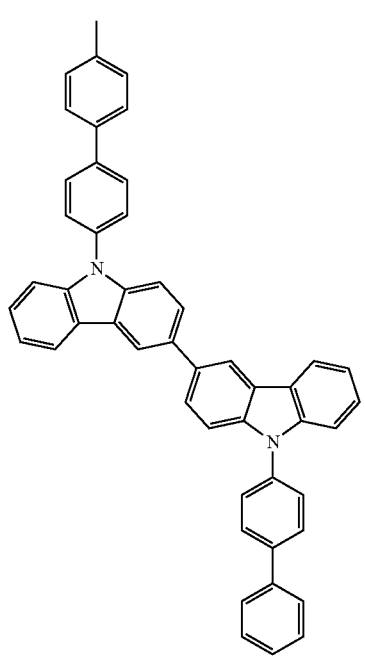
H-33
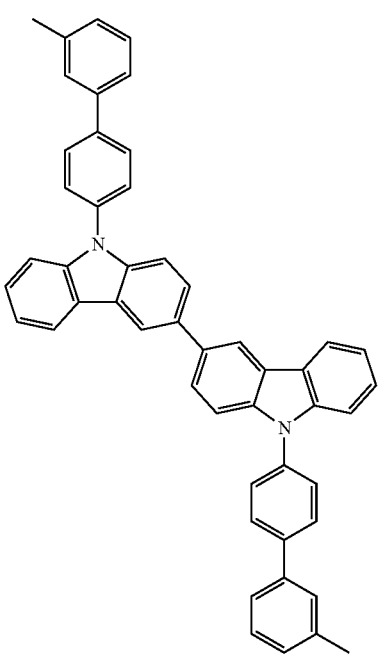
H-34
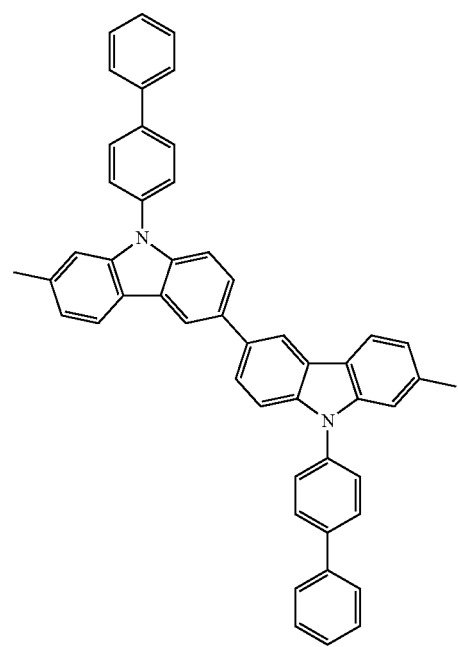

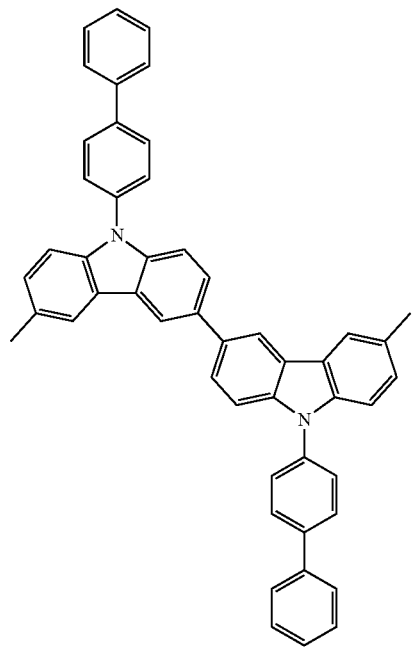
H-35
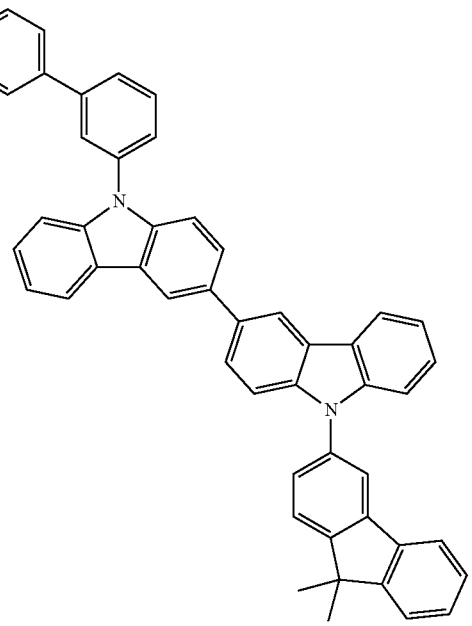
H-37
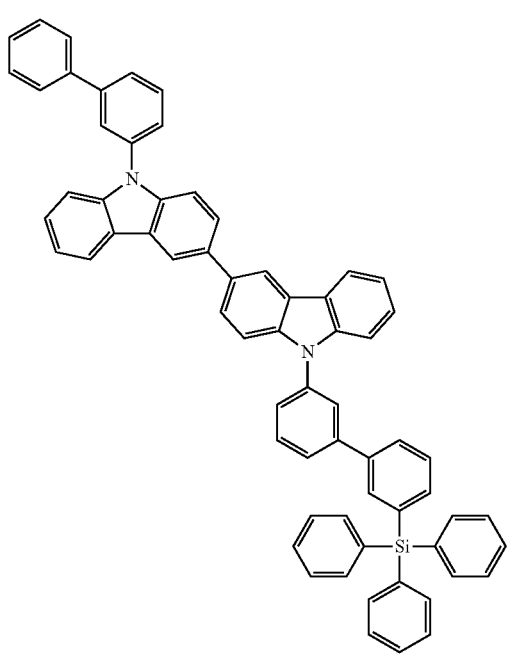
H-36
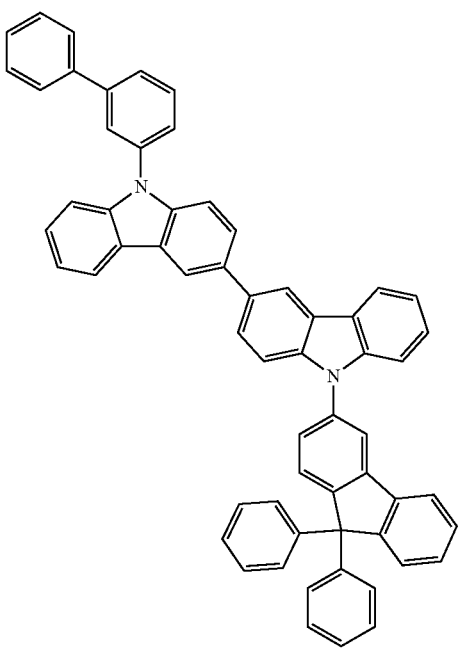
H-38

-continued
H-39
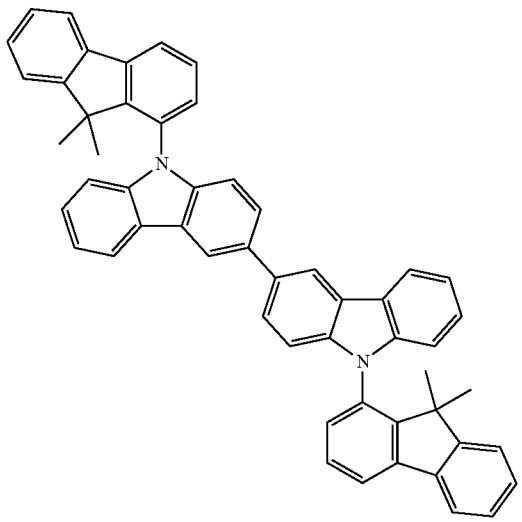
and
H-40
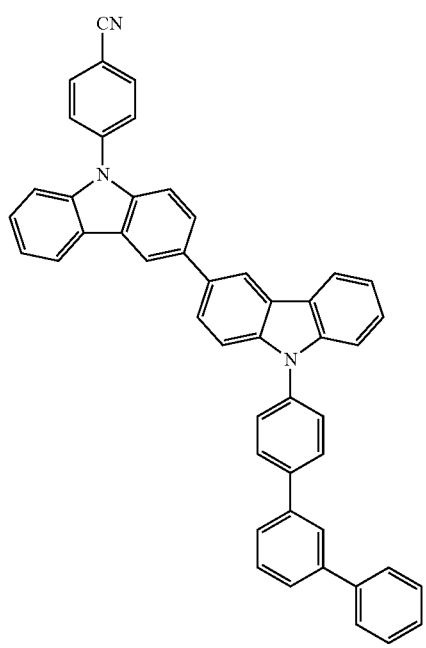
H-41
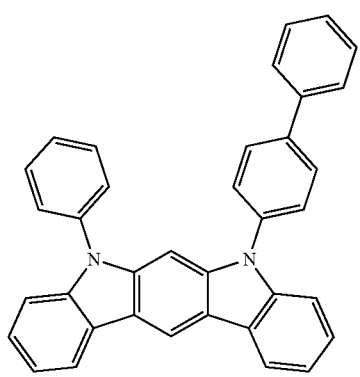
-continued
H-42
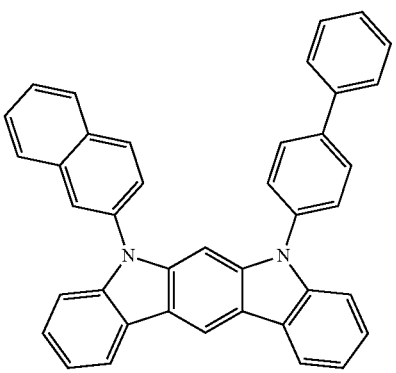
H-43
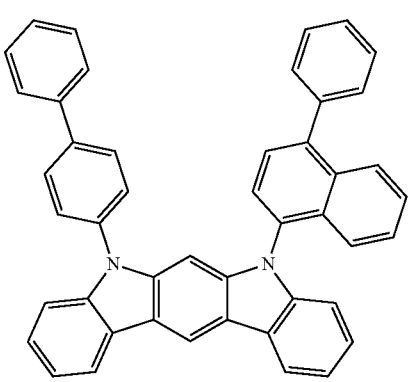
H-44
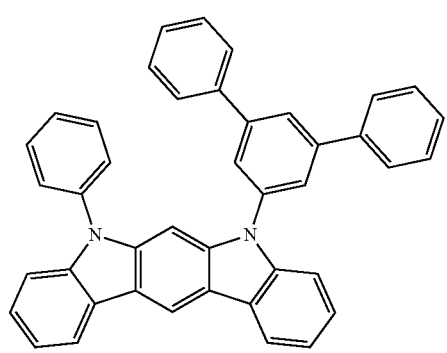
H-45
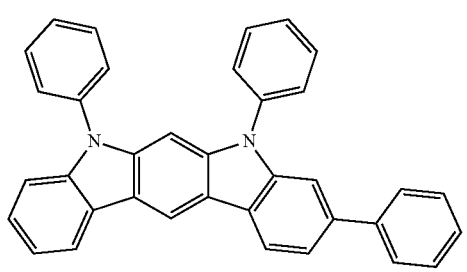

H-46
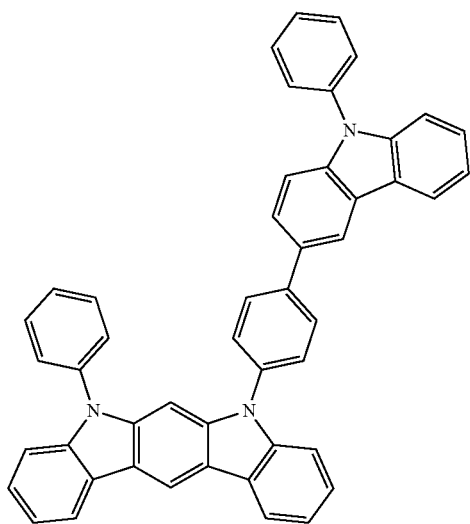
H-47
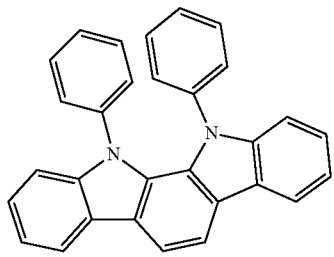
H-48
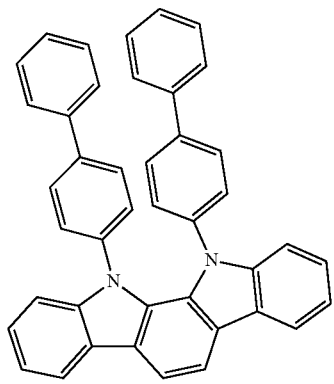
H-49
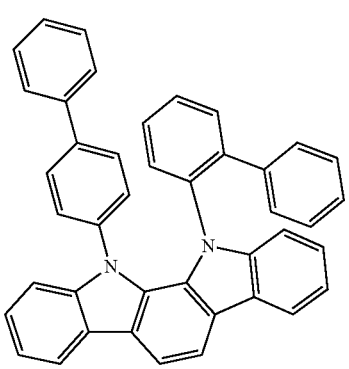
H-50
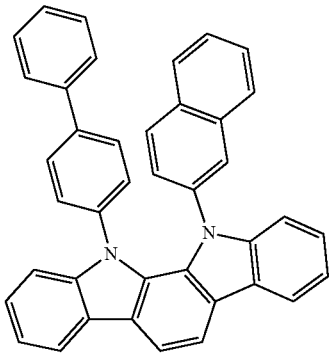
H-51
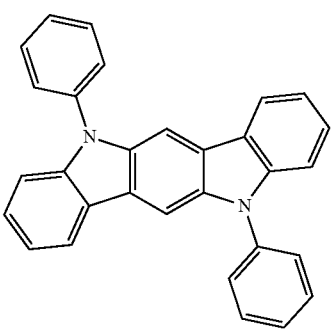
H-52
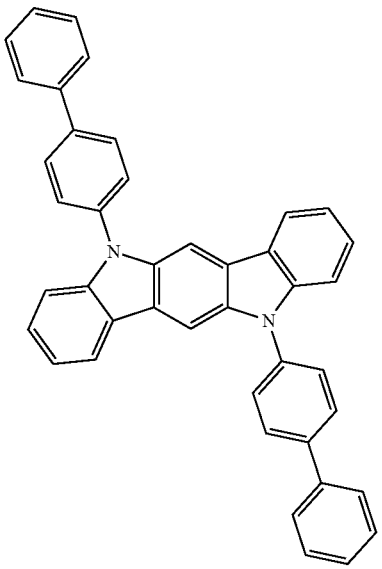

H-53
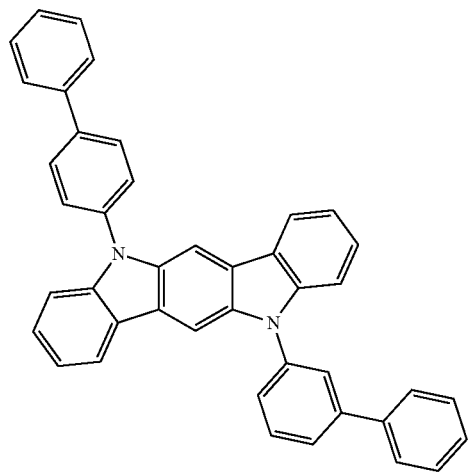
H-54
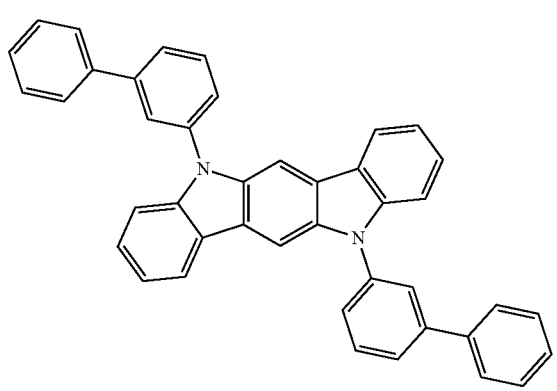
H-55
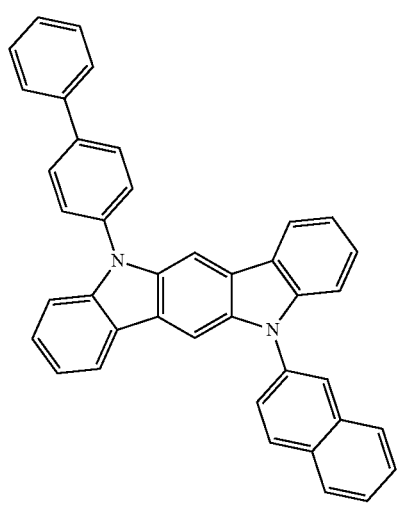
H-56
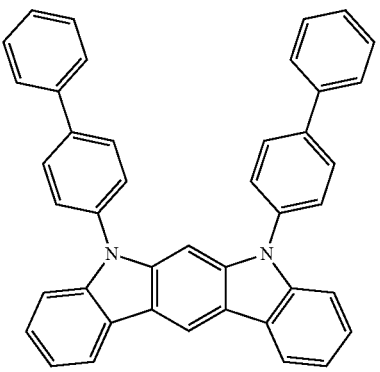
H-57
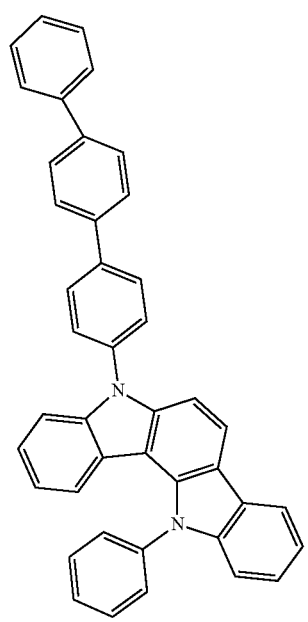
H-58
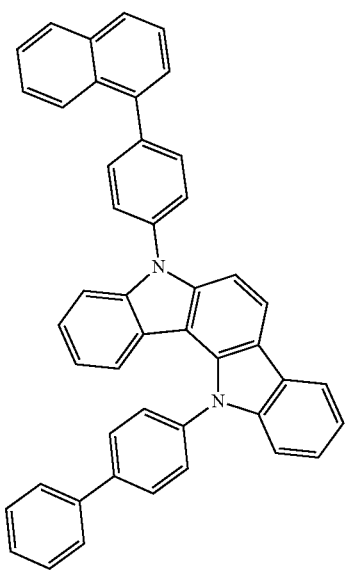

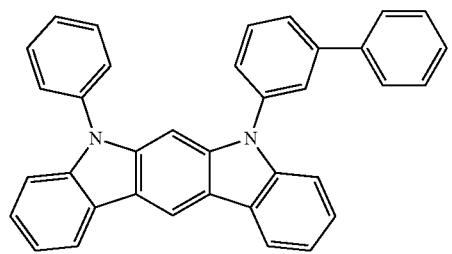 H-59
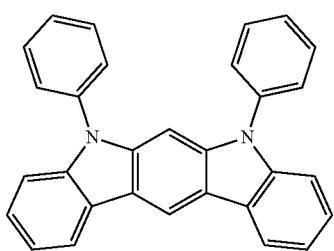 H-60
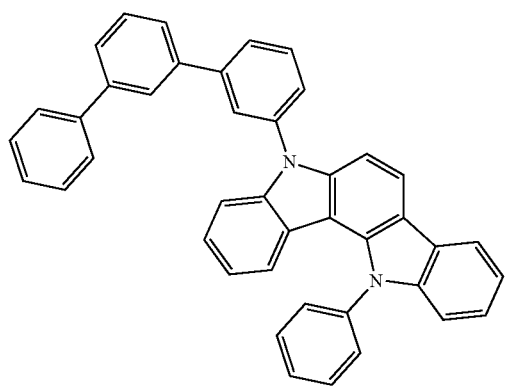 H-61
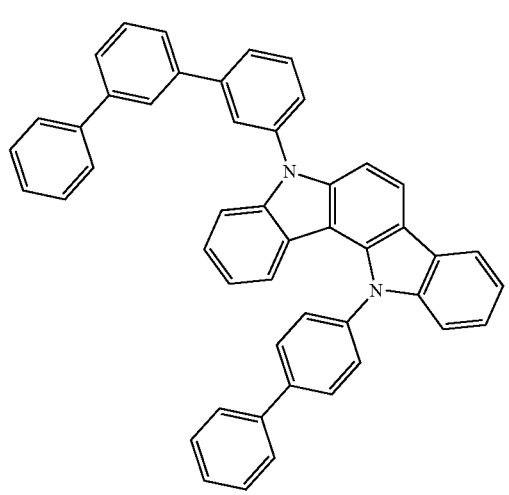 H-62
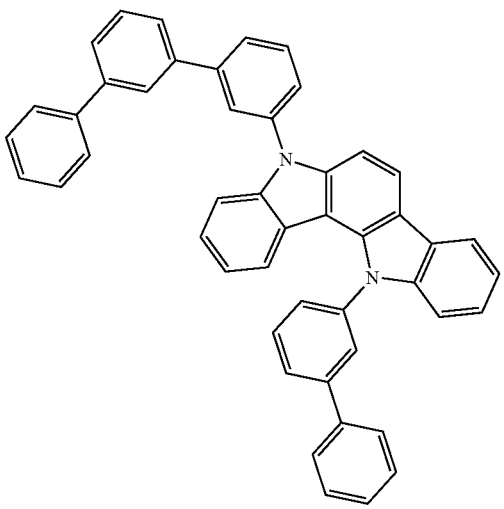 H-63
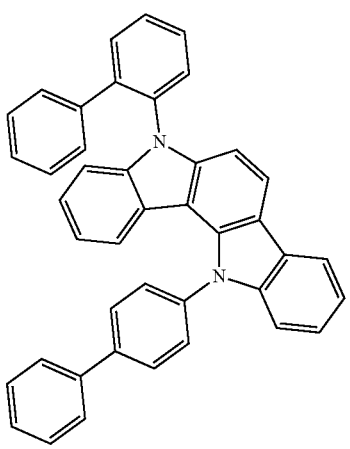 H-64
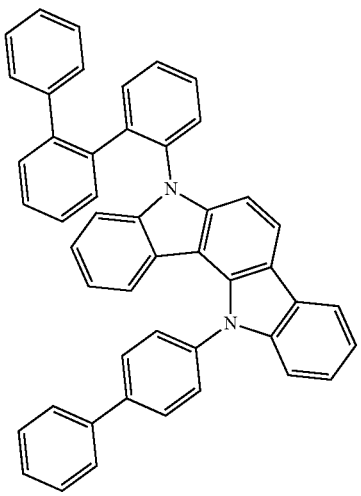 H-65

-continued
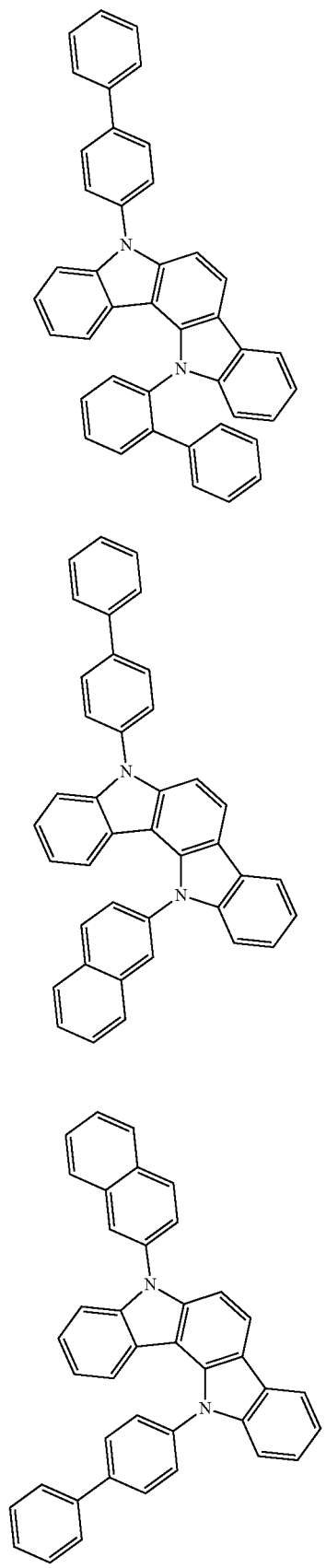
H-66
H-67
H-68
-continued
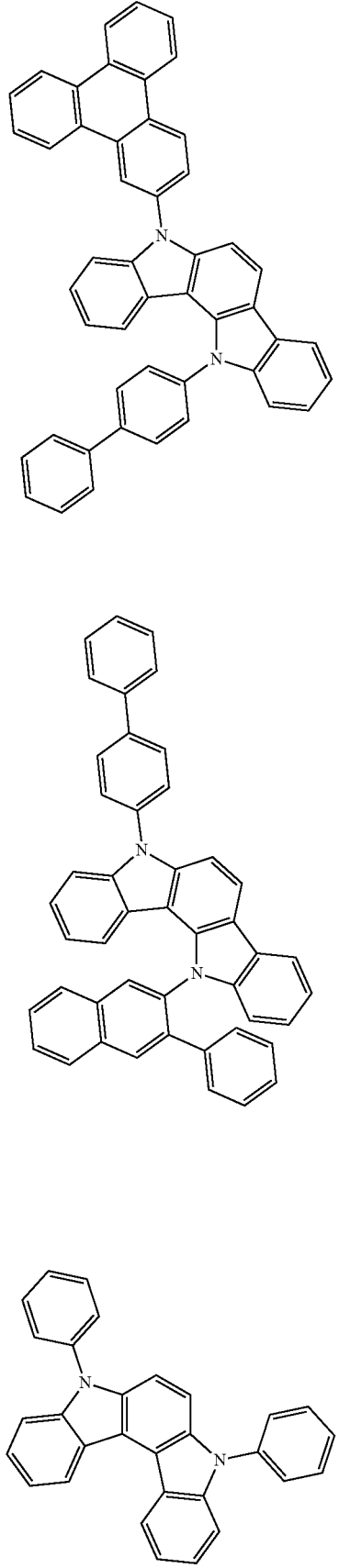
H-69
H-70
H-71

H-72
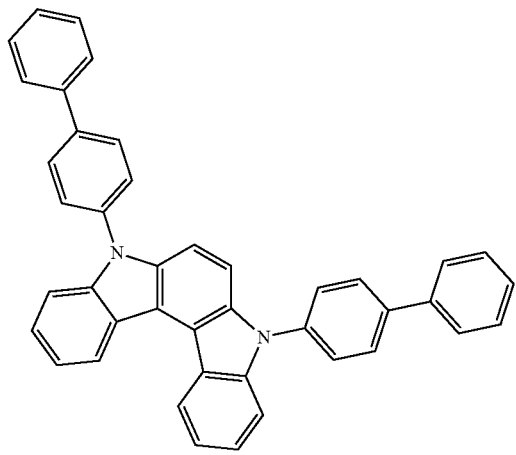
H-75
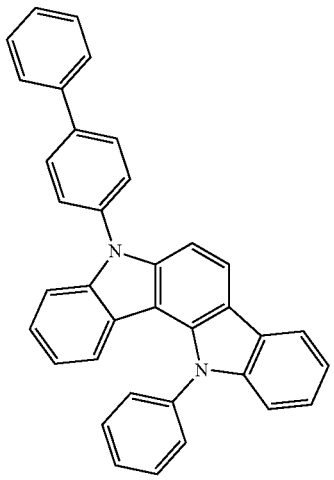
H-73
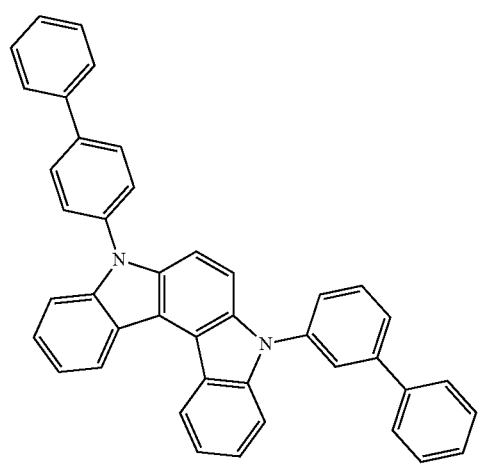
H-76
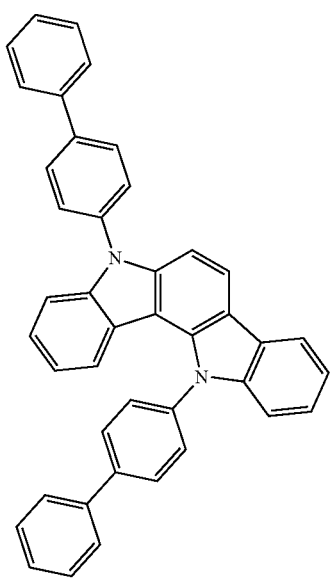
H-74
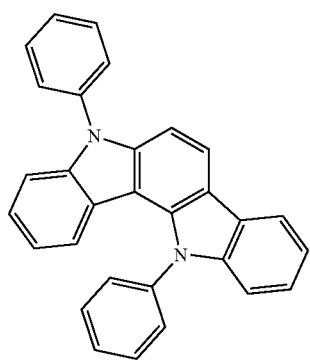
H-77
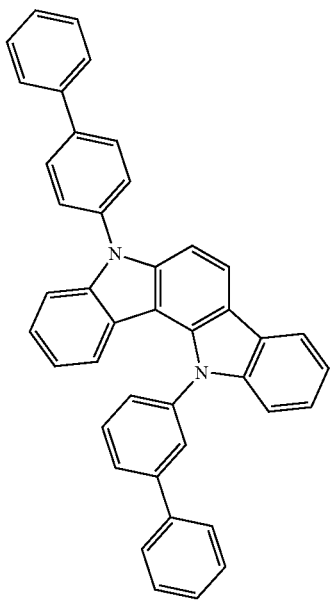

H-78
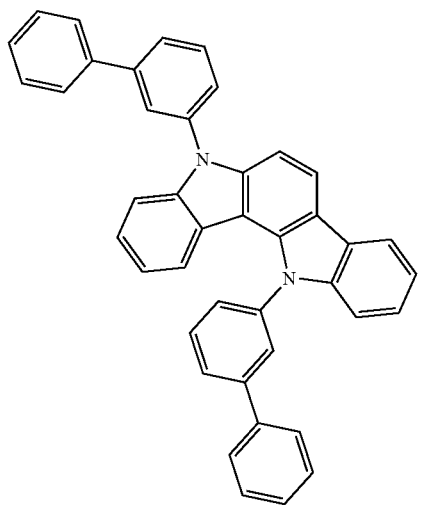
H-81
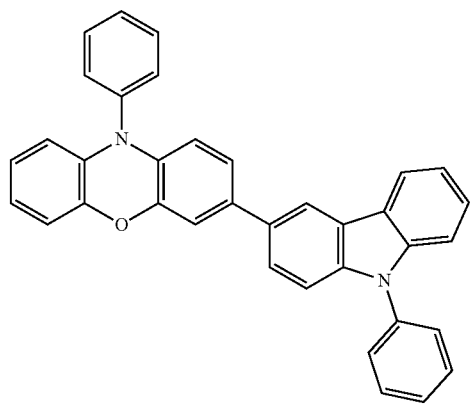
H-79
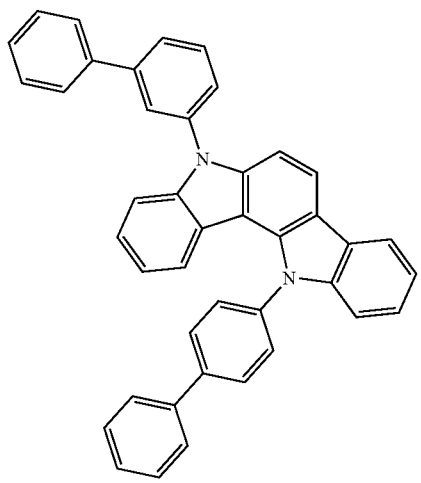
H-82
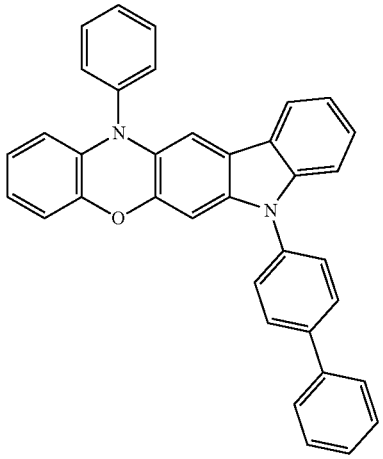
H-80
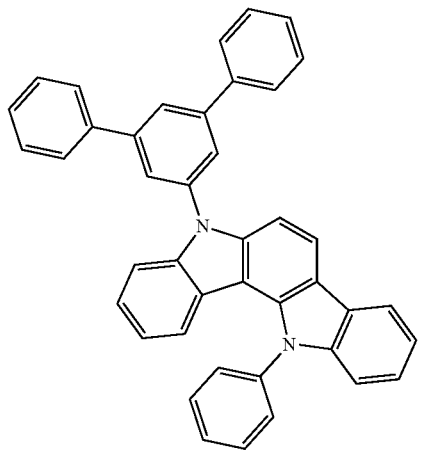
H-83
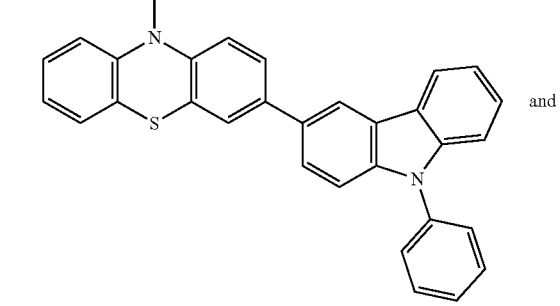
and -continued

H-84

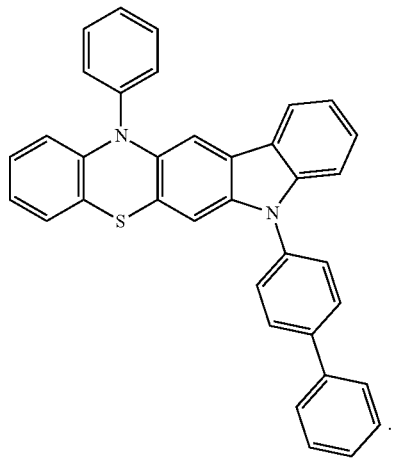

10. An organic electroluminescent device comprising the organic electroluminescent compound according to claim 1.

11. An organic electroluminescent device comprising: an anode; a cathode; and at least one light-emitting layer between the anode and the cathode, wherein the at least one light-emitting layer comprises the plurality of host materials according to claim 6.

* * * * *

UNITED STATES PATENT AND TRADEMARK OFFICE
CERTIFICATE OF CORRECTION

PATENT NO. : 12,102,001 B2  
APPLICATION NO. : 17/188999  
DATED : September 24, 2024  
INVENTOR(S) : Young-Kwang Kim et al.

Page 1 of 2

It is certified that error appears in the above-identified patent and that said Letters Patent is hereby corrected as shown below:

In the Claims

1. In Claim 1, the formula (1-14). The formular appearing in Column 156, from Line 5 to Line 12:

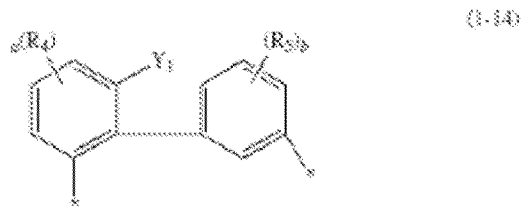

Should be:

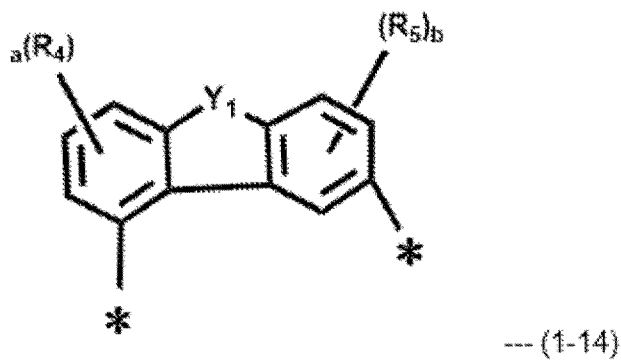

Signed and Sealed this  
Third Day of December, 2024

Katherine Kelly Vidal  
*Director of the United States Patent and Trademark Office*